US011317999B2

(12) United States Patent
Kopelman et al.

(10) Patent No.: US 11,317,999 B2
(45) Date of Patent: May 3, 2022

(54) AUGMENTED REALITY ENHANCEMENTS FOR DENTAL PRACTITIONERS

(71) Applicant: Align Technology, Inc., San Jose, CA (US)

(72) Inventors: Avi Kopelman, Palo Alto, CA (US); Adi Levin, Nes Tziona (IL); Eric Paul Meyer, Calabasas, CA (US); Elad Zeiri, Petach Tikva (IL); Amir Ashkenazi, Kiriat Ono (IL); Ron Ganot, Yad Rambam (IL); Sergei Ozerov, Moscow (RU); Inna Karapetyan, Modiin (IL)

(73) Assignee: Align Technology, Inc., San Jose, CA (US)

( * ) Notice: Subject to any disclaimer, the term of this patent is extended or adjusted under 35 U.S.C. 154(b) by 0 days.

(21) Appl. No.: 17/142,081

(22) Filed: Jan. 5, 2021

(65) Prior Publication Data

US 2021/0121271 A1    Apr. 29, 2021

Related U.S. Application Data

(63) Continuation of application No. 16/851,035, filed on Apr. 16, 2020, now Pat. No. 11,051,914, which is a
(Continued)

(51) Int. Cl.
*A61C 9/00* (2006.01)
*A61B 90/00* (2016.01)
(Continued)

(52) U.S. Cl.
CPC .......... *A61C 9/0053* (2013.01); *A61B 5/0088* (2013.01); *A61B 34/10* (2016.02);
(Continued)

(58) Field of Classification Search
CPC ....... A61C 9/0053; A61C 1/082; A61C 19/04; A61C 5/44; A61C 9/0046; A61C 9/004;
(Continued)

(56) References Cited

U.S. PATENT DOCUMENTS 6,334,772 B1   1/2002  Taub et al.
6,334,853 B1   1/2002  Kopelman et al.
(Continued)

FOREIGN PATENT DOCUMENTS

KR      101678910 B1    12/2016
WO      2015110859 A1    7/2015
(Continued)

OTHER PUBLICATIONS

Rozenfeld, M. "ModiFace Is Transforming the Beauty Industry With Augmented Reality," the institute, IEEE, Jul. 25, 2016, 4 pages.

*Primary Examiner* — Jeffery A Brier
(74) *Attorney, Agent, or Firm* — Lowenstein Sandler LLP

(57) ABSTRACT

A processing device receives, from an image capture device associated with an augmented reality (AR) display, a plurality of images of a face of a patient. The processing device selects a subset of the plurality of images that meet one or more image selection criteria. The selection comprises determining, from the plurality of images, a first image that represents a first position extreme for the face; determining, from the plurality of images, a second image that represents a second position extreme of the face; selecting the first image; and selecting the second image. The processing device further generates a model of a jaw of the patient based at least in part on the subset of the plurality of images that have been selected.

28 Claims, 33 Drawing Sheets

Related U.S. Application Data continuation of application No. 15/841,196, filed on Dec. 13, 2017, now Pat. No. 10,888,399.

(60) Provisional application No. 62/435,565, filed on Dec. 16, 2016.

(51) Int. Cl.

| | | |
|---|---|---|
| *G16H 50/50* | (2018.01) | |
| *A61B 34/10* | (2016.01) | |
| *A61C 1/08* | (2006.01) | |
| *A61B 34/00* | (2016.01) | |
| *A61C 19/04* | (2006.01) | |
| *A61B 34/20* | (2016.01) | |
| *G16H 50/20* | (2018.01) | |
| *G16H 20/40* | (2018.01) | |
| *G16H 40/60* | (2018.01) | |
| *A61C 5/44* | (2017.01) | |
| *G06F 3/01* | (2006.01) | |
| *G16H 30/20* | (2018.01) | |
| *G16H 30/40* | (2018.01) | |
| *G06K 9/62* | (2006.01) | |
| *G06K 9/00* | (2006.01) | |
| *A61C 1/00* | (2006.01) | |
| *A61C 7/00* | (2006.01) | |
| *A61C 19/05* | (2006.01) | |
| *G06T 19/00* | (2011.01) | |
| *A61B 5/00* | (2006.01) | |
| *G06T 17/00* | (2006.01) | |
| *G09B 23/28* | (2006.01) | |
| *A61B 17/00* | (2006.01) | |
| *G02B 27/01* | (2006.01) | |
| *A61B 90/50* | (2016.01) | |
| *A61B 6/00* | (2006.01) | |
| *G02B 27/00* | (2006.01) | |
| *A61B 1/24* | (2006.01) | |
| *A61B 5/103* | (2006.01) | |
| *A61B 6/14* | (2006.01) | |
| *A61B 1/00* | (2006.01) | |
| *G06N 3/08* | (2006.01) | |
| *A61B 90/30* | (2016.01) | |
| *G06N 20/10* | (2019.01) | |

(52) U.S. Cl.
CPC .............. *A61B 34/20* (2016.02); *A61B 34/25* (2016.02); *A61B 90/36* (2016.02); *A61C 1/0015* (2013.01); *A61C 1/082* (2013.01); *A61C 5/44* (2017.02); *A61C 7/002* (2013.01); *A61C 9/004* (2013.01); *A61C 9/0046* (2013.01); *A61C 19/04* (2013.01); *A61C 19/05* (2013.01); *G06F 3/011* (2013.01); *G06K 9/00281* (2013.01); *G06K 9/6212* (2013.01); *G06T 17/00* (2013.01); *G06T 19/006* (2013.01); *G09B 23/283* (2013.01); *G16H 20/40* (2018.01); *G16H 30/20* (2018.01); *G16H 30/40* (2018.01); *G16H 40/60* (2018.01); *G16H 50/20* (2018.01); *G16H 50/50* (2018.01); *A61B 1/00009* (2013.01); *A61B 1/00045* (2013.01); *A61B 1/00172* (2013.01); *A61B 1/24* (2013.01); *A61B 5/1032* (2013.01); *A61B 5/4542* (2013.01); *A61B 5/4547* (2013.01); *A61B 5/4552* (2013.01); *A61B 5/7455* (2013.01); *A61B 6/14* (2013.01); *A61B 6/466* (2013.01); *A61B 6/5217* (2013.01); *A61B 6/5247* (2013.01); *A61B 34/76* (2016.02); *A61B 2017/00216* (2013.01); *A61B 2034/102* (2016.02); *A61B 2034/105* (2016.02); *A61B 2034/107* (2016.02); *A61B 2034/2048* (2016.02); *A61B 2034/2065* (2016.02); *A61B 2034/252* (2016.02); *A61B 2034/254* (2016.02); *A61B 2034/256* (2016.02); *A61B 2034/258* (2016.02); *A61B 2090/062* (2016.02); *A61B 2090/309* (2016.02); *A61B 2090/365* (2016.02); *A61B 2090/3612* (2016.02); *A61B 2090/371* (2016.02); *A61B 2090/372* (2016.02); *A61B 2090/373* (2016.02); *A61B 2090/502* (2016.02); *G02B 27/0093* (2013.01); *G02B 27/017* (2013.01); *G02B 2027/0178* (2013.01); *G06F 3/013* (2013.01); *G06N 3/08* (2013.01); *G06N 20/10* (2019.01); *G06T 2207/30036* (2013.01); *G06T 2210/41* (2013.01); *Y02A 90/10* (2018.01)

(58) Field of Classification Search
CPC ....... A61C 1/0015; A61C 7/002; A61C 19/05; A61B 90/36; A61B 34/10; A61B 34/25; A61B 34/20; A61B 5/0088; A61B 5/7455; A61B 2017/00216; A61B 2090/502; A61B 2090/372; A61B 2090/365; A61B 2034/107; A61B 6/5217; A61B 5/4542; A61B 2034/256; A61B 2034/252; A61B 34/76; A61B 2034/105; A61B 1/24; A61B 6/5247; A61B 5/1032; A61B 2090/062; A61B 6/14; A61B 2034/258; A61B 2034/102; A61B 5/4547; A61B 2090/3612; A61B 2090/371; A61B 1/00172; A61B 2034/254; A61B 5/4552; A61B 2034/2065; A61B 1/00045; A61B 1/00009; A61B 2090/309; A61B 2034/2048; A61B 2090/373; A61B 6/466; G16H 50/50; G16H 50/20; G16H 20/40; G16H 40/60; G16H 30/20; G16H 30/40; G06F 3/011; G06F 3/013; G06K 9/6212; G06K 9/00281; G06T 19/006; G06T 17/00; G06T 2207/30036; G06T 2210/41; G09B 23/283; Y02A 90/10; Y02A 90/26; G02B 2027/0178; G02B 27/0093; G02B 27/017; G06N 3/08; G06N 20/10
See application file for complete search history.

(56) References Cited

U.S. PATENT DOCUMENTS

| | | |
|---|---|---|
| 7,249,952 B2 | 7/2007 | Ranta et al. |
| 7,711,447 B2 | 5/2010 | Lu et al. |
| 7,862,336 B2 | 1/2011 | Kopelman |
| 8,662,900 B2 | 3/2014 | Bell |
| 8,858,231 B2 | 10/2014 | Kopelman |
| 9,642,686 B1 | 5/2017 | Kalman |
| 2004/0091845 A1 | 5/2004 | Azerad et al. |
| 2004/0197727 A1 | 10/2004 | Sachdeva et al. |
| 2005/0048433 A1 | 3/2005 | Hilliard |
| 2007/0197902 A1 | 8/2007 | Schutyser |
| 2009/0017410 A1 | 1/2009 | Raby et al. |
| 2010/0015589 A1 | 1/2010 | Lehavi |
| 2010/0145898 A1 | 6/2010 | Malfliet et al. |
| 2010/0281370 A1 | 11/2010 | Rohaly et al. |
| 2011/0048433 A1 | 3/2011 | Pfister |
| 2011/0050848 A1 | 3/2011 | Rohaly et al. |
| 2011/0070554 A1 | 3/2011 | Kopelman et al. |
| 2013/0060532 A1 | 3/2013 | Clausen et al. |
| 2013/0325431 A1 | 12/2013 | See et al. |
| 2014/0071126 A1 | 3/2014 | Barneoud et al. |
| 2014/0215370 A1 | 7/2014 | Berry |
| 2014/0272764 A1 | 9/2014 | Miller et al. |

(56) References Cited

U.S. PATENT DOCUMENTS

| | | |
|---|---|---|
| 2014/0272774 A1 | 9/2014 | Dillon et al. |
| 2015/0025907 A1 | 1/2015 | Trosien et al. |
| 2015/0049081 A1 | 2/2015 | Coffey et al. |
| 2015/0320320 A1 | 11/2015 | Kopelman et al. |
| 2015/0335404 A1 | 11/2015 | Webber et al. |
| 2015/0336299 A1 | 11/2015 | Tanugula et al. |
| 2015/0350517 A1 | 12/2015 | Duret et al. |
| 2016/0128624 A1 | 5/2016 | Matt |
| 2016/0220105 A1 | 8/2016 | Duret |
| 2016/0324598 A1 | 11/2016 | Bothorel et al. |
| 2017/0065379 A1 | 3/2017 | Cowburn et al. |
| 2017/0202483 A1 | 7/2017 | Sorimoto et al. |
| 2018/0110590 A1 | 4/2018 | Maraj et al. |
| 2018/0168781 A1 | 6/2018 | Kopelman et al. |
| 2018/0206940 A1 | 7/2018 | Kopelman et al. |
| 2018/0280091 A1 | 10/2018 | Wang et al. |

FOREIGN PATENT DOCUMENTS

| | | |
|---|---|---|
| WO | 2015123759 A1 | 8/2015 |
| WO | 2016200167 A1 | 12/2016 |
| WO | 2017144934 A1 | 8/2017 |

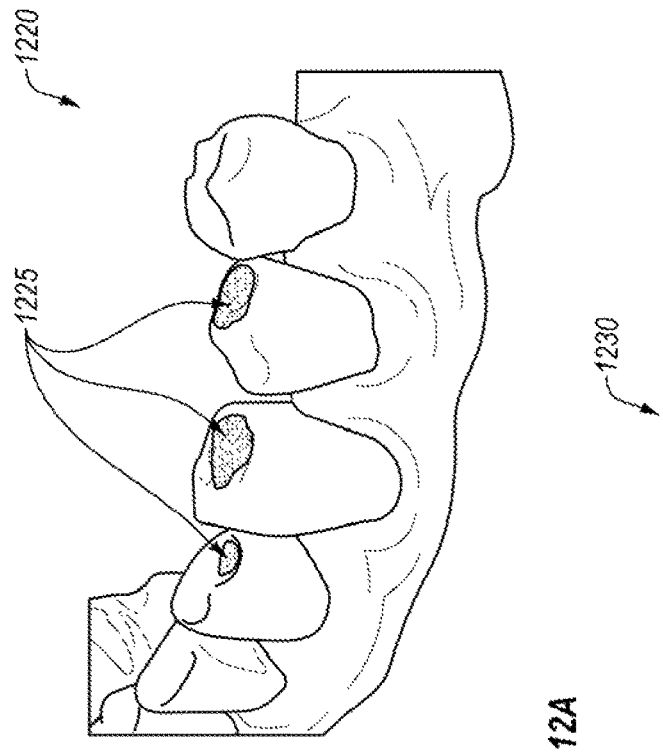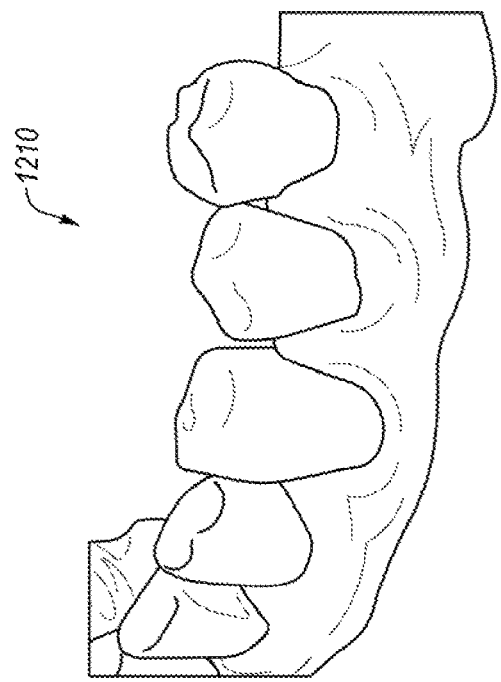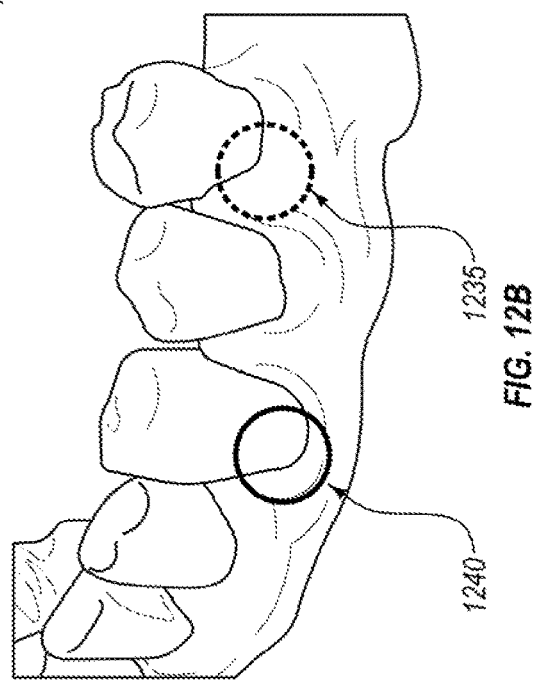
FIG. 12A
FIG. 12B

AUGMENTED REALITY ENHANCEMENTS FOR DENTAL PRACTITIONERS

RELATED APPLICATIONS

This patent application is a continuation of U.S. patent application Ser. No. 16/851,035, filed Apr. 16, 2020, which is a continuation of U.S. patent application Ser. No. 15/841, 196, filed Dec. 13, 2017, which claims the benefit under 35 U.S.C. § 119(e) of U.S. Provisional Application No. 62/435, 565, filed Dec. 16, 2016, all of which are incorporated by reference herein. This patent application is also related to U.S. patent application Ser. No. 15/841,200, filed Dec. 13, 2017, which is incorporated by reference herein.

TECHNICAL FIELD

Embodiments of the present invention relate to the field of dentistry and, in particular, to a system and method for providing augmented reality enhancements for dental practitioners.

BACKGROUND

Augmented reality devices may provide additional information to users of the devices in the context of the surrounding real world environment. For example, an augmented reality device may provide audio, video, graphic, or other information to a user to supplement the information available in the real world environment.

BRIEF DESCRIPTION OF THE DRAWINGS

Embodiments of the present invention are illustrated by way of example, and not by way of limitation, in the figures of the accompanying drawings.

FIG. 12A illustrates a portion of an example augmented reality display showing areas of interest, in accordance with an embodiment.

FIG. 12B illustrates a portion of an example augmented reality display showing areas of interest, in accordance with an embodiment.

DETAILED DESCRIPTION

Figure 1A:
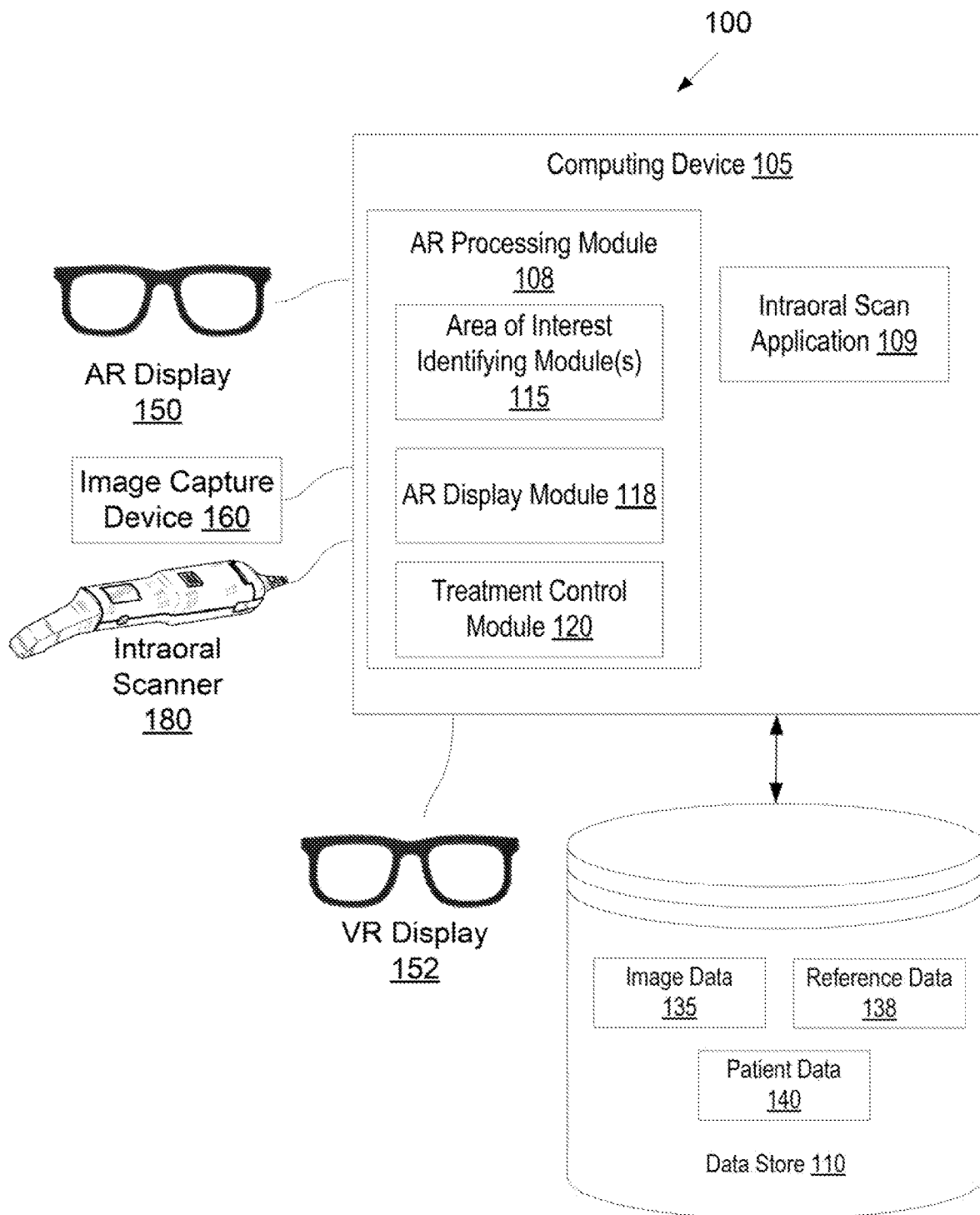
FIG. 1A illustrates one embodiment of an augmented reality system for enhancing the dental practice of dental practitioners, in accordance with an embodiment.

Described herein are methods and apparatuses for providing augmented reality (AR) enhancements to dentists, orthodontists, dental hygienists, or other dental practitioners. Also described is an intraoral scanner that includes an AR display. An AR system (also referred to herein as an AR device) may provide real-time information to a dental practitioner based on an analysis of the mouth and/or dental arch of a patient as viewed through an AR display. For example, the AR system may provide information about a dental arch based on images captured of the patient by the AR system. The AR system may also provide additional information based on a comparison of images captured by the AR system and previous data recorded for the patient. For example, previous images, scans, models, clinical data or other patient history may be compared to the images captured by the AR system, and a result of the comparison may be provided to the dental practitioner as a visual overlay on the real-world scene viewed by the dental practitioner through an AR display of the AR system. Previous data about the patient may also be provided in the visual overlay. Additionally, image data from the AR system may be used to facilitate dental procedures such as drilling, grinding of a tooth, placement of an attachment on a tooth, placement of a bracket on a tooth (e.g., a bracket placed in the middle of the crown of a tooth), placement of other objects in pre-defined or automatically identified positions, intraoral scanning, and so on. The AR system may update information provided to a dental practitioner or provide feedback to the dental practitioner in real time or near real time during the course of the dental practitioner interacting with the patient.

In some embodiments, an AR system may provide information to the dental practitioner based on analysis of image data without using previous information about the patient. For example, the AR system may analyze an image or stream of images of a patient's oral cavity and dental arch and determine an area of interest present in the image data. The AR system may determine if one or more teeth in an image indicate excessive wear, plaque, deposits, cracks, cavities, or other characteristics of interest to dental practitioners. The areas of interest may be determined based on processing an image of a dental arch or tooth taken by the AR system using one or more dental condition profiles in a data store. In some embodiments, the AR system may analyze an image of a tooth, multiple teeth, or a dental arch using dental condition profiles generated using machine learning techniques and training data of previous images of teeth.

After the AR system determines one or more areas of interest, the AR display may then display real world data to a dental practitioner along with a visual overlay highlighting the areas of interest to the dental practitioner. In an example, the AR display may include lenses through which a wearer views the physical world, and the visual overlay may be projected onto the lenses. Alternatively, the visual overlay may be projected directly onto a wearer's eyes. For example, a tooth may be highlighted in a different color, circled, or otherwise indicated as having a characteristic in a visual overlay displayed by the AR system. In some embodiments, the AR system may provide different indicators for different characteristics or dental conditions. In some embodiments, an area of interest may be highlighted, and a reason for the area of interest may be output in another portion of the display of the AR system or may be output in another manner, such as audio. In some embodiments, the AR system may also enhance a live view of the patient, such as by providing light enhancements that improve viewing of the patient or providing a zoomed in image of a portion of a patient's mouth.

In some embodiments, the AR system may provide information to the dental practitioner based on analysis of the patient and/or in view of previous patient data. For example, the AR system may compare images or models from a previous visit to current images of the patient's dental arch. The AR system may then determine one or more areas of interest based on the comparison. For example, the AR system may identify changes since a last scan, analysis of wear over time, feedback on orthodontic treatment, or other analysis of changes. The AR system may then mark the changes on a display of the AR system. In some embodiments, the AR system may also superimpose previous patient data on a display. For example, the AR system may show a previous scan or previous dental arch superimposed onto a display.

In some embodiments, the AR system may provide interactive feedback or other updated information to the dental practitioner based on an interaction with the patient. For example, the feedback may be provided during an intra-oral treatment such as a dental procedure. In some embodiments, the AR system may output to a display of the AR system recommended steps to take during an implant procedure, drilling procedure, grinding procedure, etc. For example, the AR system may show where to remove material for an insertion path, potential undercuts of neighboring teeth, placement of a hole for an implant, drilling depth, drilling direction, or the like. Similarly, the AR system may provide an indication of material to remove during interproximal reduction. In some embodiments, the AR system may provide feedback regarding placement of an attachment on a tooth. In some embodiments, the AR system may superimpose an occlusion map onto the patient's teeth in a display of the AR system. The AR system may also update a superimposed occlusion map if it changes while a dental practitioner is performing a dental procedure. An AR system may also provide feedback based on other information or analysis performed on images or other data received about a patient.

Embodiments provide significant advantages over traditional techniques for dentistry and orthodontics, and can improve every aspect of a dental practice. Dental hygienists can use an AR system as described herein to better interact with a patient and identify potential dental issues that a dental hygienist is qualified to address, such as gum swelling or plaque caused by poor dental hygiene. The AR system may automatically process image data from the image capture device to identify, for example, tooth wear, gum swelling, gum discoloration, plaque, etc. and call these dental conditions to the attention of the dental hygienist. Similarly, a dentist may use an AR system that provides real-time feedback as described herein to improve his or her accuracy in performing intraoral procedures such as drilling a tooth, grinding a tooth, placing an attachment on a tooth, placing an implant, and so on. The AR system also presents information to a dental practitioner while the dental practitioner views a patient, and may reduce or eliminate a need for the dental practitioner to look away from the patient to a computer screen or chart. Additionally, an orthodontist may use an AR system as described herein to improve his analysis of how an orthodontic treatment plan is progressing, to improve performance of intraoral procedures, and so on. Embodiments therefore improve the efficiency of interfacing with patients, the accuracy of dental procedures and the identification of dental conditions. For example, embodiments enable a dental practitioner to work while looking exclusively at the patient's jaws, without any reason to turn his or her head toward a screen or monitor (e.g., of a computing device for an intraoral scanner).

In some embodiments, an intraoral scanner uses an AR display as a primary or secondary display for controlling an intraoral scanning procedure. The AR display may be worn by a dental practitioner that uses the intraoral scanner to image a patient's dental arch and generate a virtual three-dimensional model of that dental arch. The AR display may provide a two-dimensional (2-D) or three-dimensional (3-D) menu of options for controlling the intraoral scan procedure. Additionally, the AR display may be used to provide a zoomed in view of a region of the dental arch being scanned. Additionally, the AR display may be used to provide a virtual overlay of a virtual 3-D model of the dental arch based on images generated by the intraoral scanner during an intraoral scan procedure.

During an intraoral scan procedure (also referred to as a scan session), a user (e.g., a dental practitioner) of an intraoral scanner may generate multiple different images (also referred to as scans or medical images) of a dental site, model of a dental site, or other object. The images may be discrete images (e.g., point-and-shoot images) or frames from a video (e.g., a continuous scan). Existing medical scanning solutions frequently involve the user holding the scanner to engage the patient for scanning, disengaging from the patient to address a medical scan application executing on a computing device, then reengaging with the patient to continue the scanning process, again disengaging from the patient to address the medical scan application, and repeating until completion of a scanning session. Such processes can be quite cumbersome and inefficient. Moreover, medical scanning devices generally lack the ability to both generate medical images and then manipulate those medical images or representations thereof on a display of a computing device.

Embodiments of the present invention enable a user to perform operations (such as to control or navigate a user interface and/or to manipulate intraoral images or a representation generated from intraoral images) while still engaged with a patient that in previous systems could only be performed by disengaging from the patient and interacting with a computing device running an intraoral scan application. The dental practitioner may see a menu for the intraoral scan application overlaid on a field of view of the dental practitioner while the dental practitioner remains focused on the patient. The ability to perform such operations while still engaged with the patient can improve the efficiency of a workflow for scanning a patient or performing other operations. This will save the dental practitioner time during treatment. It also allows the dental practitioner to see the effects of his or her work and enable him or her to correct and adjust treatment in real time as appropriate.

In some embodiments, an image capture device of an AR display may be used to generate multiple images of a patient's face. The image capture device may generate a stream of images, and processing logic may analyze the stream of images to select a subset of those images. The selected subset of images may then be saved and used to generate a model associated with a dental arch or jaw, such as an articulation model of the patient's jaw. Additionally, a dental practitioner wearing the AR display may generate voice notes and append those voice notes to images taken by the image capture device of the AR display.

Embodiments described herein are discussed with reference to an AR system. An AR system is a device that enables a live direct or indirect view of a physical, real-world environment and that augments the view of the physical real-world environment by computer generated sensory input such as sound, video, or graphics. An AR system may include an AR display that includes glasses or other lenses that have one or more cameras attached to capture images of a patient. The AR display may also have a projector that projects images onto the glasses or lenses to provide a visual overlay to a dental practitioner. The visual overlay is superimposed over the real world image that the dental practitioner sees through the glasses or lenses. Some embodiments herein are described with reference to an AR display that is worn by a dental practitioner, such as AR glasses, AR goggles, or an AR headset. While some embodiments described herein are discussed with reference to a worn AR display, it should be understood that embodiments also apply to AR system that use other types of displays. For example, embodiments may apply to a computing device having a screen showing live images captured of a patient and overlay information to enhance the experience of the dental practitioner viewing the screen.

Additionally, it should be understood that embodiments described with reference to an AR system also apply to a virtual reality (VR) system. A VR system is similar to an AR system, except that an AR system allows a wearer or viewer to see an augmented version of the real world, while a VR system provides a purely simulated environment. A VR system artificially creates sensory experiences that can include sight, touch, sound, and/or other senses, and presents these sensory experiences onto a VR display. Any reference made herein to any type of AR system and/or AR display applies equally to a VR system and/or VR display.

FIG. 1A illustrates one embodiment of an AR system 100 for providing augmented reality enhancements to a dental practitioner. In one embodiment, the AR system 100 includes a computing device 105, an AR display 150, an image capture device 160, and a data store 110. In some embodiments, the image capture device 160 is a component of the AR display 150. In some embodiments, multiple components shown in FIG. 1A may be integrated into a device that houses the AR display 150. For example, the computing device 105 and image capture device 160 may be integrated into glasses or a headset to be worn by a dental practitioner. In some embodiments, the computing device 105 may be separate from the AR display 150, but connected through either a wired or wireless connection to a processing device in the AR display 150. Additionally, the data store 110 may be attached to the AR display 150, may be directly connected to computing device 105, and/or may be accessed by computing device 105 over a network (not shown). In some embodiments, the computing device 105 and data store 110 may be collocated and accessed by the AR display 150 over a network.

Computing device 105 may include a processing device, memory, secondary storage, one or more input devices (e.g., such as a keyboard, mouse, tablet, speakers, or the like), one or more output devices (e.g., a display, a printer, etc.), and/or other hardware components. Computing device 105 may be connected to data store 110 either directly or via a network. The network may be a local area network (LAN), a public wide area network (WAN) (e.g., the Internet), a private WAN (e.g., an intranet), or a combination thereof. The computing device 105 may be integrated into the AR display 150 or image capture device 160 in some embodiments to improve mobility.

Data store 110 may be an internal data store, or an external data store that is connected to computing device 105 directly or via a network. Examples of network data stores include a storage area network (SAN), a network attached storage (NAS), and a storage service provided by a cloud computing service provider. Data store 110 may include a file system, a database, or other data storage arrangement.

The AR display 150 may include lenses through which a wearer (e.g., a dental practitioner) may see a physical, real-world environment (e.g., a patient's oral cavity) and a projector for projecting visual elements onto the lenses. Examples of AR displays include HoloLens®, Google Glass®, Vuzix Smart Glasses®, and Sony SmartEyeGlass®. The AR display 150 may therefore overlay information for a dental practitioner onto the lenses in a position in the field of view of the practitioner that corresponds to a location of an identified area of interest. To determine where to display information, the AR display 150 may include one or more sensors to track the eyes of a user and/or determine a position of the user in relation to positions of objects viewed by the user. The AR display 150 may also use images provided from image capture device 160 to determine where to display information to the dental practitioner. In some embodiments the image capture device 160 is mounted to the AR display 150.

As a dental practitioner wearing the AR display 150 views a patient, image capture device 160 may generate a stream of images that show the patient from the dental practitioner's point of view. The image capture device may be or include a charge-coupled device (CCD) sensor and/or a complementary metal-oxide semiconductor (CMOS) sensor. The image capture device 160 may provide images or video to the computing device 105 for processing. For example, the image capture device 160 may provide images to the computing device 105 that the computing device analyzes to determine areas of interest on a dental arch or otherwise in an oral cavity viewed by a dental practitioner. The image capture device 160 may also provide images to the computing device 105 or AR display 150 that are used to coordinate the position of elements of a visual overlay to display on AR display 150 so that the visual overlay is superimposed over the real-world environment viewed by the dental practitioner. In some embodiments, the images captured by image capture device 160 may be stored in data store 110. For example, the image data 135 may be stored in data store 110 as a record of patient history or for computing device 105 to use for analysis of the patient. The image capture device 160 may transmit the discrete images or video to the computing device 105. Computing device 105 may store the image data 135 in data store 110.

In some embodiments, the image capture device 160 provides two-dimensional data. In some embodiments, the image capture device 160 may provide three-dimensional data or stereoscopic image data that may be processed to produce three-dimensional data. For example, the image capture device 160 may have two cameras with a known separation and known imaging angles that simultaneously capture image data. The stereoscopic image data may be provided to computing device 105 as a single stream of image data or as two separate streams of image data. The stereoscopic image data may be used to provide an estimation of depth for objects viewed through the AR display 150. For example, the computing device 105 may use the stereoscopic image data to identify a three dimensional location of a tooth in the field of view of the image capture device 160.

The image capture device 160 may include high definition cameras to accurately capture the structure of areas of interest of a patient. In some embodiments, the image capture device 160 may have one or more cameras that capture a wide field of view and additional cameras for capturing a narrow field of view (e.g., for a region identified as containing an area of interest). In some embodiments, the image capture device 160 may include additional cameras to provide additional streams of image data. Additional cameras may be used to improve three dimensional image quality.

In some embodiments, the image capture device 160 may include one or more light sources to illuminate a patient for capturing images. Such light sources may include infrared, ultraviolet, or other wavelength light sources (e.g., LEDs or the like). These light sources may illuminate an oral cavity to provide additional data over information available from the visible light spectrum. For example, certain wavelengths such as infrared or ultraviolet wavelengths may more clearly show certain dental conditions such as plaque or cavities. In addition, in some embodiments, light sources may provide structured light to enhance three dimensional mapping of image data received from image capture device 160. For example, the light sources may project lines or a grid onto viewed objects to provide additional information about depth to the computing device 105.

The computing device 105 may include AR processing module 108. The AR processing module 108 may analyze image data 135 from a data store 110 or directly from an image capture device 160. The AR processing module 108 may then identify areas of interest to present in a visual overlay on AR display 150 and/or generate additional information to present on the AR display 150. The information provided on an AR display 150 may depend on a procedure to be performed, a wearer of the AR display 150, information known about a patient, and so on. For example, during a routine checkup, the computing device 105 may provide patient history to a dental practitioner and/or display areas of interest identified based on image data 135. In some embodiments, the dental practitioner may input the identity of a procedure to be performed into AR processing module 108. For this purpose, the dental practitioner may choose the procedure from a number of preset options on a drop-down menu or the like, from icons or via any other suitable graphical input interface, or by speaking commands to the AR system. Alternatively, the identity of the procedure may be input in any other suitable way, for example by means of preset code, notation or any other suitable manner, AR processing module 108 having been suitably programmed to recognize the choice made by the user.

By way of non-limiting example, dental procedures may be broadly divided into prosthodontic (restorative) and orthodontic procedures, and then further subdivided into specific forms of these procedures. Additionally, dental procedures may include identification and treatment of gum disease, sleep apnea, and intraoral conditions. The term prosthodontic procedure refers, inter alia, to any procedure involving the oral cavity and directed to the design, manufacture or installation of a dental prosthesis at a dental site within the oral cavity, or a real or virtual model thereof, or directed to the design and preparation of the dental site to receive such a prosthesis. A prosthesis may include any restoration such as implants, crowns, veneers, inlays, onlays, and bridges, for example, and any other artificial partial or complete denture. The term orthodontic procedure refers, inter alia, to any procedure involving the oral cavity and directed to the design, manufacture or installation of orthodontic elements at a dental site within the oral cavity, or a real or virtual model thereof, or directed to the design and preparation of the dental site to receive such orthodontic elements. These elements may be appliances including but not limited to brackets and wires, retainers, clear aligners, or functional appliances. Any of these orthodontic procedures and/or dental procedures may be facilitated by the AR system described herein.

In one embodiment, AR processing module 108 includes one or more area of interest (AOI) identifying modules 115, an AR display module 118, and a treatment control module 120. Alternatively, the operations of one or more of the AOI identifying modules 115, AR display module 118, and/or treatment control module 125 may be combined into a single module and/or divided into multiple modules.

AOI identifying modules 115 are responsible for identifying areas of interest (AOIs) from image data 135 received from image capture device 160. The image data may be images of a patient's oral cavity viewed by a dental practitioner wearing the AR display 150. The AOI identifying modules 115 may also identify AOIs from reference data 138, which may include patient history, virtual 3D models generated from intraoral scan data, or other patient data. Such areas of interest may include areas indicative of tooth wear, areas indicative of tooth decay, areas indicative of receding gums, a gum line, a patient bite, a margin line (e.g., margin line of one or more preparation teeth), and so forth. Areas of interest may also include areas indicative of foreign objects (e.g., studs, bridges, etc.), areas for the dental practitioner to perform planned treatment, or the like. The AOI identifying modules 115 may, in identifying an AOI, analyze patient image data 135. The analysis may involve direct analysis (e.g., pixel-based and/or other point-based analysis), the application of machine learning, the application of image registration, and/or the application of image recognition. The AOI identifying modules 115 may identify areas of interest directly from the image data 135 received from the image capture device 160 or based on a comparison of the received image data 135 and reference data 138 or previous patient data 140. For example, an AOI identifying module 115 may use one or more algorithms or detection rules to analyze the shape of a tooth, color of a tooth, position of a tooth, or other characteristics of a tooth to determine if there is any AOI that should be highlighted for a dental practitioner.

AR display module 118 is responsible for determining how to present and/or call out the identified areas of interest on the AR display 150. AR display module 118 may provide indications or indicators highlighting identified AOIs. The AR display module 118 may determine a position to project a virtual object in a visual overlay on an AR display 150 such that the overlay is positioned in the line of sight of the dental practitioner over the AOI. The virtual object may include text, numbers, a contour, colors, graphical images and/or other virtual objects. For instance, the AR display module 118 may determine from the position of the AOI in the image data 135 a corresponding position to project an indicator or indication on the AR display 150. As an example, the AR display module 118 may provide an indication of wear on a tooth by highlighting the worn area on the tooth in a notable color (e.g., that contrasts with a background on which the indication is superimposed) and/or or by providing an indicator pointing to the tooth. In some embodiments, the AR display 150 may provide additional indicators separate from a position corresponding to the AOI in order to provide additional data to a dental practitioner.

The AR display module 118 may provide the indications in the form of flags, markings, contours, text, images, and/or sounds (e.g., in the form of speech). In some embodiments, the AR display module 118 may provide a contour (e.g., via contour fitting) so as to follow a tooth contour or gingival contour in the image data 135. As an illustration, a contour corresponding to a tooth wear diagnostic assistance indication may be placed so as to follow a contour of the worn tooth. A contour may also follow a previous contour of the tooth or other dental feature. For example, a visual overlay may include a contour showing a previous shape of a tooth, or a difference between a previous shape of a tooth and a current shape of the tooth. Such a contour may be placed in the visual overlay so as to be superimposed over the real-world view of the tooth in question or adjacent (e.g., touching) the tooth in question. As an illustration, a contour corresponding to a previous or future position of a tooth may be displayed so as to follow the projected path of the tooth portion which is missing, or a contour corresponding to missing gingival scan data may be placed so as to follow the projected path of the gingival portion which is missing.

The wearer of the AR display 150 may provide an indication of an identity of the wearer (e.g., through a menu or other user interface). AR processing module 108 may then determine what information to include in the visual overlay based on the identity of the wearer. For example, first information may be shown to a dentist and second information may be shown to a dental hygienist. In some instances, the AR processing module 108 provides a script of actions for the dental practitioner or dental hygienist to perform and/or a script of things to say to the patient. This script may have been input by a dentist, for example. The script may show up as a visual overlay on the AR display 150. The script may be presented to the dental practitioner when particular events occur, such as when a particular dental condition is identified from image data generated by image capture device 160. Additionally, or alternatively, the AR processing module 108 may walk a dentist or dental hygienist through a patient history while the dentist views the patient's mouth. An audio output describing the history may be output to the dentist while one or more areas of interest associated with the dental history are highlighted to the dentist on the AR display 150 via the visual overlay.

In some embodiments, a treatment control module 120 is responsible for determining what data to present on AR display 150 based on an intraoral treatment or procedure of a patient. In some embodiments, the treatment control module 120 may also control one or more dental tools or instruments that are used by a dental practitioner during treatment. This may include powering on the tools, powering off the tools, changing settings of the tools, and so on. The treatment control module 120 may access patient data 140, image data 135, and reference data 138 to determine AR elements to provide on AR display 150. In some embodiments, the treatment control module 120 may receive AOIs from one or more AOI identifying modules 115 or provide data or instructions to one or more AOI identifying modules 115 to direct the AOI identifying modules 115 to identify AOIs relevant to a particular treatment or part of a treatment. The treatment control module 120 may also provide tracking of dental tools or other instruments in the view of image data 135 received from image capture device 160.

In one embodiment, the AR system 100 additionally includes a virtual reality (VR) display 152 that may be worn by a patient. The image data from the image capture device 160 and/or the visual overlay generated based on the image data may be output to the VR display 152. This may enable the patient to view dental conditions of his teeth or gums that a dental practitioner is seeing (and possibly describing). This may facilitate an explanation of the dental conditions to the patient by the dental practitioner. Image data from the image capture device and/or visual overlays may also be sent to the VR display, for example, during dental procedures.

In one embodiment, the patient is provided a control to select one or more viewing modes for the VR display worn by the patient. One viewing mode shows the visual overlay generated by the AR processing module 108. This may include, for example, a virtual 3D model generated based on an intraoral scan while the intraoral scan is being performed. One viewing mode shows the view of the dental practitioner (e.g., the image data from the image capture device of the AR display worn by the dental practitioner) with the visual overlay generated by the AR processing module 108. One viewing mode shows the view of the dental practitioner without the visual overlay. One viewing mode shows entertainment content for the patient, such as movies.

In one embodiment, the AR system 100 includes an intraoral scanner 180. The computing device 105 may be a computing device connected to the intraoral scanner 180 that includes an intraoral scan application 109 for controlling an intraoral scan procedure. The AR display 150 may be an AR display for the intraoral scanner 180.

In one embodiment, the intraoral scanner 180 includes an image sensor, a communication module and one or more inputs (e.g., buttons, a touch sensor, switches, sliders, etc.). The image sensor generates intraoral images of a patient and the communication module transmits those intraoral images to computing device 105. The computing device may then display the intraoral images or a representation of the dental arch of the patient generated from the intraoral images (e.g., a virtual 3D model of a dental site of the patient) via a visual overlay sent to the AR display 150. A user may then use the one or more inputs from the intraoral scanner, motion gestures, or other inputs to manipulate the intraoral images or the representation (e.g., virtual 3-D model) generated from the intraoral images. The intraoral images or virtual 3-D model may be shown in the AR display as they are manipulated.

Intraoral scanner 180 may include a probe (e.g., a hand held probe) for optically capturing three dimensional structures (e.g., by confocal focusing of an array of light beams). Intraoral scanner 180 may also include other components such as optical components, an accelerometer, communication components, a gyroscope, processing devices, and so on. One example of an intraoral scanner 180 is the iTero® intraoral digital scanner manufactured by Align Technology, Inc.

The intraoral scanner 180 may be used to perform an intraoral scan of a patient's oral cavity. Intraoral scan application 109 running on computing device 105 may communicate with intraoral scanner 180 to effectuate the intraoral scan. A result of the intraoral scan may be a sequence of intraoral images that have been discretely generated (e.g., by pressing on a "generate image" button of the scanner for each image). Alternatively, a result of the intraoral scan may be one or more videos of the patient's oral cavity. An operator may start recording the video with the intraoral scanner 180 at a first position in the oral cavity, move the intraoral scanner 180 within the oral cavity to a second position while the video is being taken, and then stop recording the video. The intraoral scanner 180 may transmit the discrete intraoral images or intraoral video to the computing device 105. Computing device 105 may store and/or process the discrete intraoral images or intraoral video in data store 110.

The manner in which the oral cavity of a patient is to be scanned may depend on the procedure to be applied thereto. For example, if an upper or lower denture is to be created, then a full scan of the mandibular or maxillary edentulous arches may be performed. In contrast, if a bridge is to be created, then just a portion of a total arch may be scanned which includes an edentulous region, the neighboring abutment teeth and the opposing arch and dentition. Thus, the dental practitioner may input the identity of a procedure to be performed into the intraoral scan application 109. For this purpose, the dental practitioner may choose the procedure from a number of preset options on a drop-down menu or the like that may be shown via the AR display. The dental practitioner may generate a treatment plan that includes one or more segments that are to be scanned. A segment (or scan segment) may include a particular tooth (e.g., a preparation tooth), an upper or lower arch, a portion of an upper or lower arch, a bite, and so on.

The intraoral scan application 109 may provide a user interface that is shown in the AR display, where the user interface enables the dental practitioner to interact with intraoral scan application 109 through manipulation of graphical elements such as graphical icons and visual indicators such as buttons, menus, and so on while the dental practitioner remains focused on a patient (e.g., without looking away from the patient to a computer monitor). Intraoral scan application 109 may include a number of modes, such as a planning mode, a scan mode, an image processing mode, and a delivery mode. The intraoral scan application 109 may display different graphical elements via the AR display 150 for each of the various modes.

Navigation or control of the user interface of the intraoral scan application 109 may be performed via user input. The user input may be performed through various devices, such as a touch sensor on the intraoral scanner 180, gesture inputs detectable by the intraoral scanner 180, additional input mechanisms on the intraoral scanner 180, and so on. Navigation of the user interface may involve, for example, navigating between various modules or modes, navigating between various segments, controlling the viewing of the 3D rendering, or any other user interface navigation.

Intraoral scan application 109 may include a planning mode that allows a user (e.g., dental practitioner) to generate a patient profile and/or treatment plan for a patient. The patient profile may include information such as patient name, patient contact information, patient dental history, and so on. The treatment plan may include dental procedures to be performed and/or teeth to which the dental procedures are to be performed. Some treatment plans include an indication of specific patient teeth that are to be preparation teeth. Information for the treatment plan may be shown in the AR display during the treatment planning mode.

Once a patient profile and/or treatment plan are generated, intraoral scan application 109 may enter a scan mode. A user may transition from the planning mode to the scan mode by navigating a menu displayed in the AR display 150. The scan mode allows the dental practitioner to capture images and/or video (e.g., for lower arch segment, upper arch segment, bite segment, and/or preparation tooth segments). The images and/or video may be used to generate a virtual 3D model of a dental site. While in the scan mode, intraoral scan application 109 may register and stitch together intraoral images from the intraoral scanner 180 and generate a partial virtual 3-D model of a portion of a dental arch that has been scanned thus far. Intraoral scan application 109 may interface with AR display module 118 to cause AR display module 118 to then generate a virtual overlay that includes the partial virtual 3-D model of the portion of the dental arch. AR display module 118 may determine an appropriate region in a dental practitioner's field of view to project the partial virtual 3-D model, and may generate a virtual overlay with the partial virtual 3-D model at the determined region. This virtual overlay 118 may then be sent to AR display 150, and the dental practitioner 150 may see the progress of the intraoral scan during the scan.

During the scan mode, intraoral scan application 109 may provide the partial virtual 3-D model to one or more of the AOI identifying modules 115. The AOI identifying modules 115 may determine portions of the dental arch that have been scanned. The AOI identifying modules 115 may then determine what areas in image data 135 received from the image capture device 160 associated with the AR display 150 correspond to the already scanned portions of the dental arch. AR display module 118 may then generate a virtual overlay the causes the already scanned portions of the dental arch as viewed by the dental practitioner to be highlighted by superimposing colors over the scanned portions of the dental arch and/or that causes the not yet scanned portions to be highlighted. The visual overlay that is superimposed over portions of the patient's dental arch may be generated instead of or in addition to the visual overlay that provides a virtual 3-D model of the scanned portions of the dental arch.

Once an intraoral scan is complete, intraoral scan application 109 may enter an image processing mode. While in the image processing mode, the intraoral scan application 109 may process the intraoral scan data from the one or more scans of the various segments to generate a virtual 3D model of a scanned dental site.

In one embodiment, intraoral scan application 109 performs image registration for each pair of adjacent or overlapping intraoral images (e.g., each successive frame of an intraoral video). Image registration algorithms are carried out to register two adjacent intraoral images, which essentially involves determination of the transformations which align one image with the other. Image registration may involve identifying multiple points in each image (e.g., point clouds) of an image pair, surface fitting to the points of each image, and using local searches around points to match points of the two adjacent images. Intraoral scan application 109 may repeat image registration for all adjacent image pairs of a sequence of intraoral images to obtain a transformation between each pair of images, to register each image with the previous one. Intraoral scan application 109 then integrates all images into a single virtual 3D model of the dental arch (or portion of the dental arch) by applying the appropriate determined transformations to each of the images. Each transformation may include rotations about one to three axes and translations within one to three planes.

While in the image processing mode, a user may view the virtual 3D model in detail to determine if it is acceptable. Intraoral scan application 109 may invoke AR display module 118 to cause AR display module 118 to generate a virtual overlay that includes the virtual 3D model, which may be sent to the AR display 150. The image processing mode allows the dental practitioner to view the scans in detail at various angles by rotating, moving, zooming in or out, etc. of the virtual 3D model. The dental practitioner may make a determination whether the quality of the scans are adequate, or whether particular segments or portions of segments should be rescanned. The dental practitioner may also navigate back to the scan mode to perform additional scans.

Once the scans are complete, a delivery mode allows the dental practitioner to send the scans and/or virtual 3D model out to an external facility to process the scans or 3D model.

Figure 1B:
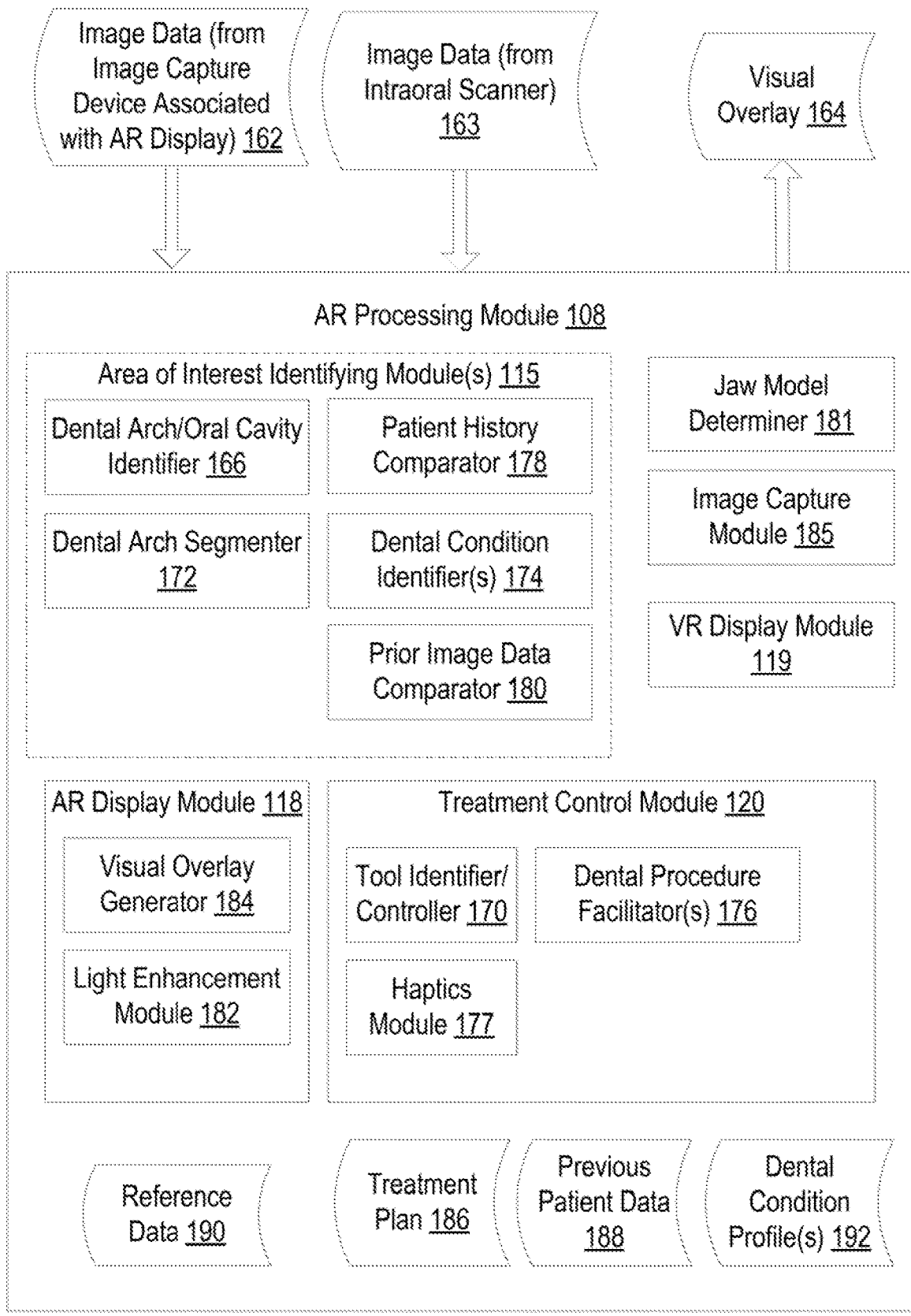
FIG. 1B illustrates one embodiment of an augmented reality processing module, in accordance with an embodiment.

FIG. 1B illustrates one embodiment of an augmented reality processing module 108, in accordance with an embodiment. The AR processing module 108 may correspond to AR processing module 108 of FIG. 1A in embodiments. AR processing module 108 receives as an input image data 162 from image capture device 160 associated with AR display 150, processes the image data 162, and generates a visual overlay 164 that is then output to the AR display 150. The image data 162 preferably includes an image of a patient's oral cavity that includes a dental arch (or two dental arches). AR processing module processes the image data 162 to determine areas of interest, where the areas of interest are areas in the oral cavity (e.g., on the dental arch) that potentially have a clinical significance. For example, the AR processing module 108 may identify possible cavities, tooth discoloration, gum discoloration, tooth cracks, tooth wear, gum recession, oral cancer, and so on. AR processing module 108 generates indicators for the identified areas of interest and adds those indicators to the visual overlay 164. Notably, the image data 162 may represent a real-world scene as viewed by a dental practitioner wearing an AR display. AR processing module 108 may receive the image data 162, process the image data, and output the visual overlay 164 to the AR display in real time or near-real time so that the visual overlay corresponds to the scene that the dental practitioner is currently viewing through the AR display. The AR processing module 108 may receive a stream of image data 162 from the image capture device 160 and may output a stream of the visual overlay 164 that corresponds to the incoming stream of image data 162. Thus the visual overlay 164 may be continually updated in real time or near-real time to maintain correspondence to the scene as viewed by the dental practitioner as a patient moves, the dental practitioner moves, or the scene otherwise changes.

In one embodiment, AR processing module 108 includes multiple AOI identifying modules 115. Alternatively, one or more of these AOI identifying modules 115 may be combined into a single AOI identifying module 115. Each AOI identifying module 115 is configured to identify particular types of information from the image data and/or particular AOIs for flagging from the image data. For example, AOI identifying modules 115 may identify an image of a tooth, dental arch, or other dentition feature in the image data 162. In some embodiments, all of AOI identifying modules 115 are implemented to identify AOIs using a variety of techniques. In other embodiments, AR processing module 108 may include a subset of the AOI identifying modules 115 using a subset of the AOI identifying techniques described herein. For example, the AR processing module 108 may include a dental arch/oral cavity identifier 166, a dental arch segmenter 172 and one or more dental condition identifiers 174, but may lack a prior data comparator 180.

Dental arch/oral cavity identifier 166 may be responsible for identifying an oral cavity in received image data 162 and for identifying a dental arch in the oral cavity. To identify the oral cavity, dental arch/oral cavity identifier 166 performs image processing on the image data 162 using image recognition techniques. For example, oral cavities have visual cues that can be used to pinpoint the oral cavities in the image data 162. Dental arch/oral cavity identifier 166 may include an oral cavity profile that may have been generated using machine learning techniques such as neural networks. Processing the image data 162 may include first pre-processing the image data such as by performing re-sampling in a new coordinate system, performing noise reduction, enhancing contrast, adjusting scale, etc. Processing the image data 162 may additionally include performing feature extraction to identify lines, edges, ridges, point clouds, corners, point blobs, and so on. Processing the image data 162 may additionally include performing detection and/or segmentation to select those lines, edges, ridges, point clouds, corners, point blobs, etc. that represent the oral cavity and/or objects within the oral cavity.

Dental arch/oral cavity identifier 166 can identify the dental arch (or multiple dental arches) in the oral cavity using similar techniques as described for identifying the oral cavity. However, a dental arch profile may be used to identify the dental arch.

In an example, dental arch/oral cavity identifier 166 may identify features in the image data based on geometric analysis of the image data 162. The dental arch/oral cavity identifier 166 may perform geometric analysis based on identification of lines or color blobs in the image data 162. The geometric analysis may identify the features of an oral cavity and/or the features of a dental arch.

Dental arch segmenter 172 may be responsible for segmenting an identified dental arch into individual teeth. The dental arch segmenter 172 may operate on similar principles as the dental arch/oral cavity identifier. Dental arch segmenter 172 may receive a subset of image data 162 that has already been processed by dental arch/oral cavity identifier 166 (e.g., point blobs, contours, ridges, corners, point clouds, etc. that represent a dental arch), and may perform detection and segmentation to segment the dental arch into the individual teeth. Dental arch segmenter 172 and/or dental arch/oral cavity identifier 166 may additionally identify gums in the oral cavity represented in the image data 162 and separate the gums from the teeth.

The AOI identifying modules 115 additionally include one or more dental condition identifiers 174. Each dental condition identifier 174 may be responsible for identifying a particular dental condition in the oral cavity of the patient from the image data 162 using one or more rules (that may include algorithms, models and/or profiles) that are tailored to detection of that particular dental condition. Alternatively, a single detection rule or set of rules (e.g., that may include algorithms, models and/or profiles) may be used to detect multiple different types of dental conditions. The dental condition identifiers 174 may operate on the original unprocessed image data 162 or may operate on processed image data that has been processed by the dental arch/oral cavity identifier 166 and/or the dental arch segmenter 172. For example, one dental condition identifier 174 may be a broken tooth identifier, which may separately perform broken tooth identification for each tooth identified by dental arch segmenter 172. Examples of dental condition identifiers 174 include a broken tooth identifier, a plaque identifier, a tooth wear identifier, an oral cancer identifier, a gum discoloration identifier, a tooth discoloration identifier, a malocclusion identifier, a gum recession identifier, a swollen gum identifier, and so on.

In some embodiments, one or more dental condition identifier 174 use image data generated after light having a specified wavelength is used to illuminate the dental arch. The dental condition identifier 174 may send an instruction to one or more light sources (not shown) that may be mounted to the AR display 150 or may be separate from the AR display 150. The light sources may emit ultraviolet light, infrared radiation, or other wavelength radiation. The dental condition identifier 174 may process the image data generated during such illumination of the dental arch to determine additional information relevant to a particular dental condition. The specific wavelength may improve detection of the particular dental condition.

In some embodiments, one or more of the dental condition identifiers 174 performs a color analysis of the image data to identify a dental condition.

In some embodiments, the dental condition identifiers 174 may apply rules (e.g., including algorithms, models and/or profiles) that compare dentition features (also referred to as dental features) from a received image to reference data 190, which may include a store of dentition features. The reference data 190 may include elements comprising models or images of dentition features. In some embodiments, the reference data 190 may have other representations of dentition features. The elements in reference data 190 may have AOIs associated with the dentition features. For example, a model of a tooth with a crack may be stored in the reference data 190 with an associated indicator that the particular tooth had a crack. In some embodiments, the dental condition identifier 174 may extract a model, image, set of edges, a point blob, set of contours, and/or other representation of a dentition feature from the image data 162. The dental condition identifier 174 may then compare the extracted model, set of edges, point blob, set of contours, image or other representation of a dentition feature to a data store of similar dentition features. A most similar stored dentition feature may be selected based on a point by point comparison, edge comparison, or other comparison of the extracted feature representation to the representations of dentition features in the data store. The dental condition identifier 174 may then determine that the extracted dentition feature has the same AOIs present in the most similar stored dentition feature.

In some embodiments, the dental condition identifiers 174 may perform analysis of a dentition feature using machine learning algorithms. For example, a dental condition profile 192 may be trained based on reference data 190 to correlate dentition features in the reference data 190 with associated clinical diagnosis of AOIs. The dental condition identifier 174 may then provide an image or an extracted representation of a dentition feature to the dental condition profile 192 and receive an indication of potential AOIs. In some embodiments, the dental condition identifier 174 may perform additional analysis to confirm the AOIs identified by a dental condition profile.

In some embodiments, dental condition identifiers 174 may use a dental condition profile 190 that has been trained using machine learning techniques to identify a particular dental condition. A dental condition profile 192 may be trained by extracting contents from a training data set and performing machine-learning analysis on the contents to generate a classification model and a feature set for the particular dental condition. Each dental condition profile may be or include a tailored algorithm for identifying a particular type of dental condition or multiple different types of dental conditions. The training data set includes positive examples of a dental condition (e.g., images in which the dental condition is present such as images of broken teeth) and negative examples that lack the dental condition (e.g., images of unbroken teeth). To generate the classification model and feature set for a dental condition profile, the positive examples of the dental condition and the negative examples of the dental condition in the training data set are analyzed to determine the frequency of occurrence of features (e.g., particular arrangements of point clouds, edges, contours, point blobs, etc.) in the positive examples and in the negative examples. Positive features and negative features may then be ranked based on, for example, frequency of occurrence in the positive examples and negative examples. These features make up a feature set for the dental condition profile 192. The classification model for the dental condition profile 192 is generated based on the feature set and the training data set. The classification model is a statistical model for data classification that includes a map of support vectors that represent boundary features. The boundary features may be selected from the feature set, and may represent the highest ranked features in the feature set.

A dental condition identifier 174 applies the received image data 162 or processed portion of the image data 162 (e.g., features such as point blobs, contours, edges, corners, etc. that represent a tooth) to an appropriate dental condition profile 192. Based on the application of the image data 162 or features of the images data 162 to the dental condition profile 192, the dental condition identifier 174 classifies the image data or features as having the dental condition or not having the dental condition. The dental condition identifier 174 also determines a contour of the dental condition in the image data 162. This may include identifying a contour of a crack, identifying a contour of a worn portion of a tooth, identifying a contour of a discolored gum area, identifying a contour of a possible oral cancer, and so on. The contour may represent an intraoral area of interest to call to the attention of a dental practitioner. In addition, the dental condition identifier determines a confidence level for the determined classification. If the confidence value for the dental condition is 100%, then it is more likely that the decision that the dental condition is present (or not present) is accurate than if the confidence value is 50%, for example.

One example dental condition identifier is a gum recession identifier. The gum recession identifier may detect gum recession by analyzing a distance between a patient's gum line and the crowns of one or more teeth of a patient. The gum line may be determined by dental arch/oral cavity identifier 166 or the gum recession identifier. For example, the dental arch/oral cavity identifier 166 may use a dental arch profile to identify and delineate a dental arch, including the gum line of the dental arch. Alternatively, the gum recession identifier may use a gum line profile that specifically identifies a contour of a gum line. The tooth contours may be determined by the dental arch segmenter 172 or gum recession identifier.

Once the gum line and the tooth contours are determined, a vector from the crown of a tooth to the gum line may be determined for one or multiple teeth. The vector may be positioned at the center of the crown and may point in a direction towards the gum line that causes the vector to approximately bisect the tooth. Vectors may be determined for multiple teeth that are visible in the received image data 162. The magnitude of the vectors may be compared to an average gum recession value. The average gum recession value may be based on a patient's age. If the magnitude of a vector exceeds the average gum recession value for the patient's age, then the gum recession area (e.g., the gum line where the gum recession is identified) may be indicated as an area of interest. Additionally, the variance between the magnitude of the vector and the gum recession value may be called out in the visual overlay.

In some embodiments, the AOI identifying modules 115 additionally include a prior data comparator 180. The prior data comparator 180 may identify one or more areas of interest by comparing image data 162 to prior image data included in previous patient data 188. Patient data 188 may include past data regarding the patient (e.g., medical records), previous or current scanned images or models of the patient, current or past X-rays, 2D intraoral images, 3D intraoral images, virtual 2D models, virtual 3D models, or the like.

Prior data comparator 180 may perform image registration between the image data 162 and the prior image data of a patient's oral cavity, dental arch, individual teeth, or other intraoral regions. Image registration algorithms are carried out to register the current image data 162 from the image capture device of the AR system to one or more previous images of a patient's mouth, dental arch, teeth, etc. The image registration involves determination of the transformations which align one image with the other. Image registration may involve identifying multiple points, point clouds, edges, corners, etc. in each image of an image pair, surface fitting to the points of each image, and using local searches around points to match points of the two images. For example, prior data comparator 180 may match points of one image with the closest points interpolated on the surface of the other image, and iteratively minimize the distance between matched points. Prior data comparator 180 may also find the best match of curvature features at points of one image with curvature features at points interpolated on the surface of the other image, with or without iteration. Prior data comparator 180 may also find the best match of spin-image point features at points of one image with spin-image point features at points interpolated on the surface of the other image, with or without iteration. Other techniques that may be used for image registration include those based on determining point-to-point correspondences using other features and minimization of point-to-surface distances, for example. Other image registration techniques may also be used.

Many image registration algorithms perform the fitting of a surface to the points in adjacent images, which can be done in numerous ways. Parametric surfaces such as Bezier and B-Spline surfaces are common, although others may be used. A single surface patch may be fit to all points of an image, or alternatively, separate surface patches may be fit to any number of a subset of points of the image. Separate surface patches may be fit to have common boundaries or they may be fit to overlap. Surfaces or surface patches may be fit to interpolate multiple points by using a control-point net having the same number of points as a grid of points being fit, or the surface may approximate the points by using a control-point net which has fewer number of control points than the grid of points being fit. Various matching techniques may also be employed by the image registration algorithms.

In one embodiment, prior data comparator 180 may determine a point match between images, which may take the form of a two dimensional (2D) curvature array. A local search for a matching point feature in a corresponding surface patch of another image is carried out by computing features at points sampled in a region surrounding the parametrically similar point. Once corresponding point sets are determined between surface patches of the two images, determination of the transformation between the two sets of corresponding points in two coordinate frames can be solved. Essentially, an image registration algorithm may compute a transformation between two images that will minimize the distances between points on one surface, and the closest points to them found in the interpolated region on the other image surface can be used as a reference. The transformation may include rotations and/or translational movement in up to six degrees of freedom (e.g., rotations about one to three axes and translations within one to three planes). Additionally, the transformation may include changes in image size (e.g., zooming in or out) for one or both of the images. A result of the image registration may be a transformation matrix that indicates the rotations, translations and/or size changes that will cause the one image to correspond to the other image. In one embodiment, the transformation matrix is applied to the prior image data to cause the prior image data to correlate with the current image data 162.

In some instances, the previous image data to which the current image data 162 is registered comprises a three dimensional model of a patient's dental arch and/or jaw. The three dimensional model may have been generated at a previous time based on an intraoral scan of the patient's upper and/or lower dental arches. The three dimensional model may include the upper and lower dental arches, and may reflect articulation of a patient's jaw and tooth contact points between the upper and lower dental arch. To register the image data 162 to the three dimensional model, prior data comparator 180 may digitally construct multiple images of the three dimensional model from different perspectives. If the image data is two-dimensional image data, then each of the digitally constructed images may be two-dimensional images. Prior data comparator 180 may then attempt to register each of the digitally constructed images to the current image data 162 until registration is successful for one of the digitally constructed images. The perspective used to generate the registered digitally constructed image to the image data 162 is known, and so the three dimensional model may be registered to the image data 162.

Once the prior image data has been registered to the current image data 162 and transformed to match the current image data 162 as closely as possible, the transformed previous image data (or a portion thereof) may be used to generate visual overlay 164. Accordingly, a patient's historical dentition as represented in the previous image data may be adjusted to a current view point of a dental practitioner wearing an AR display, and the visual overlay showing the patient's historical dentition may be superimposed over the current view of the dental practitioner.

In one embodiment, once prior image data from previous patient data 188 has been registered to the current image data 162 and transformed accordingly, prior data comparator 180 compares the two images to determine differences between the prior image data and the current image data 162. This may include performing any of the aforementioned image recognition techniques to identify features in the previous image data and corresponding features in the current image data. For example, prior data comparator 180 may invoke dental arch/oral cavity identifier 166 and/or dental arch segmenter 172 to identify a dental arch, individual teeth, a gum line, gums, etc. in the current image data 162 and previous image data. Differences between the two images may be determined, and prior data comparator 180 may generate contours of those differences. In one example, a difference between the two images for a tooth may include tooth wear reflected in the current image data 162 that is not shown in the previous image data. In other examples, differences may include gum discoloration, tooth decay, tooth discoloration, gum recession, etc. that are shown in the current image data 162 but not in the previous image data. Prior data comparator 180 may mark the contours of the differences between the images as areas of interest.

In one embodiment, the prior data comparator 180 identifies a feature in the image data 162 to use to correlate the image data to the previous image data. The feature may be a portion of a tooth, a gum line, a specific tooth, or any feature of a dental arch. The prior data comparator 180 may then compare the feature in the dental arch of the image data 162 to the feature as represented in previous data associated with the dental arch. For example, if the feature is a tooth, the prior data comparator 180 may compare the tooth in the image data to the tooth in previous patient data. The prior data comparator 180 may then determine if there has been excessive wear on the tooth, movement of the tooth, color change of the tooth, or other clinical determinations of change to the tooth. Additionally, prior data comparator 180 may determine whether an attachment was previously attached to a tooth but is no longer attached to the tooth (e.g., was lost). Additionally, prior data comparator 180 may determine whether an attachment has moved out of position (e.g., currently has a different position than it had when initially placed). If there has been a change, the prior data comparator 180 may identify the change as an area of interest. In some embodiments, the prior data comparator 180 may also identify AOIs based on features previously marked in patient history or by the dental practitioner.

In many instances, the prior image data will be stamped with a date and/or time. Additionally, a current date and/or time may be determined. Prior data comparator 180 may determine a magnitude of a change in a dental condition based on the determined differences between the current image data 162 and the previous image data. Additionally, prior data comparator may model a rate or change of the dental condition based on the magnitude of the difference. The accuracy of the modeled rate of change may be improved if the previous patient data includes previous image data from multiple previous time periods.

Prior data comparator 180 may compare the determined magnitude of change and/or the determined rate of change of the dental condition to general norms for the dental condition. The general norms may include rate of change thresholds for the dental condition. If the determined rate of change exceeds a rate of change threshold, then prior data comparator 180 may generate a notice or flag for the dental practitioner calling out an abnormal change in the dental condition.

In one embodiment, AR processing module 108 includes a jaw model determiner 181. Jaw model determiner 181 may be invoked to determine the articulation of a patient's jaw. When jaw model determiner 181 is invoked, it may notify a dental practitioner to instruct a patient to move his or her lower jaw through multiple extremes of motion, to move his or her face to multiple different positions, to smile, to open his or her mouth, etc. This may include moving the lower jaw to the left as much as possible, moving the lower jaw to the right as much as possible, opening the mouth as far as possible, jutting the lower jaw forward as far as possible (e.g., to cause an under bite), and positioning the lower jaw as far back as possible (e.g., to cause an over bite). This may also include moving the patient's head to the left to show a left profile view of the patient's face (with the mouth open and/or closed), moving the patient's head to the right to show a right profile view of the face (with the mouth open and/or closed), looking up, looking down, and so on.

The image capture device 160 may generate a stream of images while the patient moves his or her jaw through the extremes of motion or position extremes. Jaw model determiner 181 may determine from the stream of images those images that represent each of the motion or position extremes. For example, jaw model determiner 181 may determine a left profile view with the patient's mouth closed, a left profile view with the patient's mouth open, a right profile view with the patient's mouth closed, a right profile view with the patient's mouth open, a front view with the patient's mouth closed, a front view with the patient's mouth open (e.g., smiling), a view in which the mouth is opened as far as possible, a view in which the lower jaw is moved to the right as much as possible, a view in which the lower jaw is moved to the left as much as possible, and so on.

Based on the jaw motion extremes and/or position extremes, jaw model determiner 181 may generate an articulation model for the patient's jaw that defines motion vectors for the jaw. Alternatively or additionally, jaw model determiner 181 may generate another model of the jaw, such as a cephalographic model of the jaw and patient's head. The articulation model may be used along with a 3-D model of the patient's upper and lower arches to identify functioning contacts and interfering contacts between teeth in the upper arch and teeth in the lower arch. The articulation model may be used to track the movement of the jaw on vectors defined by the articulation model. Contacts between the teeth of the upper arch and the teeth of the lower arch may be determined for different types of jaw motion such as shear movements, up and down movements, etc. These contact points may be used to generate an occlusion map of the upper dental arch and lower dental arch.

In some instances, prior image data may include AOIs that have been marked in the prior image data by a dental practitioner. In such instances, the AOIs from the prior image data may be included in the visual overlay at an appropriate location to call the dental practitioner's attention to the AOIs.

Prior data comparator 180 may additionally determine AOIs based on an analysis of prior patient data other than prior image data of the patient. For example, a clinical history for a patient might state that a particular procedure was performed on a specified tooth, that a specified tooth in a concern, or provide other information about the patient's dentition. Prior data comparator 180 may determine which tooth in the image data 162 is referenced in the prior patient data, and may generate an indicator for an AOI corresponding to that tooth. In an example, prior data comparator 180 may graphically walk the dental practitioner through a patient history, highlighting areas referenced in the patient history using the visual overlay 164. Prior data comparator 180 may also provide an audio output describing the patient history.

One type of patient data that the image data 162 may be compared to is an orthodontic treatment plan. The orthodontic treatment plan may include a sequence of orthodontic treatment stages. Each orthodontic treatment stage may adjust the patient's dentition by a prescribed amount, and may be associated with a 3-D model of the patient's dental arch that shows the patient's dentition at that treatment stage. Additionally, images of the patient's dentition may be generated at each treatment stage.

Prior data comparator 180 may compare the current image data 162 to prior images taken of the dental arch during previous orthodontic treatment stages. Additionally, or alternatively, the current image data 162 may be compared to a 3-D model of the dental arch for the current treatment stage and/or one or more previous treatment stages of the orthodontic treatment plan. Based on the comparison of the current image data 162 to the 3-D model (or models) of the orthodontic treatment plan, progress of orthodontic treatment may be determined. Teeth movement progress may then be shown virtually in the visual overlay 164 that is provided to the AR display 150. Additionally, or alternatively, an indication of whether an action should be performed to continue orthodontic treatment may be determined, and the action may be suggested via the visual overlay 164.

Additionally, the current image data 162 may be compared to a final orthodontic position (new arrangement of teeth) associated with a final treatment stage or other future orthodontic position associated with another future intermediate treatment stage. Based on this comparison, a visual overlay showing the final arrangement or other future arrangement of the teeth may be generated. Accordingly, the dental practitioner may be able to see what the patient will look like with his or her future or final tooth arrangement.

AR display module 118 is responsible for determining how to present and/or call out the identified areas of interest on the AR display 150. AR display module 118 may provide indications or indicators highlighting identified AOIs. In one embodiment, AR display module 118 includes a visual overlay generator 184 that is responsible for generating the visual overlay 164 that is superimposed over a real-world scene viewed by a dental practitioner. The visual overlay generator 184 may determine a visual overlay for an AOI identified by one or more of the AOI identifying modules 115, and may determine a position to project the visual overlay 164 on an AR display 150 such that the visual overlay is positioned in the line of sight of the dental practitioner over the AOI in the real-world scene viewed by the dental practitioner. For instance, the visual overlay generator 184 may determine from the position of the AOI in the image data 162 a corresponding position to project an indicator or indication on the AR display 150. As an example, the visual overlay generator 184 may provide an indication of wear on a tooth by highlighting the worn area on the tooth in a different color or by providing an indicator pointing to the tooth. In some embodiments, the AR display module 118 may also provide additional indicators separate from a position corresponding to the AOI in order to provide additional data to a dental practitioner.

The AR display module 118 may provide the indications in the form of flags, markings, contours, text, images, and/or sounds (e.g., in the form of speech). In some embodiments, the AR display module 118 may provide a contour (e.g., via contour fitting) so as to follow a tooth contour or gingival contour in the image data 162. As an illustration, a contour corresponding to a tooth wear diagnostic assistance indication may be placed so as to follow a contour of the worn tooth.

In placing indications, AR display module 118 may or may not take into account factors to avoid crowding the display. For instance the AR display module 118 may display only one AOI on each portion of AR display 150 or only a set number of AOI indicators on the AR display as a whole. In some embodiments, the AR display module 118 may take into account available lighting, available angle, or other factors corresponding to user viewing of the teeth and/or gingiva depiction, and may position indicators to optimize the viewing for the dental practitioner. For example, the AR display module 118 may place indicators such that they are not obstructing the view of the mouth or portion of a mouth of a patient.

The AR display module 118 may key the indications (e.g., via color, symbol, icon, size, text, and/or number). The keying of an indication may serve to convey information about that indication. The conveyed information may include classification of an AOI, a size of an AOI and/or an importance rank of an AOI. Accordingly, different flags or indicators may be used to identify different types of AOIs. For example, pink indicators may be used to indicate gingival recession and blue indicators may be used to indicate tooth wear. AR display module 118 may determine a classification, size and/or importance rank of an AOI, and may then determine a color, symbol, icon, text, etc. for an indicator of that AOI based on the classification, size and/or importance rank.

Turning to keying which conveys indication size, the processing logic may, in implementing such size-oriented keying, employ one or more size thresholds. The origin of the thresholds may be set (e.g., by a dental expert) during a configuration operation and/or may be preset. In some implementations, the thresholds may be set based on previous patient data 188 or reference data 190. In some treatments, larger size of an AOI may be indicative of greater clinical importance. For example, a large crack in a tooth may be worse than a small crack in a tooth. Similarly, a large amount of tooth wear or gum recession may be more critical than a small amount of tooth wear of gum recession. Furthermore, a small area of wear may be less important than a large area of wear. As an illustration, three thresholds might be set with respect to a type of AOI. Implementation may be such that indications falling into the largest of the three size thresholds are keyed red and/or with the numeral "1," that indications falling into the smallest of the three size thresholds are keyed purple and/or with the numeral "3," and/or that indications falling into the middle-sized of the three thresholds are keyed yellow and/or with the numeral "2."

Turning to keying which conveys AOI classification, indicators may identify classifications assigned to intraoral areas of interest. For examples, AOIs may be classified as tooth wear, tooth cracks, tooth positions, gum recession, gingivitis, plaque, or other types of AOI. AOIs representing changes in patient dentition may represent tooth decay, receding gums, tooth wear, a broken tooth, gum disease, gum color, moles, lesions, tooth shade, tooth color, an improvement in orthodontic alignment, degradation in orthodontic alignment, and so on. Different criteria may be used for identifying each such class of AOI. For example, a change in orthodontic alignment may be identified based on a planned orthodontic treatment, while tooth wear may be identified by an unnatural shape of a tooth.

In some embodiments, AR display module 118 includes a light enhancement module 182 that can improve the visibility of regions of an image within an oral cavity. The light enhancement module 182 can then generate light enhancement effects that improve the visibility of a real-world oral cavity viewed by a dental practitioner. These light enhancement effects can be particularly beneficial during low light conditions.

Light enhancement module 182 may receive an indication of the oral cavity in the image data 162 from dental arch/oral cavity identifier 166. Light enhancement module 182 may then apply a darkening effect to all regions outside of the oral cavity. For example, light enhancement module 182 may add a visual overlay 164 that includes dark pixels with transparency. That way, regions outside of the oral cavity will appear dark to a dental practitioner when viewed through the AR display. Additionally, or alternatively, light enhancement module may apply light enhancing effects to the region inside of the identified oral cavity. By brightening the regions in the oral cavity and/or darkening the regions outside of the oral cavity, a dental practitioner's view of the oral cavity may be improved. The human eye automatically dilates or contacts the pupil to adjust for a total amount of light entering the eye. Additionally, the human eye automatically performs a white balance based on the environment viewed by an eye. Light enhancement module 182 takes advantage of these phenomena by adjusting the total amount of light and the total colors that a dental practitioner wearing an AR display sees. Thus, even without actually adding more light to a patient's mouth, the light enhancement module 182 may improve a dental practitioner's ability to view the oral cavity by reducing the overall light seen by the eye and increasing the relative amount of light that is caused by regions inside of the oral cavity vs. regions outside of the oral cavity.

In one embodiment, the light enhancement module 182 determines whether a dental practitioner wearing the AR display is focused on (e.g., looking at) the patient's oral cavity. The AR display may include an additional image capture device to track the dental practitioner's eye movement, and the determination of whether the dental practitioner is focused on the patient's oral cavity may be based on a direction of the eyes in relation to a location of the oral cavity in the image data 162. Alternatively, the light enhancement module 182 may determine that the dental practitioner is focused on the oral cavity if an oral cavity is identified to be near a center of the image. Alternatively, the light enhancement module 182 may determine that the dental practitioner is focused on the oral cavity if an oral cavity is detected anywhere in the image data 162. Light enhancement module 182 may apply the light enhancement effects while the dental practitioner is focused on the patient's dental cavity. The light enhancement effects may then disappear once the dental practitioner stops focusing on the patient's oral cavity (e.g., looks away from the patient).

In some embodiments, a light source may be placed inside of a patient's oral cavity. The light source may be a light emitting diode (LED), an incandescent light, a halogen light, or other type of light. The light source may help to illuminate the patient's oral cavity during a dental procedure. However, the light source may cause glare that may blind the dental practitioner. Accordingly, in embodiments light enhancement module 182 may generate a visual overlay 164 that blocks a brightness of the light source. For example, the light source may emit light at a particular wavelength or wavelengths. The light enhancement module may generate a visual overlay 164 that acts as a filter to at least partially filter out particular wavelengths of light. Thus, the light source may illuminate the patient's oral cavity without blinding, or causing glare for, the dental practitioner.

In some embodiments, AR processing module 108 provides a visual overlay 164 during a dental procedure that facilitates that dental procedure. Any type of dental procedure can be facilitated by AR processing module 108. Examples of dental procedures that might be facilitated include grinding of an interproximal area between teeth (e.g., to make room for orthodontic treatment), grinding of a tooth into a stump (e.g., to enable a cap to be placed over the tooth), grinding of a crown of a tooth (e.g., to improve contact points between an upper and lower dental arch), an intraoral scan, drilling of a tooth (e.g., for a root canal or to place an implant anchor), and so on. Many other types of procedures for dentistry and orthodontics may also be improved by the AR processing module.

In some embodiments, a treatment control module 120 is responsible for determining what data to present on AR display 150 based on a treatment of a patient (e.g., a dental procedure performed on the patient). In some embodiments, the treatment control module 120 may also control one or more dental tools or dental instruments that are used by a dental practitioner during treatment. The treatment control module 120 may access previous patient data 188, image data 162, and/or reference data 190 to determine AR elements to provide on AR display 150. In some embodiments, the treatment control module 120 may receive AOIs from AOI identifying modules 115 or provide data or instructions to AOI identifying modules 115 to direct the AOI identifying modules 115 to identify AOIs relevant to a particular treatment or part of a treatment. The treatment control module 120 may also provide tracking of dental tools or instruments in the image data 162 received from image capture device 160.

In some embodiments, a treatment control module 120 may determine a treatment or procedure that is being performed by a dental practitioner. The treatment or procedure may be identified based on input from the practitioner such as in a user interface of the AR display 150 or another user interface. In some embodiments, the treatment or procedure may be identified from patient data 140 indicating a reason for a current appointment with the dental practitioner. The treatment or procedure may also be selected by a dental practitioner based on recommendations or indications provided on the AR display 150 by AR display module 118 during an examination or treatment. The treatment control module 120 may access reference data 190 to determine particular AOIs to flag during the identified treatment or procedure and/or other graphics (e.g., simulated objects) to display. For example, if the treatment control module 120 determines that an implant is to be inserted onto the patient's dental arch, the treatment control module 120 may determine steps of the procedure and simulated objects to provide at different steps of a dental implant procedure. As an illustration, the treatment control module 120 may determine that the procedure includes a drilling step and that an indication of a target drill direction and depth is to be displayed.

The treatment or procedure may also be identified based on specific applications executing on the computing device, such as intraoral scan application 109. For example, the intraoral scan application 109 may interface with the AR processing module 108 during an intraoral scan procedure. Based on this interaction, AOI identifying modules 115 may determine areas of interest associated with scanned portions and/or unscanned portions of a dental arch. Additionally, treatment control module 120 may provide feedback for facilitating control of the intraoral scan procedure. Additionally, AR display module 118 may generate appropriate visual overlays to output to an AR display during the intraoral scan procedure.

During treatment, the treatment control module 120 may identify an AOI or receive an indication of an AOI from AOI identifying modules 115. For example, the AOI identifying modules 115 may provide image data, a model, a contour of an AOI, or other representation of an AOI to treatment control module 120. In some embodiments, the treatment control module 120 may identify AOIs for a particular treatment or procedure based on image analysis of image data 162. The treatment control module 120 may also instruct one or more of the AOI identifying modules 115 to identify a particular AOI or type of AOI based on the treatment or procedure. As the dental practitioner performs a treatment or procedure, the treatment control module 120 may receive updated image data, models, or representations of the AOI. The treatment control module 120 may then identify a change to the AOI based on the new data. For example, if the procedure is for an interproximal reduction, the treatment control module may identify a reduction in the size or shape of a tooth being ground based on the new data. The treatment control module 120 may then instruct the AR display module 118 to generate an updated visual overlay 164 for the AR display based on the change. For example, in an interproximal reduction procedure, an area of a tooth to be ground may be highlighted (e.g., superimposed over the tooth in the AR display) using a first color, and a new color may be superimposed onto the AR display 150 when a threshold amount of material has been removed from the tooth to indicate to the dental practitioner that the appropriate amount of material has been removed.

In some embodiments, the treatment control module 120 may also control one or more tools or instruments used by a dental practitioner. For example, during a drilling procedure, the treatment control module 120 may lock use of the drill (or turn off the drill) if the drill is not in the right position or has already drilled to a planned or recommended depth. The treatment control module 120 may additionally or alternatively power on or off the drill (or other dental tool) based on a position and/or orientation of the drill (or other dental tool). The treatment control module 120 may additionally or alternatively control other settings of a drill or other dental tool based on the position and/or orientation of the drill or other dental tool as determined from the image data 162. For example, an intensity setting for a laser drill may be adjusted based on the position and/or orientation of the laser drill. Similarly, in an interproximal reduction procedure, the treatment control module 120 may cause a grinding tool to stop grinding if a planned amount of material has been removed.

In one embodiment, treatment control module 120 includes a tool identifier/controller 170 and/or one or more dental procedure facilitators 176. Each dental procedure facilitator 176 may be responsible for assisting a particular type of dental procedure or intraoral treatment. For example, the dental procedure facilitators 176 may include an intraoral scan facilitator that facilitates intraoral scanning, a dental drilling facilitator that facilitates dental drilling, a tooth grinding facilitator that facilitates tooth grinding (e.g., for interproximal reduction, generating a preparation tooth, improving a patient bite, etc.), an orthodontic treatment facilitator for facilitating one or more aspects of an orthodontic treatment, a dental attachment facilitator, an implant insertion facilitator, and so on.

Each dental procedure facilitator 176 may perform different operations based on the dental procedure to be performed. Details about a particular dental procedure for a particular patient may be included in a treatment plan 186 and/or previous patient data 188. The treatment plan 186 may indicate the procedure to be performed, the tooth or other area on which the treatment is to be performed, and/or one or more other parameters of the dental procedure. The dental procedure facilitator 176 may process the treatment plan 186 and the image data 162 to determine graphics to embed in the visual overlay 164 for facilitating the dental operation. Such graphics may include graphics indicating tooth material to be removed, an area to be drilled, a location on a tooth to place an attachment, and so on. Such graphics may additionally or alternatively indicate an ideal position and/or orientation for a dental tool to perform a dental procedure such as drilling or grinding. Graphics showing the ideal position/orientation for a dental tool may be used by moving the dental tool until the dental tool as seen by the dental practitioner through the AR display is collocated with the graphical indication for the position and orientation in the AR display. Graphics may additionally or alternatively indicate an insertion path for an implant, cap or bridge. These graphics may be added to the visual overlay 164 and superimposed over a view of an oral cavity as seen by a dental practitioner through an AR display. Some example dental procedures and the operations performed to facilitate those dental procedures using augmented reality are described below with reference to FIGS. 20-22.

One example dental procedure facilitator 176 is an insertion facilitator. The insertion facilitator may perform operations to facilitate insertion of a crown or bridge onto a dental arch. The insertion facilitator may compute an optimal insertion path for the crown or bridge based on the geometries of surrounding teeth. This may include determining an angle and direction of the insertion path. Alternatively, the insertion path may be specified in a treatment plan that has already been generated. Based on the insertion path, the insertion facilitator determines a shape for one or more prep tooth on which the crown or bridge will be placed along with the insertion path. Insertion facilitator then marks or highlights the portions of the tooth or teeth to be ground to create the prep tooth that will have the determined shape. The insertion facilitator may mark the reduction space for a crown or bridge in both the occlusion direction and an adjacent (proximal) direction. Once the one or more prep teeth are created, the insertion path may be shown in the visual overlay.

One example dental procedure facilitator is an undercut reduction facilitator. The undercut reduction facilitator may determine teeth with undercuts. The undercut facilitator may then highlight the portions of those teeth with undercuts that are causing the undercuts. These highlights may be shown as a colored visual overlay in the shape of the undercut regions that is shown on the AR display. A dental practitioner may then grind down the highlighted area of the teeth the remove the undercuts.

One example dental procedure facilitator is a cavity drilling facilitator. The cavity drilling facilitator may show an outline and/or highlight of a cavity to be drilled, and indicate whether all of the cavity has been removed (e.g., by marking cavity areas with a first color and healthy areas with a second color). The cavity drilling facilitator may also show drill positions and orientations to remove the cavity.

One example dental procedure facilitator is an occlusion treatment facilitator. Occlusion refers to the contact between teeth. More particularly, occlusion is the relationship between the maxillary (upper) teeth and the mandibular (lower) teeth, such as during chewing. A malocclusion is the misalignment of the teeth and/or jaw that impairs a person's bite. Contacts between maxillary teeth and mandibular teeth may be divided into functional contacts and interfering contacts. An occlusion map as generated by jaw model determiner 181 may show functional contacts using a first color and interfering contacts using a second color. This occlusion map may be registered to the dental arch shown in the image data 162. Thus, functional contacts and interfering contacts may each be highlighted in a visual overlay shown on the AR display 150. A dental practitioner may grind down teeth at the interfering contacts to improve the patient's occlusion (e.g., to eliminate a malocclusion). As the tooth is ground, new image data may be received in real time or near real time from the image capture device. The new image data may be used to compute a new occlusion map, and an updated visual overlay showing the new occlusion map may be projected onto the AR display 150 to overlay the new occlusion map over the dental practitioner's view of the dental arch.

One example dental procedure facilitator is an interproximal reduction (IPR) facilitator. The IPR facilitator may mark the portions of teeth in the interproximal area between the teeth that is to be removed via the visual overlay. As the teeth are ground, new image data may be received in real time or near-real time, and the markings showing the interproximal area to be removed may be updated based on the new image data. The new markings may be included in an updated visual overlay that is determined and sent to the AR display for display in real time or near-real time. Additionally, the IPR facilitator may calculate an arch length and indicate if a planned amount of interproximal reeducation has been achieved or cannot be achieved. The IPR facilitator may suggest additional actions to take to generate a desired interproximal gap. This suggestion may be provided via the visual overlay. For example, the IPR facilitator may determine an additional interproximal reduction to implement between two additional teeth to generate additional interproximal space.

One example dental procedure facilitator is an implant facilitator. The implant facilitator may virtually mark an area to place a hole for an implant in the visual overlay 164. The area to place the implant may be pre-planned or may be computed by the implant facilitator. For example, the implant facilitator may determine a mid-distance between teeth, may determine an arch of one or more teeth, may determine a middle of the jaw, may determine the position of a pre-planned location, etc. These determinations may be used to compute where to place the hole for the implant. If there is a CT scan of the jaw, then the bone portion of the dental arch that is not generally visible may be shown by registering the CT scan with the image data 162 and then including the CT scan data in the visual overlay 164. When the hole is to be drilled, the implant facilitator may provide information to orient and place a drill properly. As the drilling is performed, the implant facilitator may indicate when a desired depth has been reached for the hole and/or may power off the drill.

The tool identifier/controller 170 may include tool profiles that are usable to identify particular dental tools in the image data 162. Based on the tool profiles, tool identifier/controller 170 may determine a type of tool, a position of the tool and an orientation of the tool. A dental procedure facilitator 176 may identify a dental procedure to be performed, and may provide a visual indication of a position and/or orientation for a dental tool and/or for a position and/or shape of material to be removed from one or more teeth, material to be added to the one or more teeth, an implant to be inserted, a hole to be drilled, and so on. Tool identifier/controller 170 may control a power and/or one or more settings of a dental tool based on the position and/or orientation of the dental tool in relation to the dental procedure to be performed.

In one embodiment, treatment control module 120 includes a haptics module 177. A dental practitioner may wear haptics gloves that are capable of providing forces, vibrations and/or motions to the dental practitioner. Alternatively, or additionally, dental tools used by the dental practitioner may include haptics components that can provide such forces, vibrations and/or motions. AOI identifying modules 115 may generate haptic feedback areas based on the identified AOIs. The haptic feedback areas may correspond to the locations of the AOIs and/or may be near the AOIs.

When tool identifier/controller 170 determines that a dental tool has reached a haptic feedback area, haptics module 177 may send a signal to the haptic gloves and/or haptics enabled dental tool to cause a haptic feedback. The haptic gloves and/or dental tool may then provide a force, vibration or motion to indicate that the dental tool has reached the haptic feedback area. For example, if a particular position and orientation for a dental tool is required for a dental procedure, then the haptics module 177 may cause a haptic feedback to be provided when the dental tool achieves that position and/or orientation. Tool identifier/controller 170 may determine when the dental tool has reached that target position and orientation based on analysis of the image data 162. Similarly, haptic feedback may be provided during a drilling operation when a target depth has been reached. Similarly, a haptic feedback may be provided during one or more grinding operations when a desired amount of tooth removal at a particular area has been achieved.

In some embodiments, dental tools include sensors that may be used to facilitate tracking of the dental tools. This may increase an accuracy of tracking the dental tools verses relying solely on tracking of the dental tools from the image data 162. For example, dental tools may include accelerometers, gyroscopes, magnetic tracking sensors, image capture devices (e.g., complementary metal-oxide semiconductor (CMOS) sensors and/or charge-coupled device (CCD) image sensors). In the instance of image capture devices on dental tools, images generated by such image capture devices may be generated in real time or near-real time and registered against a 3-D model of a dental arch being operated on. A position of the image capture device on the dental tool, a field of view of the image capture device, etc. may be known, and a relative position of the image capture device to a tool tip (e.g., head of a grinder or head of a drill bit) may be known. Accordingly, captured images may be registered to the 3-D model to accurately determine a position and orientation of the dental tool relative to the dental arch.

In some embodiments, an intraoral scanner is used as an additional source of image data 163 during an intraoral procedure. The intraoral scanner may be positioned in the patient's oral cavity and pointed toward an area on the dental arch where a dental procedure is being performed. For example, the intraoral scanner may be positioned so as to take images of a tooth that is being drilled or ground. The intraoral scanner may provide a high resolution image of the dental procedure from an angle or view that a dental practitioner would otherwise not have access to. The image data from the intraoral scanner 163 may be received by AR processing module. AOI identifying modules 108 may then identify areas of interest from the image data 163 in addition to identifying areas of interest in image data 162. Additionally, tool identifier/controller 170 may identify a dental tool from the image data 163 and/or determine additional information about the dental tool from the image data 163 than can be determined from image data 162. AR display module 118 may generate a zoomed in view of the dental procedure based on the image data 163 received from the intraoral scanner. AR display module 118 may determine a region in a dental practitioner's view (e.g., a region of image data 162) that is outside of the oral cavity and dental arch. AR display module 118 may then generate a visual overlay 164 that includes the zoomed in view of the dental procedure from the image data 163. The visual overlay 164 may place the zoomed in view on the AR display at the region of the dental practitioner's field of view that is outside of the oral cavity and dental arch. Accordingly, the dental practitioner may alternate between focusing on his real-world physical view of the patient's oral cavity and the zoomed in view of the dental procedure as appropriate during the dental procedure to improve his or her accuracy at performing the dental procedure.

FIGS. 2-29 below describe example applications of AR enhancements for a dental practitioner. The examples are described with reference to images representing the AR display provided to a dental practitioner and/or flow charts describing processes of generating or providing such AR displays. In the examples, particular colors or types of indicators may be used to highlight AOIs or other elements on an AR display. However, the particular colors or types of indicators are examples and other types or color indicators may be used according to various embodiments described herein. In addition, the flow charts provide example processes that may be performed by an AR system. However, the processes performed by the AR system may include fewer or additional blocks than shown, and in some embodiments the processes in the flow charts may be performed in a different order than shown.

The methods depicted in FIGS. 2-29 may be performed by a processing logic that may comprise hardware (e.g., circuitry, dedicated logic, programmable logic, microcode, etc.), software (e.g., instructions run on a processing device to perform hardware simulation), or a combination thereof. Various embodiments may be performed by an AR system 100, a computing device 105 and/or an AR processing module 108 as described with reference to FIGS. 1A-1B.

Figure 2:
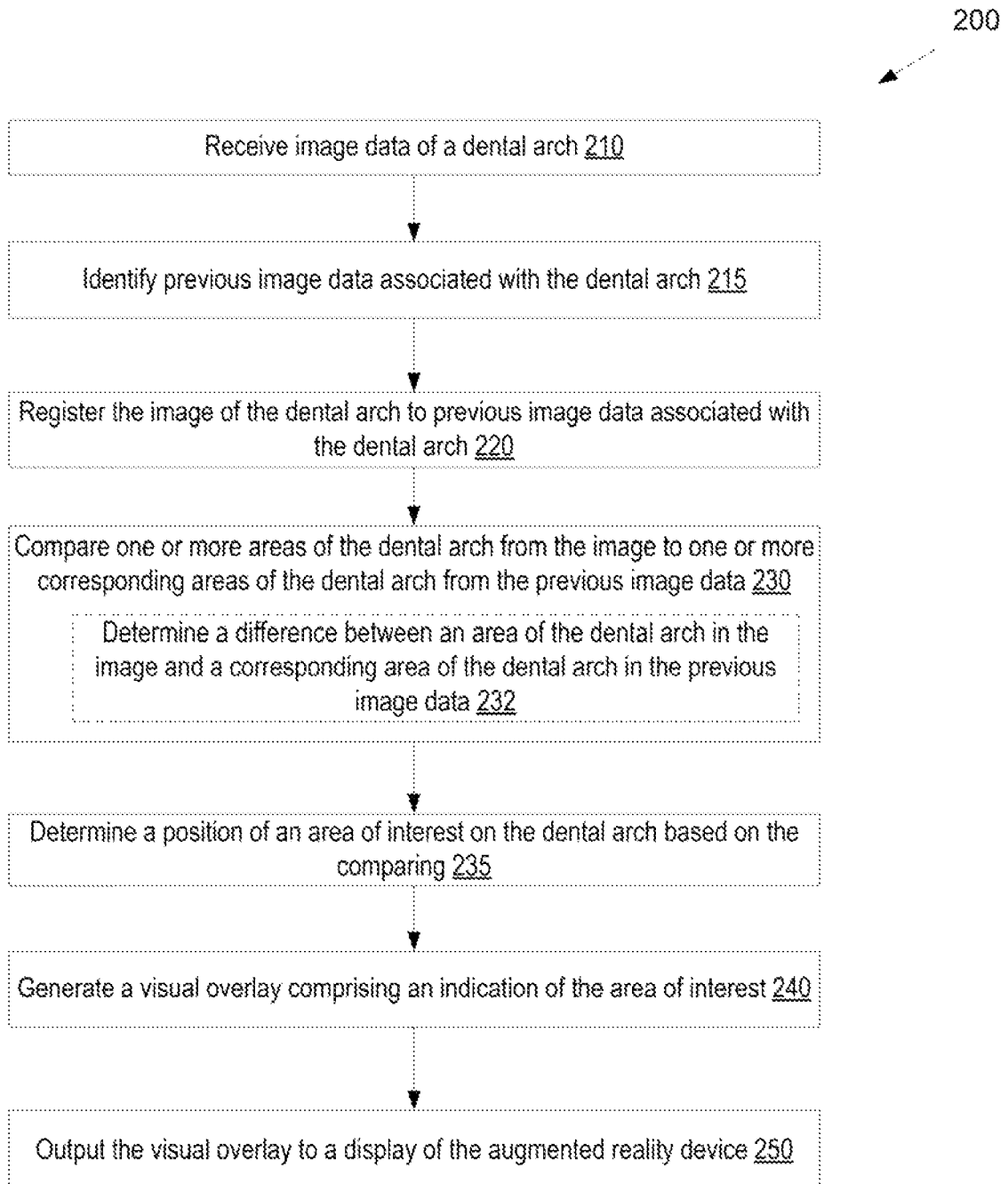
FIG. 2 illustrates a flow diagram for a method of determining areas of interest by an augmented reality device based on comparison to previous image data, in accordance with an embodiment.

FIG. 2 illustrates a flow diagram for a method 200 of determining areas of interest by an augmented reality device based on comparison to previous image data, in accordance with an embodiment. At block 210 of method 200, processing logic receives image data of a dental arch from an image capture device of an augmented reality system. At block 215, processing logic identifies previous image data associated with the dental arch. The previous image data may be stored in a patient history data store, for example. At block 220, processing logic registers the image of the dental arch to previous image data associated with the dental arch. Image registration may be performed as described herein above.

At block 230, processing logic compares one or more areas of the dental arch from the image to one or more corresponding areas of the dental arch from the previous image data. In one embodiment, based on the comparison processing logic determines a difference between an area of the dental arch in the image and a corresponding area of the dental arch in the previous image data. For example, differences such as changes in tooth wear, changes in gum recession, changes in gum color, changes in tooth color, changes in gum swelling, and so on may be identified. In one embodiment, processing logic may identify those changes that are over a threshold value for an amount of change.

At block 235, processing logic determines a position of an area of interest on the dental arch based on the comparison. The area of interest may be an area of the identified differences or an area of a tooth or gum for which the difference was identified. At block 240, processing logic generates a visual overlay comprising an indication of the area of interest. In one embodiment, the indication of the area of interest may use a color scheme or other indicator to indicate the magnitude of change to the identified area of interest. At block 250, processing logic outputs the visual overlay to display of the augmented reality system. The AOI in the visual overlay is superimposed on the display over a view of the dental arch at the position of the area of interest.

Figure 3:
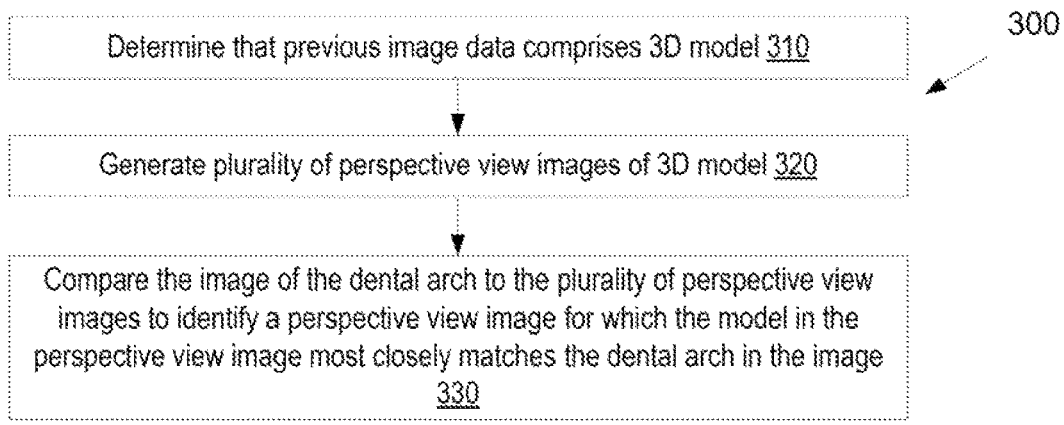
FIG. 3 illustrates a flow diagram for a method of registering image data from an augmented reality device to a three dimensional model, in accordance with an embodiment.

FIG. 3 illustrates a flow diagram for a method 300 of registering image data from an image capture device of augmented reality device to a three dimensional model, in accordance with an embodiment. Method 300 may be performed at block 220 of method 200. At block 310 of method 300, processing logic determines that previous image data comprises a three-dimensional (3-D) model of a dental arch. At block 320, processing logic generates a plurality of perspective view images of the 3-D model. At block 330, processing logic compares the image of the dental arch to the plurality of perspective view images to identify a perspective view image for which the model in the perspective view image most closely matches the dental arch in the image. The image data may then be registered to the 3-D model using the identified perspective view image.

Figure 4:
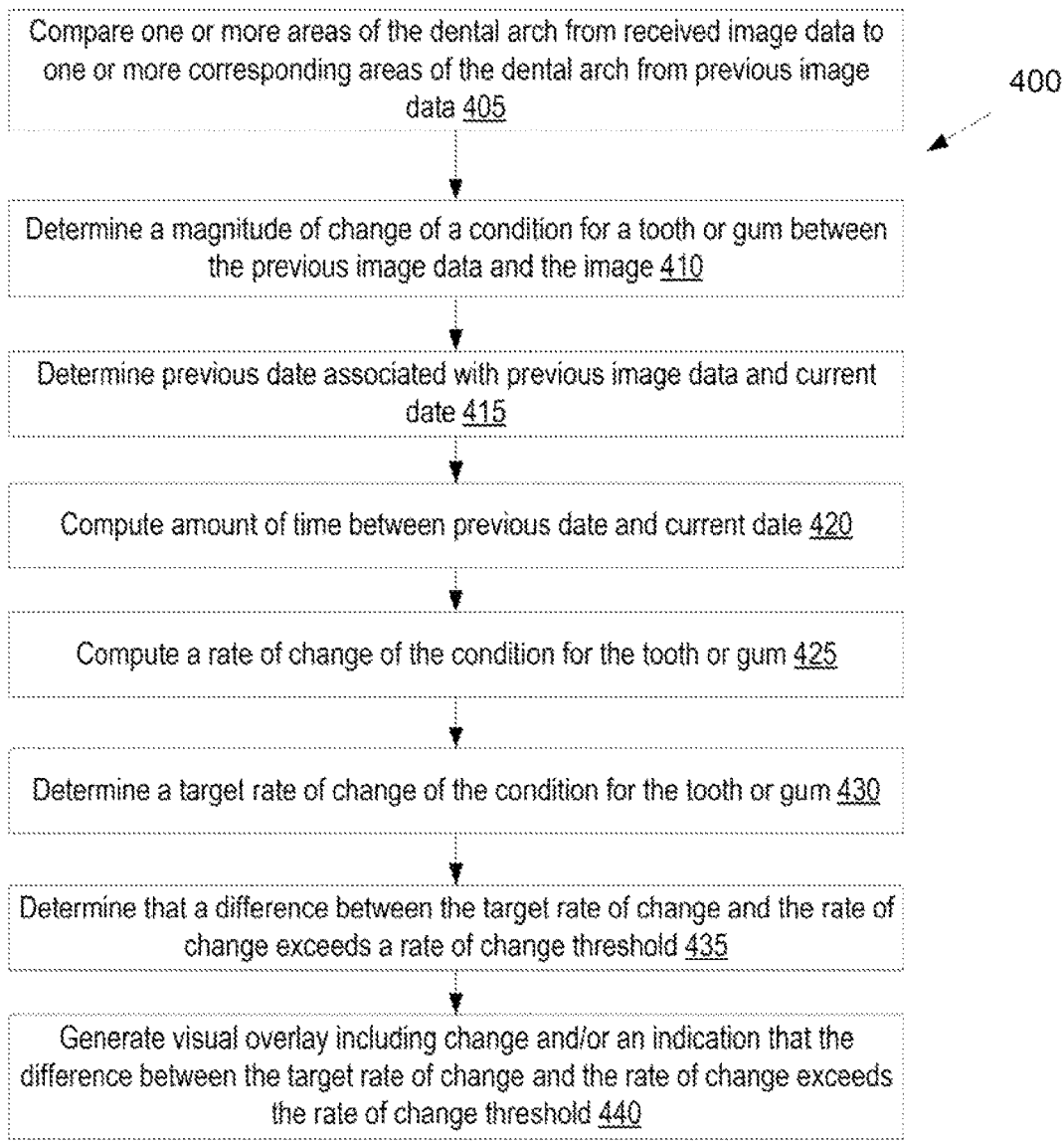
FIG. 4 illustrates a flow diagram for a method of determining differences between a dental arch as depicted in image data from an augmented reality device and the dental arch as depicted in previous image data, in accordance with an embodiment.

FIG. 4 illustrates a flow diagram for a method 400 of determining differences between a dental arch as depicted in image data from an image capture device of an augmented reality device and the dental arch as depicted in previous image data, in accordance with an embodiment. At block 405 of method 400, processing logic compares one or more areas of the dental arch from the image to one or more corresponding areas of the dental arch from previous image data. Based on the comparison, processing logic may identify a difference between the received image data and the previous image data at one or more locations on the dental arch. The difference may show a change in a dental condition such as an amount of tooth wear, an amount of gum recession, and so on. At block 410 of method 400, processing logic determines a magnitude of change of a condition from a tooth or gum between the previous image data and the current image data.

At block 415, processing logic determines a previous date associated with the previous image data and a current date associated with current image data. At block 420, processing logic computes an amount of time between the previous date and the current date. At block 425, processing logic computes a rate of change of a dental condition for the tooth or gum. At block 430, processing logic determines a target rate of change of the condition for the tooth or gum. At block 435, processing logic determines that a difference between the target rate of change and the rate of change that was identified exceeds a rate of change threshold. The rate of change threshold may be determined based on a healthy rate of change of the dental condition as viewed in a statistically significant sample of patients. At block 440, processing logic generates a visual overlay including the change in the dental condition and/or an indication that the difference between the target rate of change and the rate of change that was identified exceeds the rate of change threshold. The visual overlay may be projected onto the AR display so that the change is superimposed over an appropriate location of the tooth or gum that has undergone the change as viewed by the dental practitioner. The visual overlay may be updated in real time or near-real time as updated image data is received from the image capture device.

Figure 5:
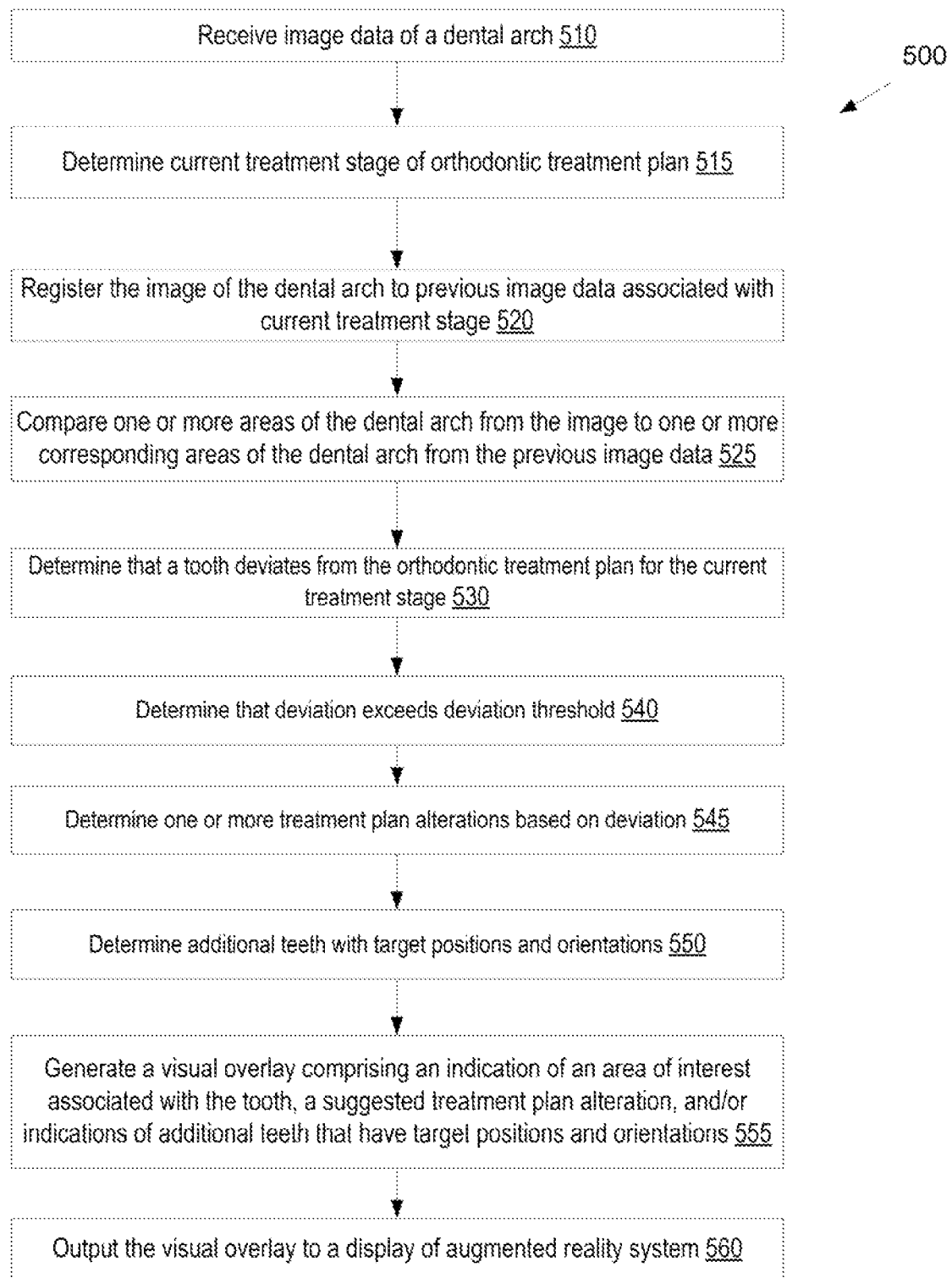
FIG. 5 illustrates a flow diagram for a method of tracking progress of an orthodontic treatment plan using image data from an augmented reality device, in accordance with an embodiment.

FIG. 5 illustrates a flow diagram for a method 500 of tracking progress of an orthodontic treatment plan using image data from an augmented reality device, in accordance with an embodiment. An orthodontic treatment plan may be generated based on an intraoral scan of a dental arch to be modeled. The intraoral scan of the patient's dental arch may be performed to generate a three dimensional (3D) virtual model of the patient's dental arch. For example, a full scan of the mandibular and/or maxillary arches of a patient may be performed to generate 3D virtual models thereof. The intraoral scan may be performed by creating multiple overlapping intraoral images from different scanning stations and then stitching together the intraoral images to provide a composite 3D virtual model. In other applications, virtual 3D models may also be generated based on scans of an object to be modeled or based on use of computer aided drafting techniques (e.g., to design the virtual 3D mold). Alternatively, an initial negative mold may be generated from an actual object to be modeled. The negative mold may then be scanned to determine a shape of a positive mold that will be produced.

Once the virtual 3D model of the patient's dental arch is generated, a dental practitioner may determine a desired treatment outcome, which includes final positions and orientations for the patient's teeth. Processing logic may then determine a number of treatment stages to cause the teeth to progress from starting positions and orientations to the target final positions and orientations. The shape of the final virtual 3D model and each intermediate virtual 3D model may be determined by computing the progression of tooth movement throughout orthodontic treatment from initial tooth placement and orientation to final corrected tooth placement and orientation. For each treatment stage, a separate virtual 3D model of the patient's dental arch at that treatment stage may be generated. The shape of each virtual 3D model will be different. The original virtual 3D model, the final virtual 3D model and each intermediate virtual 3D model is unique and customized to the patient.

Accordingly, multiple different virtual 3D models may be generated for a single patient. A first virtual 3D model may be a unique model of a patient's dental arch and/or teeth as they initially exist prior to treatment, and a final virtual 3D model may be a model of the patient's dental arch and/or teeth after correction of one or more teeth and/or a jaw. Multiple intermediate virtual 3D models may be modeled, each of which may be incrementally different from previous virtual 3D models.

Each virtual 3D model of a patient's dental arch may be used to generate a unique customized mold of the dental arch at a particular stage of treatment. The shape of the mold may be at least in part based on the shape of the virtual 3D model for that treatment stage. Aligners may be formed from each mold to provide forces to move the patient's teeth. The shape of each aligner is unique and customized for a particular patient and a particular treatment stage. In an example, the aligners can be pressure formed or thermoformed over the molds. Each mold may be used to fabricate an aligner that will apply forces to the patient's teeth at a particular stage of the orthodontic treatment. The aligners each have teeth-receiving cavities that receive and resiliently reposition the teeth in accordance with a particular treatment stage.

At block 510 of method 500, processing logic receives image data of a dental arch from an image capture device of an augmented reality device. At block 515, processing logic determines a current treatment stage of the orthodontic treatment plan. At block 520, processing logic registers the image of the dental arch to previous image data associated with the current treatment stage. The previous image data associated with the current treatment stage may include the three-dimensional virtual model of the dental arch for the current treatment stage. Registration of the current image data to the virtual 3-D model of the dental arch may be performed as set forth in method 300.

At block 525, processing logic compares one or more areas of the dental arch from the received image to one or more corresponding areas of the dental arch from the previous image data (e.g., from the virtual three-dimensional model associated with the current treatment stage). At block 530, processing logic determines that a tooth deviates from the orthodontic treatment plan for the current treatment stage. Each treatment stage is expected to move a patient's teeth by a predetermined amount. Teeth that deviate from the treatment plan may have moved less than anticipated or more than anticipated. If one or more of the patient's teeth are not moved by the predetermined amount, this may be caused by complications such as roots of adjacent teeth colliding. At block 540, processing logic determines that the deviation exceeds a deviation threshold.

At block 545, processing logic determines one or more treatment plan alterations based on the deviation. For example, there may be multiple different treatment paths to adjust a patient's teeth to the desired final positions. If a first treatment path is not adjusting the teeth as expected, one or more viable alternative treatment paths may be determined. Additionally, some types of tooth movement such as particular rotations of teeth may not be achieved successfully without adding attachments to the teeth to be rotated. If a tooth has not undergone a desired rotation, then a suggested attachment may be determined for that tooth to apply additional rotational forces on the tooth. Other types of treatment plan alterations may also be determined.

In one embodiment, processing logic provides 3-D controls for a dental practitioner wearing the AR display to adjust the treatment plan. For example, the dental practitioner may move a tooth, rotate a tooth, etc. by interacting with a virtual 3-D model of the patient's dental arch that is displayed via the AR display.

At block 550, processing logic may determine additional teeth that have undergone motion in accordance with the orthodontic treatment plan and that therefore have the target positions and orientations. At block 555, processing logic generates a visual overlay comprising an indication of an area of interest associated with the tooth. The visual overlay may also include a suggested treatment plan alteration. For example, the visual overlay may indicate one or more regions on a tooth or teeth to place attachments. The visual overlay may also include indications of additional teeth that have target positions and orientations as indicated in the orthodontic treatment plan. In an example, teeth that have failed to move as indicated in the orthodontic treatment plan may be highlighted in a first color while teeth that have moved according to the orthodontic treatment plan may be highlighted in a second color.

The visual overlay may also indicate a desired position and orientation for a tooth that has not moved as predicted. Accordingly, a dental practitioner may visually see the difference between one or more teeth at the current treatment stage and the one or more teeth as they were predicted to be at the current treatment stage. Processing logic may provide the dental practitioner with one or more options for showing playback of the dental arch from initial positions of the teeth to current positions of the teeth and all the way to treatment outcome positions of the teeth. Such playback may be implemented as a stream of visual overlays that are projected onto the AR display. The visual overlays may be superimposed over the actual patient's teeth in a field of view of the dental practitioner as though the patient's teeth are moving according to the treatment plan before the dental practitioner's eyes. Processing logic may update a treatment outcome determination based on differences in the predicted tooth positions at the current treatment stage and the actual tooth positions at the current treatment stage.

At block 560, processing logic outputs the visual overlay to a display of the augmented reality device.

Figure 6:
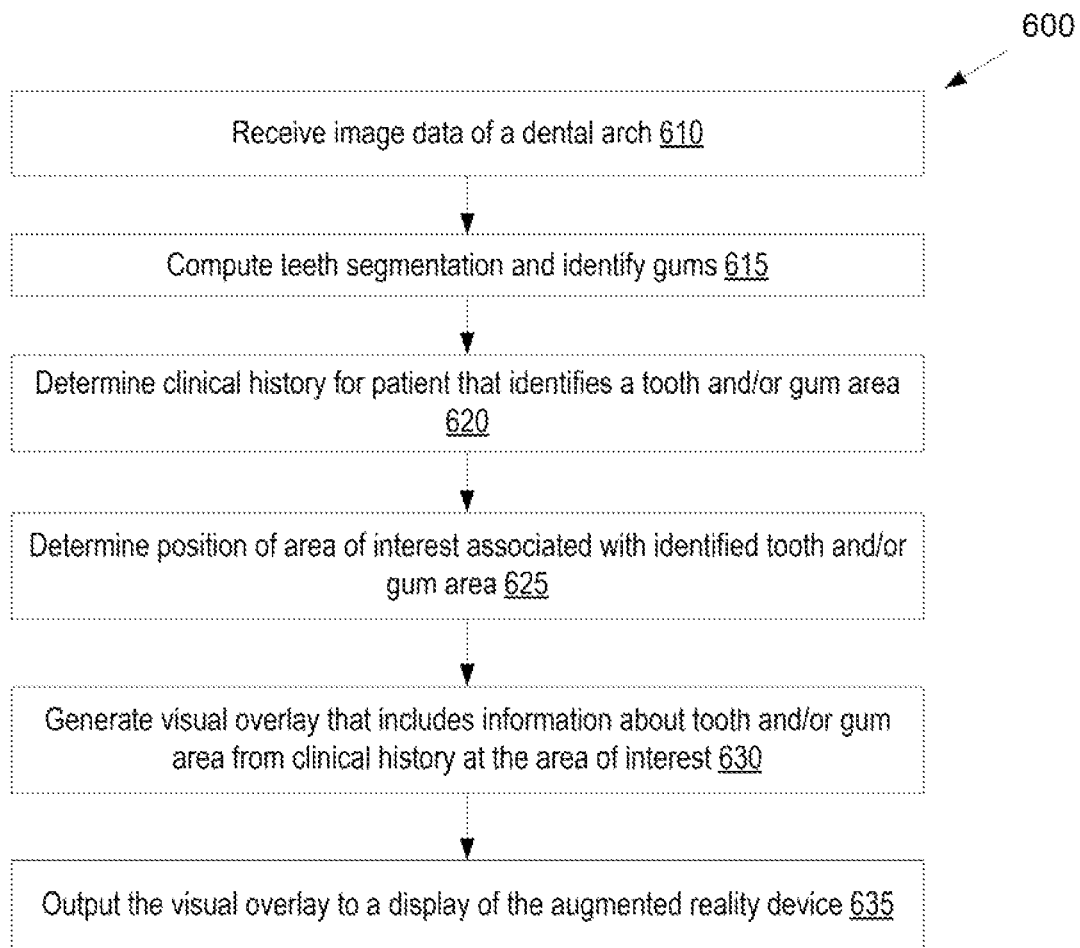
FIG. 6 illustrates a flow diagram for a method of augmenting the view of a patient's mouth through an augmented reality display based on a clinical history of the patient, in accordance with an embodiment.

FIG. 6 illustrates a flow diagram for a method 600 of augmenting the view of a patient's mouth through an augmented reality display based on a clinical history of the patient, in accordance with an embodiment. At block 610 of method 600, processing logic receives image data of the dental arch generated by an image capture device of an augmented reality device. At block 615, processing logic computes teeth segmentation and identifies gums from the received image data. After teeth segmentation, processing logic may determine the identities of individual teeth. For example, in dentistry each tooth is generally identified by a tooth number (e.g., an American Dental Association tooth identifier, Palmer notation tooth identifier, or Federation Dentaire Internationale tooth identifier). Processing logic may determine the tooth number associated with each tooth identified in the received image data.

At block 620, processing logic determines a clinical history for the patient that identifies a tooth and/or gum area. For example, the clinical history may identify that one or more dental procedures had been performed on a particular tooth or gum area at a previous date. The clinical history may also indicate previous dental conditions for the patient such as broken teeth, swollen gums, gum recession, fillings, and so on. The clinical history may identify which teeth and/or location on the dental arch the previous dental conditions applied to.

At block 625, processing logic determines a position of an area of interest associated with an identified tooth and or gum area from the clinical history. At block 630, processing logic generates a visual overlay that includes information about a tooth and/or gum area from the clinical history at the identified area of interest. For example, processing logic may highlight tooth number five in the visual overlay with an indicator that tooth number five has a crack if the clinical history indicates such. Processing logic may additionally add to the visual overlay a label for each of the one or more teeth that are visible in the image data, where the label indicated an identity of a tooth (e.g., identifies tooth 5). At block 635, processing logic outputs the visual display to a display of an augmented reality device. The visual overlay is superimposed over a dental practitioner's view of the dental arch on the display at the position of the area of interest.

Figure 7:
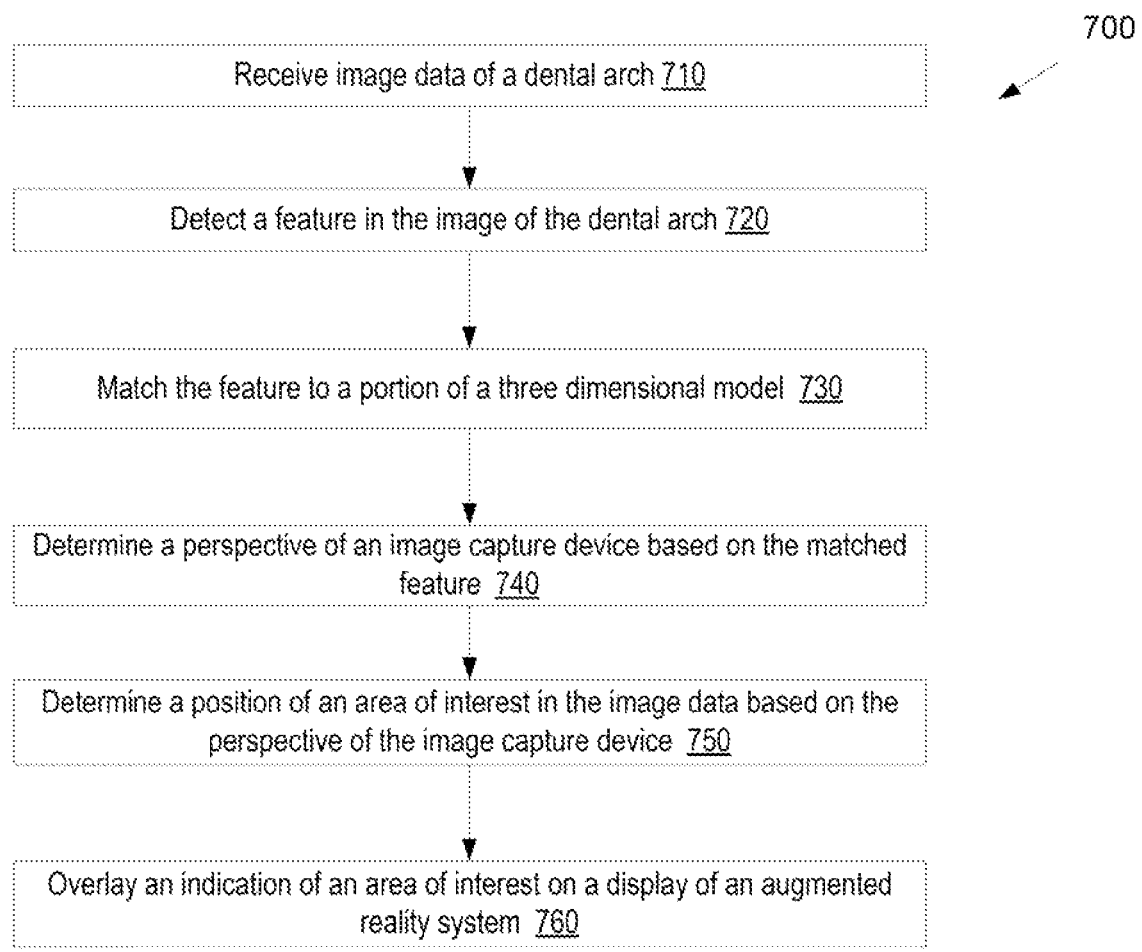
FIG. 7 illustrates a flow diagram for a method of augmenting the view of a patient's mouth through an augmented reality display, in accordance with an embodiment.

FIG. 7 illustrates a flow diagram for a method 700 of augmenting the view of a patient's mouth through an augmented reality display, in accordance with an embodiment. Beginning in block 710, processing logic receives image data of a dental arch. For example, the AR system may receive the image data from an image capture device. The image data may include a two dimensional image or video data. In some embodiments, the received image data may include a three dimensional image or stereoscopic image data generated from a variety of image capture devices.

In block 710, the processing logic may detect a feature in the image of the dental arch. For example, a feature may be a tooth, several teeth, a gum line, a contour, or any other feature of the dental arch in the image data. In some embodiments, the AR system may first identify a general feature such as a mouth or a dental arch, and then identify a specific feature such as a tooth or gum line within the dental arch. In some embodiments, the AR system may use previously identified features to aid detecting a new feature. For example, if a tooth was previously analyzed from a previous image, the AR system may search for a new feature representing a second tooth by searching image data near the original tooth.

In block 730, the processing logic matches the feature to a portion of a three dimensional model. For example, the processing logic may generate two dimensional projections for the three dimensional model from different perspectives to simulate the image data that would be received from different camera angles and positions. The three dimensional model may be manipulated by the processing logic over six degrees of freedom of movement. The AR system may then use such projections to attempt to match the detected feature to a portion of the three dimensional model. In some embodiments, the processing logic may constrain the search for a match between the detected feature and the three dimensional model to certain potential image capture device positions. For example, the processing logic may limit the search to portions of the three dimensional model that are visible from an opening of a patient's mouth for matches to the detected feature, or may search within a restricted range of positions expected to be viewed from an image capture device.

In some embodiments, processing logic may also compare the feature in the image to a plurality of recorded features in a data store. For example, the data store may include reference data from previous images or scans taken for other patients. The recorded features in the data store may be images of the features, models of the features, or another representation of the features. The recorded features may be stored with an indication of clinical data relevant to the feature. For example, the recorded features may have metadata or a file associated with them that stores AOIs associated with the features or an indication if a feature is normal and has no AOIs. In some embodiments, the processing logic may limit the comparison of the detected feature to recorded features of the same type. For example, the processing logic may compare a detected tooth to recorded teeth, a detected gum-line to a recorded gum line, or the like.

In block 740, the processing logic determines a perspective of the image capture device based on the matched feature. For example, if the detected feature matches a portion of the three dimensional model when rotated and placed in a specific position, the AR system may determine a perspective or position of an image capture device that generated the image.

In block 750, the processing logic may determine a position of an AOI in the image data based on the perspective of the image capture device. The position may be determined relative to the position of the image capture device, relative to the three dimensional model, or relative to the received image data. Because a feature of the dental arch in the image data is matched to the three dimensional model, and a position of the image capture device is determined based on the match, determining a position of an AOI relative to the image data, dental arch, or position of the camera generates a position that can be correlated to the others. In some embodiments, the processing logic may determine a position of the AOI in a two dimensional field of view of the received image data. This position may then be converted to specific positions in the view of each eye of a dental practitioner using the AR system. For example, a first position may be determined for the line of sight of a right eye, and a second position may be determined for the line of sight of the left eye.

In block 760, the processing logic overlays an indication of the AOI on an AR display. The indication overlay may be positioned on the AR display so as to appear in the position of the AOI on the dental arch. For example, the AR system may project an indication of the AOI onto each lens in the frame of a set of AR glasses. The indication may mark the AOI with a color or other indicator to highlight the AOI for the dental practitioner. The indicator may also show the type of AOI, or other information about the AOI.

Figure 8A:
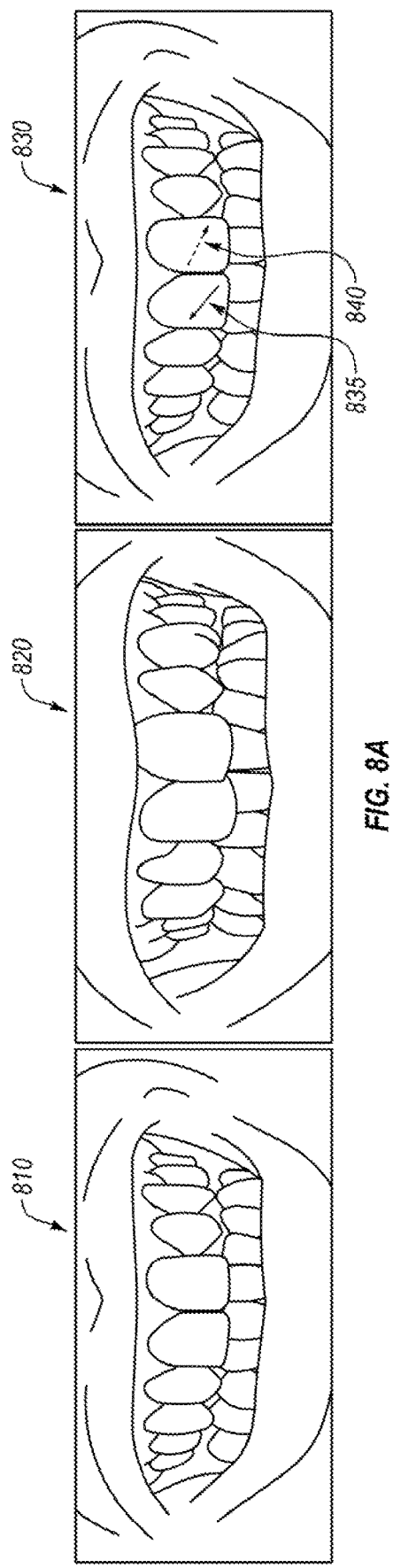
FIG. 8A illustrates a view of an example augmented reality display showing areas of interest, in accordance with an embodiment.
Figure 8B:
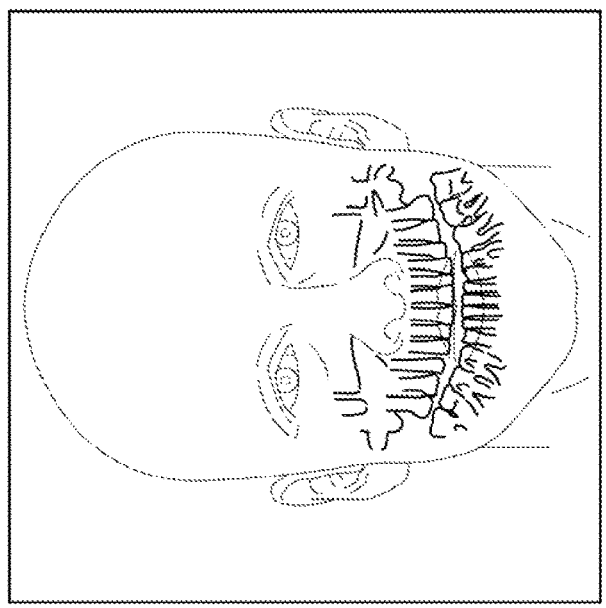
FIG. 8B illustrates a view of an example augmented reality display showing areas of interest, in accordance with an embodiment.

FIGS. 8A and 8B are example illustrations of a portion of a view of an AR display having overlay indicators generated using methods described with reference to FIGS. 5-7, or similar methods. FIG. 8A is an example illustration of a portion of an AR display 830 showing indicators 835, 840 positioned on the AR display to indicate movement in the position of teeth in a dental arch compared to previous patient data. A visual overlay for the AR display may be generated beginning with image data 810. The image data 810 shows a current image of a patient's smile as seen by a dental practitioner through the AR display. The image data 810 in FIG. 8A is shown as a two dimensional image, but may also be used by an AR system as stereoscopic image data, scan data, or other image data.

Previous image data 820 is also used by the AR system to determine whether there has been a change in the dentition of the patient since a previous scan. Similar to the image data 810, the image data 820 may be a two dimensional image, stereoscopic image data, previous scan data, a three dimensional model, or another representation of previous patient data. The AR system may compare the image data 810 to the previous image data 820 to determine if there has been a change in the dental arch, or to identify other AOIs. In the example shown in FIG. 8A, the alignment and position of the front teeth have changed since the previous data was taken. Accordingly the AR system may determine a direction and amount of change in the position of the teeth. The change in the position of the teeth may then be translated into an indication for the dental practitioner.

A portion of a view of the AR display is shown in FIG. 8A having a visual overlay that includes the indications 835, 840 of the direction and amount of change of teeth in image data. Specifically, the view of the dental practitioner as shown in the image data is overlay with the visual overlay showing the indicators 835, 840. The indications 835, 840 may include a two dimensional (or in some embodiments three dimensional) vector indicating a direction and amount of movement of a particular tooth. A first color, graphic or line type may be used to show a vector that represents an amount of movement that was planned (e.g., for indicator 840) and a second color, graphic or line type may be used to show a vector that represents an unplanned amount of movement, such as an amount of movement that is below a planned amount of movement (e.g., for indicator 835). In some embodiments, other indicators may be used to convey the movement of teeth in a dental arch. For example, if the movement is part of a planned orthodontic treatment, the indicators may highlight teeth based on whether their movement is on track with the planned treatment. Accordingly, teeth that are in an expected position may be highlighted with one color, and teeth that are not moving as expected may be highlighted with another color. In some embodiments, the AR system may indicate to the dental practitioner the teeth that are not moving in an expected manner. In other embodiments, any other indication of the position or movement of teeth may be generated and displayed in an AR display as alternatives or additions to the indicators 835, 840 shown in FIG. 8A.

FIG. 8B is an example of a portion of a view 850 of an AR display showing an overlay of the skeletal structure of a patient. The skeletal structure may be generated from a previous scan (e.g., a CT scan), previous x-ray imaging, or other previous data for the patient. The AR system may align the skeletal structure to the patient using methods similar to those discussed with reference to FIGS. 2-7. For example, the AR system may detect a feature in imaging data received from an image capture device. When looking at the front of the patient, such a feature may be a tooth, a gum line, a contour of the dental arch, or another feature in the imaging data. In some embodiments, the AR system may also determine a feature from a profile view of a patient based on the dental arch or based on other features, such as a patient's nose, chin, lips, or other structure. The AR system may then compare the feature to a three dimensional model (such as generated from previous scan, x-ray, or other data) and/or to optical image data to determine a position of the image capture device relative to the virtual three dimensional model and/or optical image data. The AR system may then provide an overlay of the patient's jaw as shown in the portion of the view 850 of an AR display.

In some embodiments, the AR system may display only a portion of the jaw of a patient as an overlay on the patient's face. For example, the AR system may display only a portion of the jaw that has an AOI for the patient, or a portion of the jaw that is not visible from the viewpoint of the AR system. The AR system may overlay portions of the jaw that are covered by the lips or cheeks of the patient, for instance. In some embodiments, the dental practitioner may request the overlay of the skeletal structure of a patient's jaw or a type of overlay while viewing the patient. For example, the dental practitioner may request to see x-ray images as an overlay on the patient's jaw, CT scan data as an overlay, or a three dimensional model of the patient's jaw as an overlay. The AR system may the project the overlay onto an AR display to augment the view of the dental practitioner through the AR display.

Figure 9:
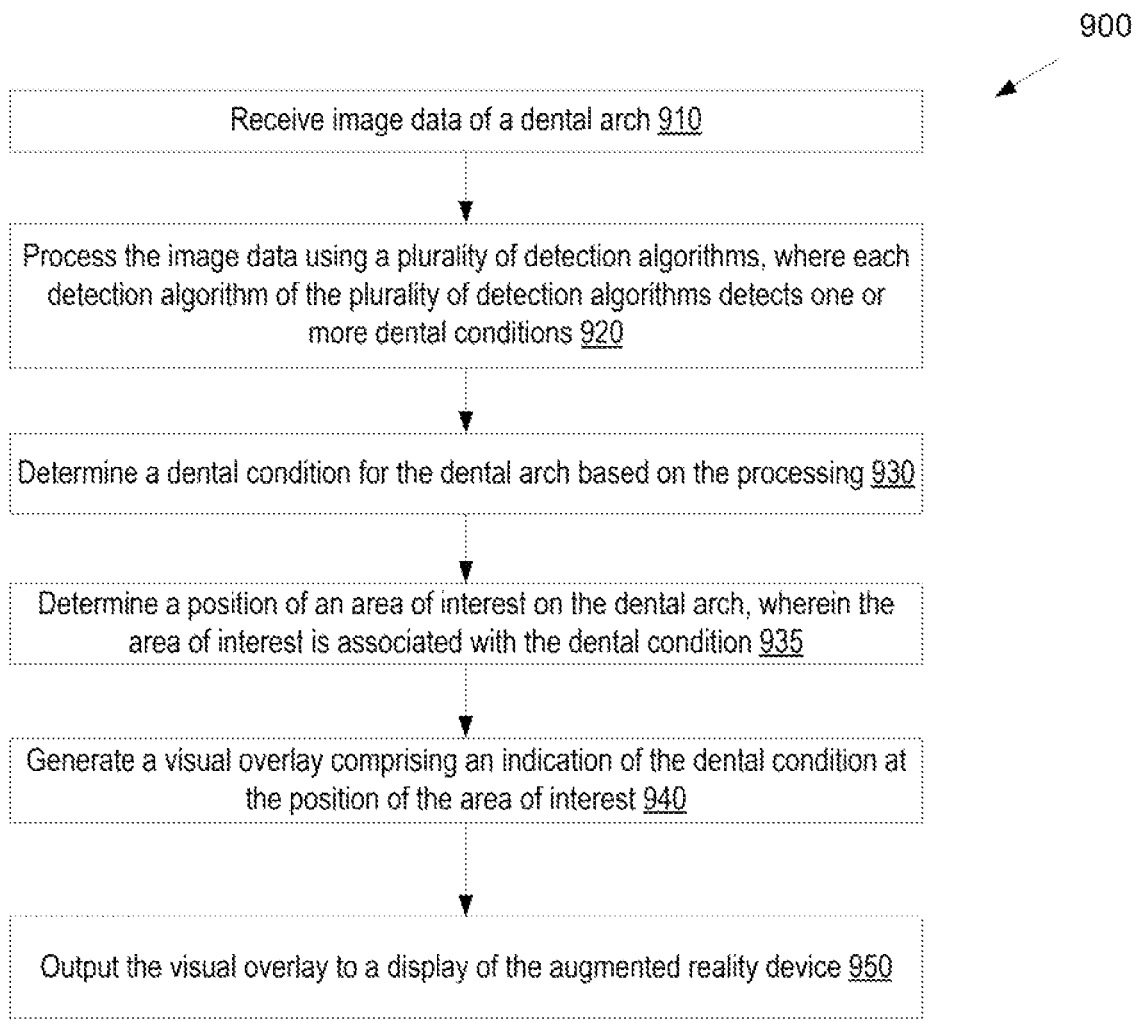
FIG. 9 illustrates a flow diagram for a method of determining areas of interest by an augmented reality device, in accordance with an embodiment.

FIG. 9 illustrates a flow diagram for a method 900 of determining areas of interest by an augmented reality device, in accordance with an embodiment. At block 910 of method 900, processing logic receives image data of a dental arch (e.g., of an oral cavity that includes a dental arch). At block 920, processing logic processes the image data using a plurality of detection rules. Each detection rule may be or include a different dental condition profile, model and/or algorithm. The dental condition profile may include training data that was used to generate a feature set and or a dental condition model. Each dental condition rule (e.g., dental condition profile, model and/or algorithm) may be used to detect one or more dental conditions.

At block 930, processing logic determines a dental condition for the dental arch based on the processing performed at block 920. At block 935, processing logic determines a position of an area of interest on the dental arch. The area of interest is associated with the dental condition. At block 940, processing logic generates a visual overlay comprising an indication of the dental condition at the position of the area of interest. The indication of the dental condition may be, for example, a contour of at least a portion of a tooth and/or gum that includes the dental condition. At block 950, processing logic outputs the visual overlay to a display of the augmented reality device. The visual overlay is superimposed over a view of the dental arch on the display at the position of the area of interest. Accordingly, a dental practitioner may see a real-world view of the patient's dental arch along with a computer generated overlay of the AOI.

Figure 10:
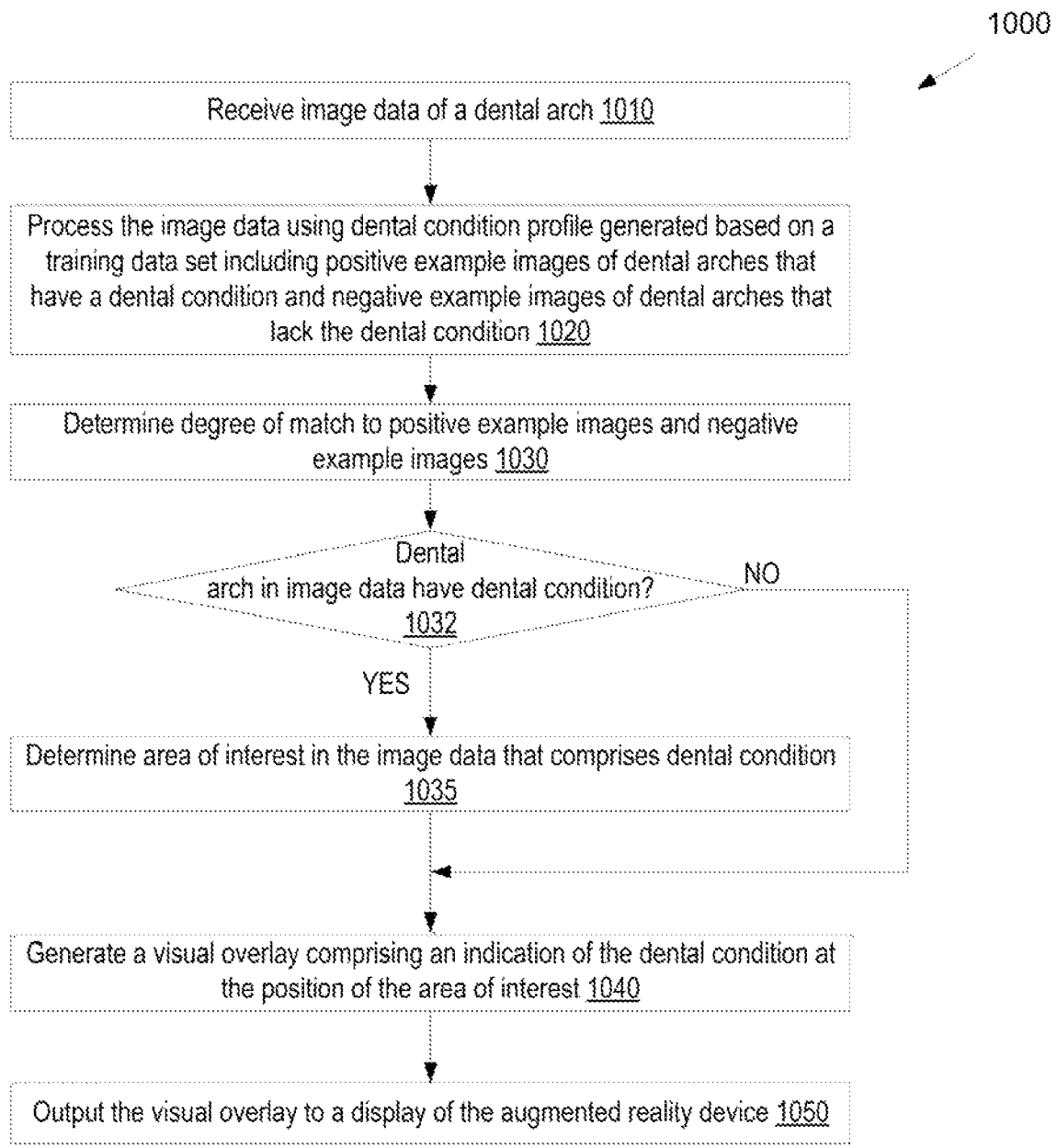
FIG. 10 illustrates a flow diagram for a method of processing image data of a dental arch from an augmented reality device based on machine learning profiles of dental conditions, in accordance with an embodiment.

FIG. 10 illustrates a flow diagram for a method 1000 of processing image data of a dental arch from an augmented reality device based on machine learning profiles of dental conditions, in accordance with an embodiment. At block 1010 of method 1000, processing logic receives image data of a dental arch. At block 1020, processing logic processes the image data using a dental condition profile generated based on a training data set including positive example images of dental arches that have a dental condition and negative example images of dental arches that lack the dental condition. At block 1030, processing logic determines, for the image data, a degree of match to the positive example images and to the negative example images using a feature set and a dental condition model included in the dental condition profile.

At block 1032, processing logic determines whether the dental arch in the image data has a dental condition associated with the dental condition profile. The dental arch is determined to have the dental condition if a tooth or gum area of the dental arch is determined to have features that match features of the positive example images with a confidence level that is greater than a confidence level threshold. Alternatively the dental arch is determined not to have the dental condition if there are no teeth or gum areas on the dental arch that have features that are determined to match the positive example images. If at block 1032 it is determined that the dental arch does include the dental condition, then the method continues to block 1035. Otherwise the method proceeds to block 1040.

At block 1035, processing logic determines an area of interest in the image data that comprises the dental condition. At block 1040, processing logic generates a visual overlay comprising an indication of the dental condition at the position of the area of interest. At block 1050, processing logic outputs the visual overlay to a display of the augmented reality device. The visual overlay is superimposed over a view of the dental arch on the display at the position of the area of interest.

Figure 11:
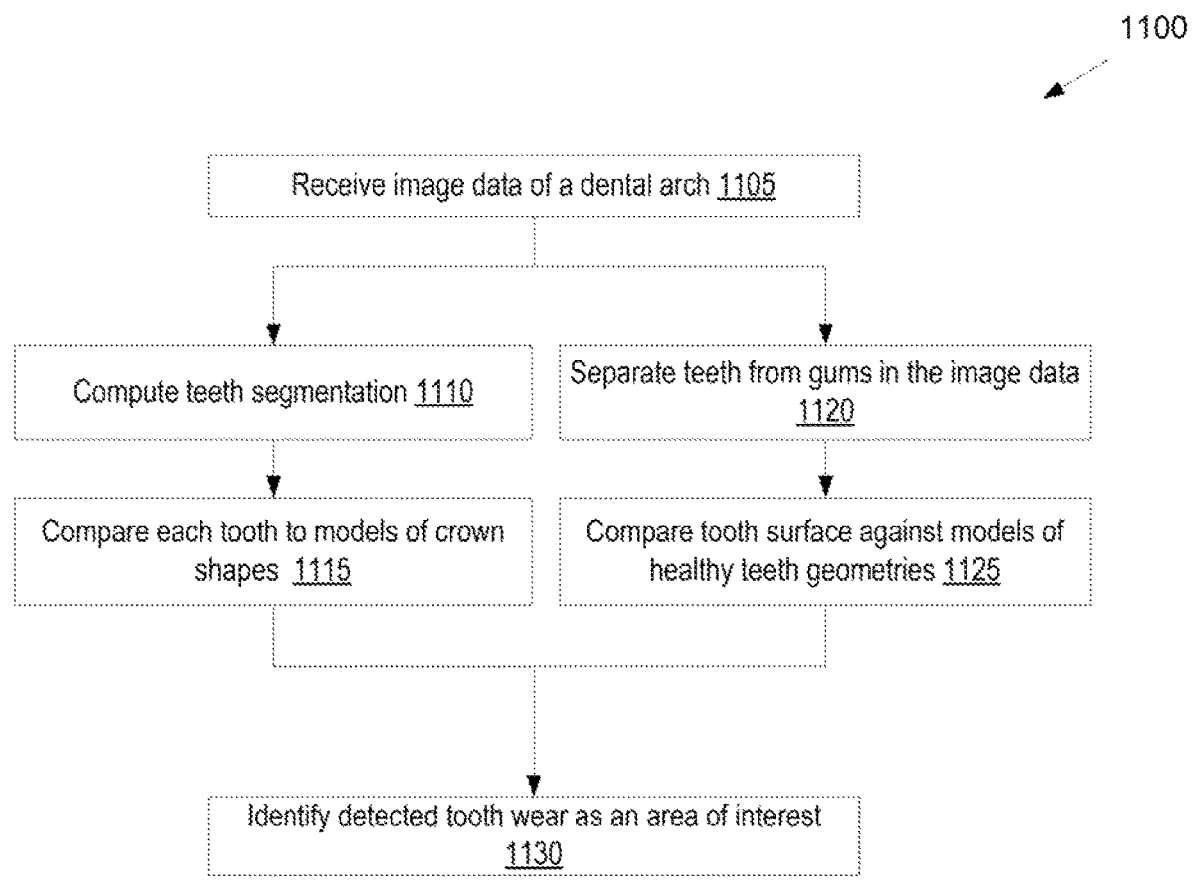
FIG. 11 illustrates a flow diagram for a method of processing image data of a dental arch from an augmented reality device to identify tooth wear, in accordance with an embodiment.

FIG. 11 illustrates a flow diagram for a method 1100 of processing image data of a dental arch from an image capture device of an augmented reality device to identify tooth wear, in accordance with an embodiment. The processes in FIG. 11 may be used in conjunction or as an alternative to portions of the processes described with reference to FIGS. 2-10 to detect AOIs for teeth. Beginning in block 1105, an AR system receives image data of a dental arch. For example, the AR system may receive the image data from an image capture device. The image data may include a two dimensional image or video data. In some embodiments, the received image data may include stereoscopic image data generated from a variety of image capture devices. Furthermore, the image data may be a model generated from stereoscopic image data.

The process may continue in blocks 1110 and 1120 to provide two methods of detecting tooth wear. In some embodiments, the AR system may use only the first detection method or only the second detection method. Starting with the first detection method in block 1110, the AR system computes teeth segmentation. To compute tooth segmentation, the AR system may identify outlines of teeth and identify regions of image data that are within the outlines to define as particular teeth. In particular, the tooth segmentation may be performed to identify the surface of a tooth that would contact another tooth. The segmentation computation may also generate a model representing each tooth or a surface of each tooth.

In block 1115, the AR system continues to compare each tooth to models of crown shapes. For example, reference data in a data store may have models of various crown shapes. The crown shapes may be based on image data or based on virtual models of crowns. The models may include ideal crown shapes and/or crown shapes that have evident tooth wear. Based on the comparison, the AR system may continue to block 1130 to identify tooth wear as an AOI. The AR system may then generate an indication of the tooth wear to display on the AR display.

In the second detection method, the AR system may begin in block 1120 by separating teeth from gums in the image data. The separated teeth may be roughly separated based on the color of the teeth compared to the color of the gums. In some embodiments, the teeth may be separated from the gums in another manner. The AR system may continue in block 1125 to compare the tooth surfaces of the separated teeth against models of healthy teeth. The comparison may indicate portions of the teeth in the image data that do not conform to an expected size, shape, or structure from the healthy models geometries. Based on the comparison, the AR system may continue to block 1130 to identify tooth wear as an AOI. The AR system may then generate an indication of the tooth wear to display on the AR display.

FIGS. 12A and 12B illustrate example outputs to an AR display based on live analysis of image data of a dental arch. In FIG. 12A, tooth wear is indicated on a patient's dental arch. In some embodiments, the tooth wear may have been detected according to methods described with reference to FIGS. 2-10, or based on other methods. FIG. 12A shows a portion 1210 of the view of an AR system before the AR system has analyzed image data from a dental arch. The AR system may then perform processing on the image data to identify tooth wear. The tooth wear may then be highlighted on a portion 1220 of the view of the AR display as shown. The indicators 1225 may identify the tooth wear for the dental practitioner. The indicators 1225 shown in FIG. 12A highlight specific areas of tooth wear in a color that contrasts with the tooth color. In some embodiments, the AR system may select the color based on the AOI being tooth wear and another color could indicate another type of AOI. Additionally, other types of indicators may be used by the AR system. For example, the AR system may have indicators that point to, circle, or otherwise identify areas with tooth wear without or in addition to highlighting the tooth wear. Furthermore, in some embodiments, the AR system may provide an audio indication of the AOI. For example, the AR system may have a speaker to announces the AOI (e.g., by tooth number) and the type of AOI. In some embodiments, the AR system may provide a variety of indications for a particular AOI.

FIG. 12B illustrates an example view of an AR display identifying AOIs of a dental arch. FIG. 12B shows a portion 1230 of a view of an AR display with a visual overlay showing indicators of AOIs identified based on image data of a dental arch. For example, the AOIs 1235 and 1240 identified in the dental arch may be identified based on methods described with reference to FIGS. 2-7 and FIGS. 9-14 above, or based on other methods. As illustrated in FIG. 12B, the AR display shows the dental arch with an overlay 1235 and 1240 indicating areas of interest.

The first AOI 1235 is a dashed circle pointing out an area of interest and the second AOI 1240 is a solid circle pointing out an area of interest. In some embodiments, the different indicators may indicate different types of AOIs. For example AOI 1235 may indicate plaque, while AOI 1240 may indicate a potential cavity or crack. In some embodiments, the different indicators may indicate a severity of an identified AOI. For example, AOI 1235 may indicate a small area of plaque, while AOI 1240 may indicate a large area of plaque. In some embodiments, the indicators may be of different shapes or styles to indicate AOIs of different types or severities. In addition, in some embodiments, the AR display may further provide a text indicator describing what an overlay indicates.

Figure 13:
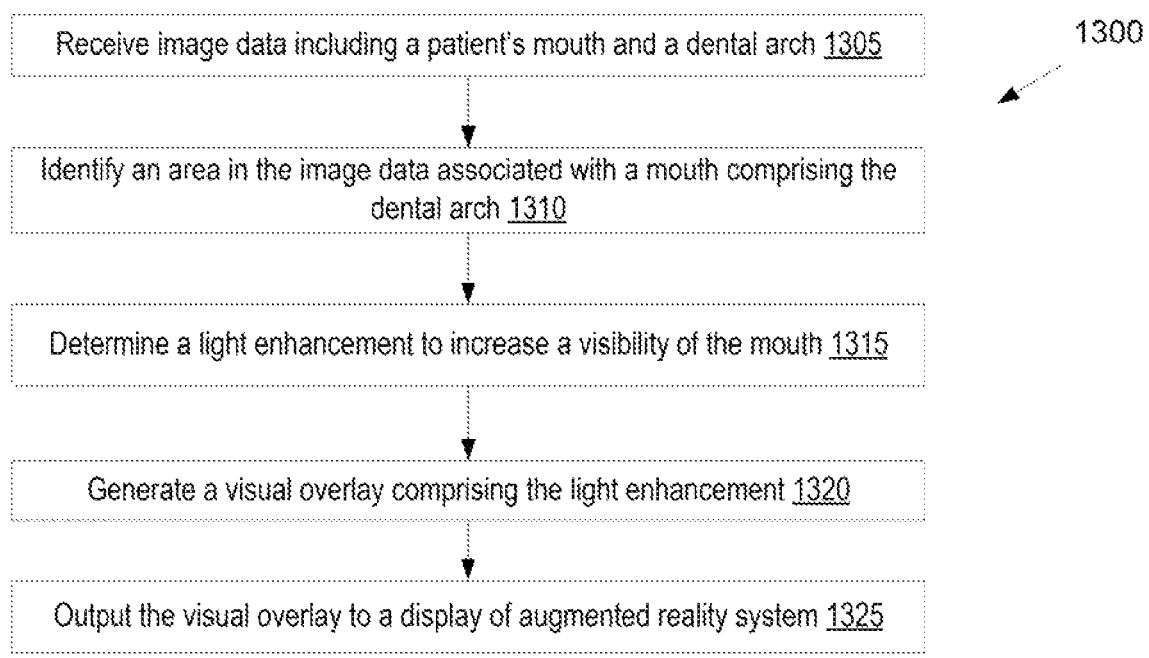
FIG. 13 illustrates a flow diagram for a method of enhancing a view of a patient's mouth as viewed through an augmented reality device, in accordance with an embodiment.

FIG. 13 illustrates a flow diagram for a method 1300 of enhancing a view of a patient's mouth as viewed through an augmented reality display, in accordance with an embodiment. At block 1305 of method 1300, processing logic receives image data including a patient's mouth (e.g., oral cavity) and a dental arch in the mouth or oral cavity. At block 1310, processing logic identifies an area in the image data associated with a mouth/oral cavity comprising the dental arch. At block 1315, processing logic determines a light enhancement to increase the visibility of the mouth/oral cavity. At block 1320, processing logic generates a visual overlay comprising the light enhancement. At block 1325, processing logic outputs the visual overlay to a display of an augmented reality device.

Figure 14:
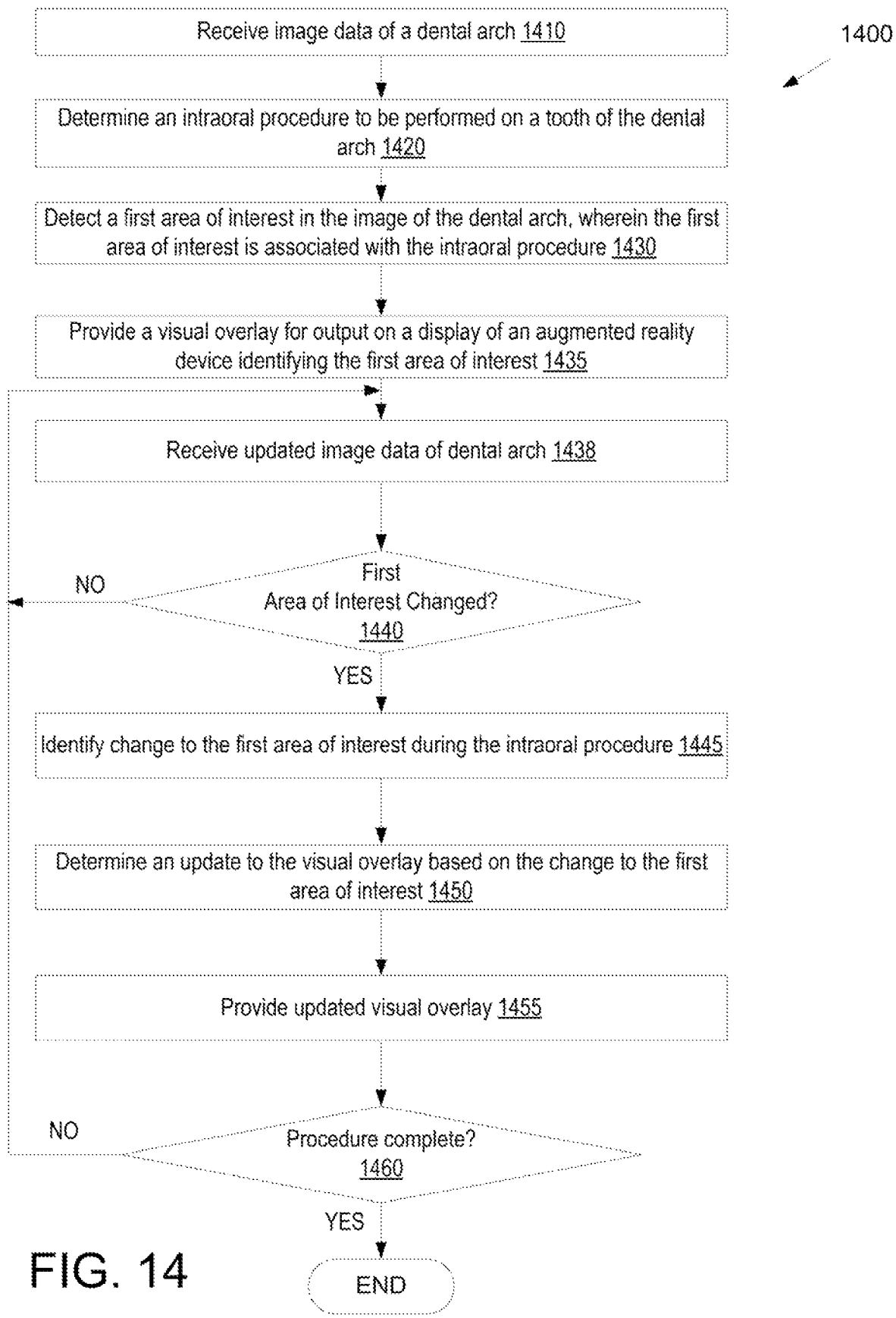
FIG. 14 illustrates a flow diagram for a method of providing a visual overlay of a patient's mouth during a dental procedure to augment the dental procedure, in accordance with an embodiment.

FIG. 14 illustrates a flow diagram for a method 1400 of providing a visual overlay of a patient's mouth during a dental procedure to augment the dental procedure, in accordance with an embodiment. The procedure or treatment performed by a dental practitioner may be a prosthodontic (restorative) or orthodontic procedure. Procedures may also be simply performing a scan of a patients jaw, taking x-rays of a patient's jaw, taking other imaging data, cleaning a patient's teeth, or the like. While particular treatments and procedures are described herein, these are given as examples and the disclosure contemplates similar methods and processes for any dental treatments or procedures.

At block 1410 of method 1400, processing logic receives image data of a dental arch. For example, processing logic of an AR system may receive the image data from an image capture device. The image data may include a two dimensional image or video data. In some embodiments, the received image data may include stereoscopic image data generated from a variety of image capture devices.

At block 1420, processing logic determines an intraoral procedure or treatment to be performed on a tooth of the dental arch. At block 1430, processing logic detects a first area of interest in the image of the dental arch, wherein the first area of interest is associated with the intraoral procedure. The first area of interest may be determined using any of the aforementioned techniques, such as those described with reference to FIGS. 2-11. At block 1435, processing logic provides a visual overlay for output on a display of an augmented reality device identifying the first area of interest. The indicator for the AOI may be shown at a position of the AOI in a real-world view of the patient's dental arch as seen by a dental practitioner, and may identify the type of AOI and/or or other information about the AOI. In some embodiments, the AOI may be an area where a treatment or procedure is to be performed. The indicator for the AOI presented in the visual overlay may indicate the next step on the treatment or procedure, a location or target of a treatment or procedure, an indication of progress of a treatment or procedure, and so on. The visual overlay may be generated using any of the aforementioned techniques.

At block 1438, processing logic receives updated image data of the dental arch. The updated image data may be received in the same format as the image data received in block 1410. For example, if stereoscopic images were received from image capture devices in block 1410, the same image capture device may provide the same image data format in block 1438. In some embodiments, different formats of image data may be received. For example, if the dental practitioner is partially or fully obscuring a portion of the view of the dental arch, the AR system may receive image data from a subset of image capture devices or from secondary image devices that were not previously used. Furthermore, in some embodiments, the update image data may include a CT scan, x-ray image data, or other image data than was received in block 1410.

At block 1440, processing logic determines whether the first area of interest is changed based on the updated image data and/or a comparison of the updated image data to the previously received image data. The first area of interest may change, for example, if the dental procedure is adding material to the dental arch or removing material from the dental arch. For example, if the dental procedure involves grinding one or more teeth, then the first area of interest may change if the tooth being ground corresponds to an area of interest. If the first area of interest has not changed than the method returns to block 1440. If the first area of interest has changed, then the method proceeds to block 1445.

At block 1445, processing logic identifies a change to the first area of interest during the intraoral procedure. At block 1450, processing logic determines an update to the visual overlay based on the change to the first area of interest. At block 1455, processing logic provides the updated visual overlay to the AR display. In an example, if the dental procedure is grinding a tooth, then the first area of interest highlighted in the visual overlay may show an area of the tooth to be ground in a color such as red. An area of the tooth that is not to be ground may be shown in another color such as green. As the tooth is ground, the visual overlay may be updated to reflect the material that has been removed from the tooth. Additionally, if any portion of the tooth has been ground down to a predetermined finish area, then that portion of the area of interest may be shown in a contrasting color. This may enable a dental practitioner to more accurately grind down a tooth according to a treatment plan.

At block 1460, processing logic determines whether the dental procedure has been completed. The processing logic may determine the procedure is complete based on a detected change to the image data, based on feedback from the dental practitioner, based on a time change, or based on other criteria or indication. If the procedure or treatment is not complete, the processing logic may return to block 1438 and continue to receive updated image data and to provide updated overlay indicators based on the changes. If the procedure or treatment is determined to be complete, the AR system may end the method 1400. To end the method, the processing logic may indicate that the procedure or treatment is complete, remove indicators regarding the AOI, move on to a next procedure or treatment, stop updating the overlay, or perform other tasks.

The method 1400 described with reference to FIG. 14 may be used to implement a variety of dental procedures and treatments. As a non-limiting set of examples, the treatment or procedures discussed with reference to FIG. 14 may include placing attachments, interproximal reduction, computer tomography (CT) or x-ray scanning, cavity mapping, intraoral scanning, placement of a hole for implant, drilling, grinding, or any other dental treatment of procedure. In one example, the method 1400 described with reference to FIG. 14 may include a live update to an overlay of material to remove during an interproximal reduction procedure. The AR system may show an initial map of material to remove during the interproximal reduction.

Figure 15A:
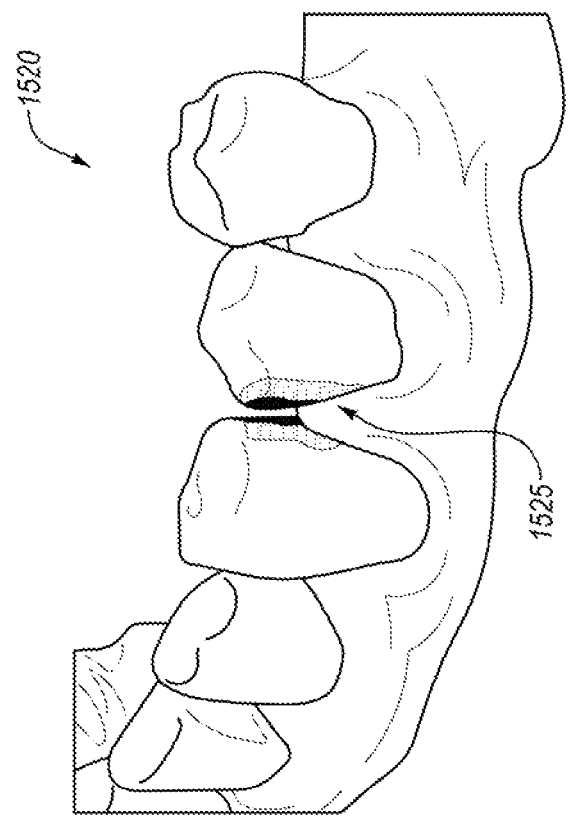
FIG. 15A illustrates a portion of an example augmented reality display showing areas of interest related to grinding a tooth, in accordance with an embodiment.
Figure 15B:
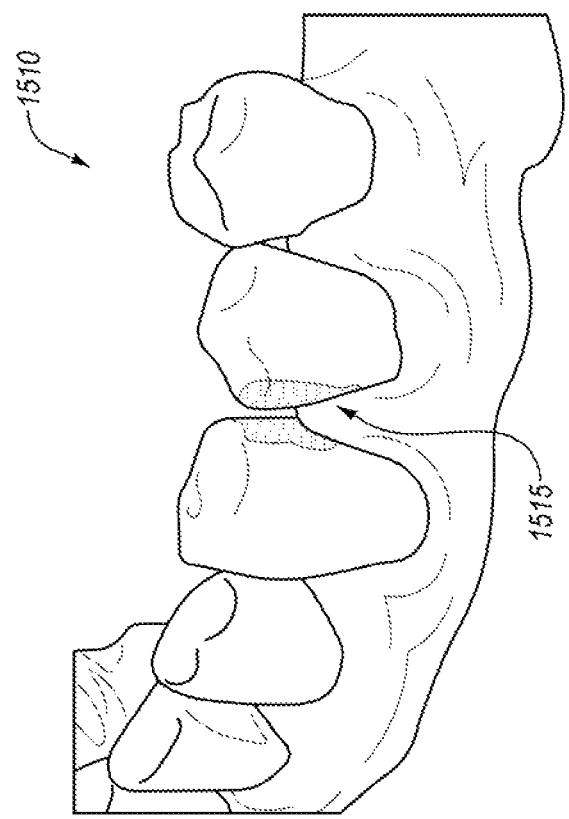
FIG. 15B illustrates a portion of an example augmented reality display showing areas of interest related to grinding a tooth, in accordance with an embodiment.

FIG. 15A illustrates an example portion 1510 of a view of an AR display showing a visual overlay with an indication 1515 of an amount of tooth to remove in an interproximal region between two teeth. The amount of tooth to remove may be determined based on a three dimensional model of the patient's dental arch as well as planned steps in an orthodontic treatment plan. As the dental practitioner removes material from the tooth, the AR system may receive additional updated image data of the dental arch. The AR system may then determine an amount of material that is still to be removed. Based on the amount of material and position of material to remove, the AR system may update the visual overlay to provide an indicator of a new amount of material to remove. In addition, the AR system may change a color of the overlay or provide an indication when the planned amount of material has been removed from the tooth. For example, FIG. 15B illustrates an example portion 1520 of a view of an AR display with an updated overlay based on the material removed from the tooth. The AR display in FIG. 15B includes an indication 1525 of an amount of material to remove and an indication of the amount of material that has been removed. In some embodiments, the indicator 1525 may instead change color gradually as material is removed. For example, the indicator 1515 may be completely green and gradually change colors until the planned amount of material has been removed. Then the indicator may turn red to indicate that the procedure is complete.

In another example, the method 1400 described with reference to FIG. 14 may include an update during x-ray scanning or intraoral scanning. For example, the AR system may determine areas with completed scanned data and overlay those areas with the scanned data. For example, the AR system may display to the dental practitioner live updates to scanned data as an overlay of the scanned data on the patient's dental arch. In some embodiments, the AR system may use highlighting instead of scanned data as an overlay to indicate either areas that have not been scanned or areas that have already been scanned.

Figure 16:
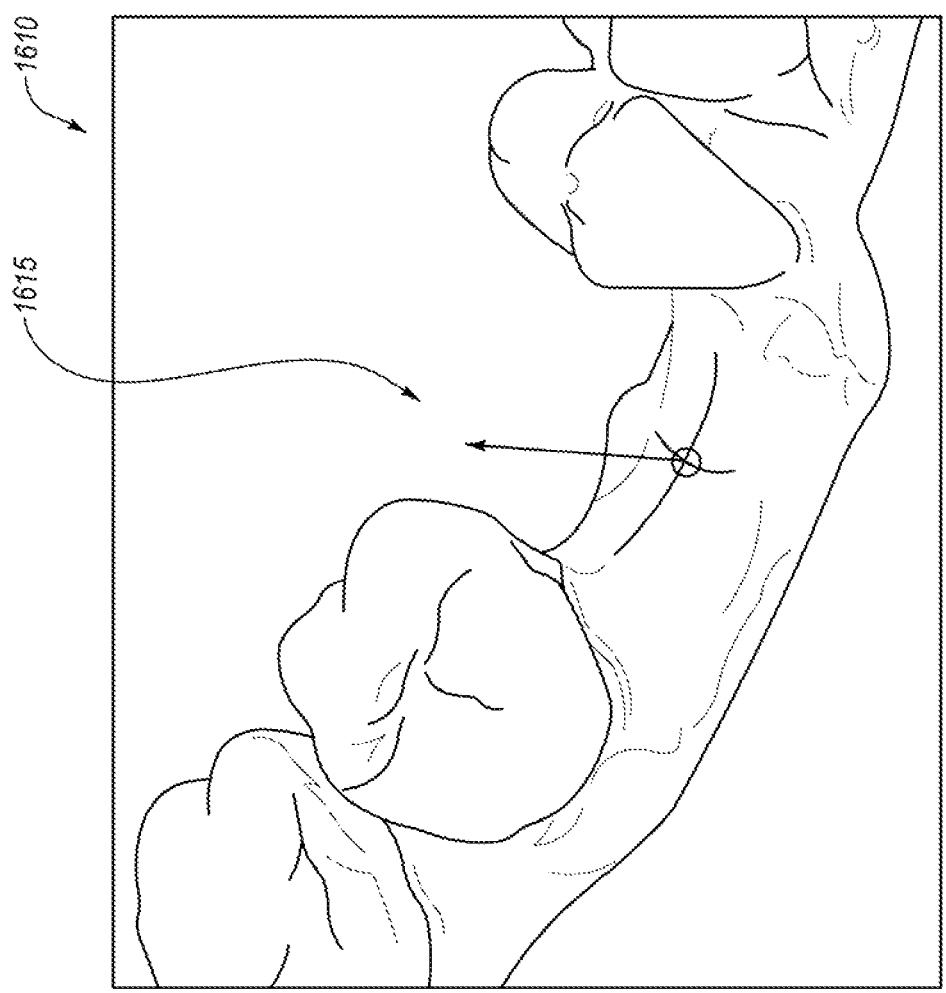
FIG. 16 illustrates a view of an example augmented reality display showing areas of interest related to an insertion path for a dental implant, in accordance with an embodiment.

In another example, the AR system may perform a method 1400 as described with reference to FIG. 14 to indicate to a dental practitioner an indication of placement of an attachment or ideal placement of a hole for an implant. For example, the AR system may access a three dimensional model of the patient's dentition and use that model to identify an ideal placement of an attachment or a hole for an implant. The AR system may identify the placement based on automated analysis of the three dimensional model, or based on planned positions indicated on the three dimensional model. FIG. 16 depicts an example of a portion 1610 of an AR display showing an indicator 1615 of a placement of a hole for an implant to a dental practitioner. The indicator 1615 shows a placement of a hole and a direction that the hole should be drilled. Similar indications may be provided for placement of an attachment. For example, the AR system may place an outline of the position of the attachment on a tooth. The AR system may then update the color of the outline based on analysis of image data to recognize placement of the attachment.

Figure 17A:
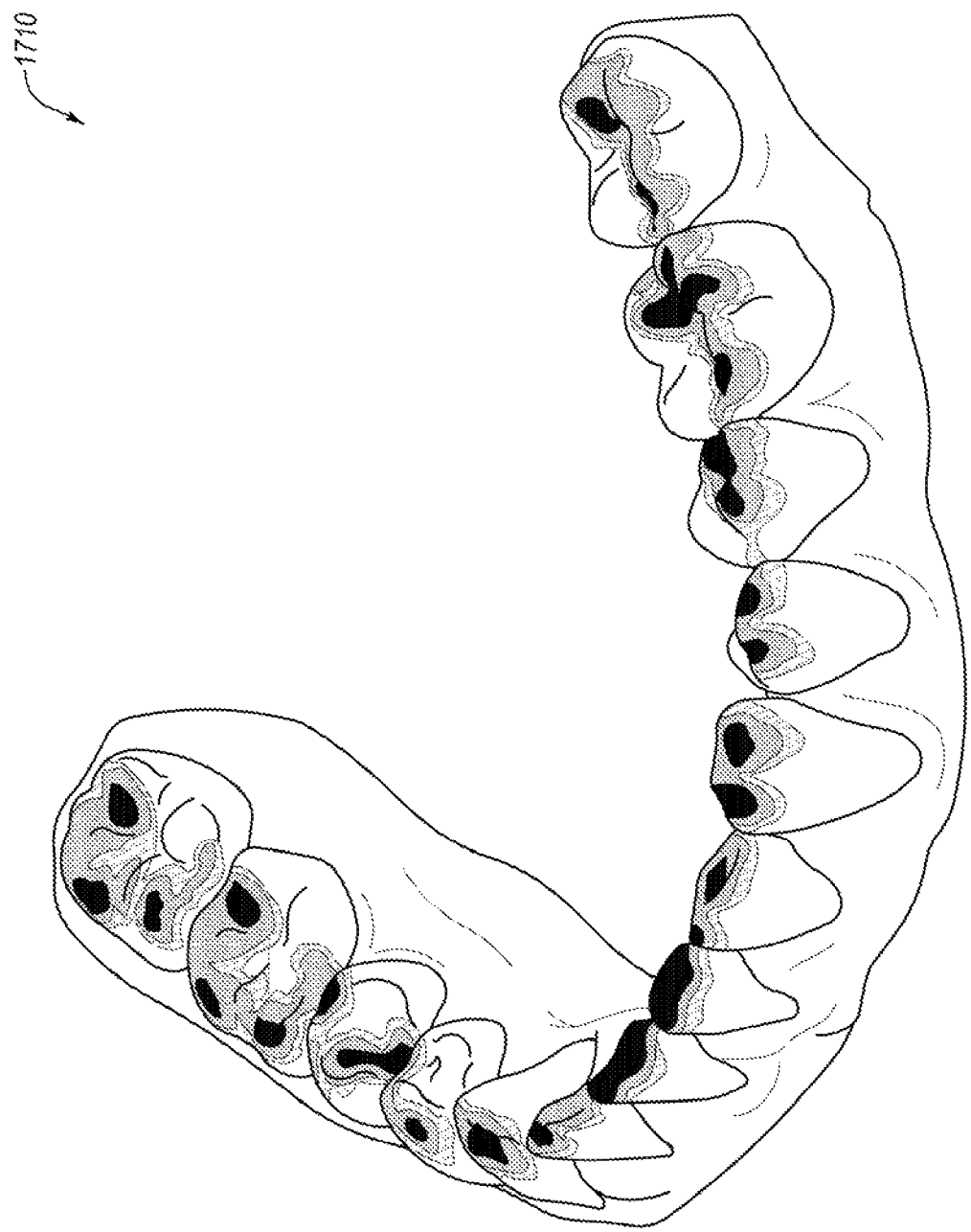
FIG. 17A illustrates a portion of an example augmented reality display showing areas of interest that identify an occlusion map, in accordance with an embodiment.

FIG. 17A is an example of a portion 1710 of an AR display showing a live occlusion map for a patient. In some embodiments, the AR system may generate an occlusion map based on analysis of contacts between the lower and upper jaw portions of a patient. For example, the occlusion map may be generated from three dimensional models captured during a current session or from a previous treatment, procedure or scan. The AR system may then match the occlusion map to a feature detected in image data received by an image capture device. In some embodiments, the AR system may also update an occlusion map during a treatment or procedure by a dental practitioner. For example, if a dental practitioner identifies an issue with an occlusion map (e.g., disruptive contacts) the dental practitioner may determine that grinding a portion of one or more contacts may improve the patient's bite. Accordingly, the dental practitioner may begin grinding a portion of a contact to improve the overall points of a patient's bite. The AR system may receive updated image data from the image capture device and determine a change in the shape of one or more teeth where the dental practitioner performed grinding. The AR system may then calculate or receive a new occlusion map based on the updated shape of teeth. The AR system may then overlay the updated occlusion map on the dental arch of a patient on the AR display to show changes to contacts. The dental practitioner may then determine when to stop grinding based on updates to the occlusion map. In some embodiments, the AR system may also indicate to the dental practitioner when to stop grinding based on a planned outcome for the occlusion map or the occlusion map meeting a particular threshold for placement of contacts.

Figure 17B:
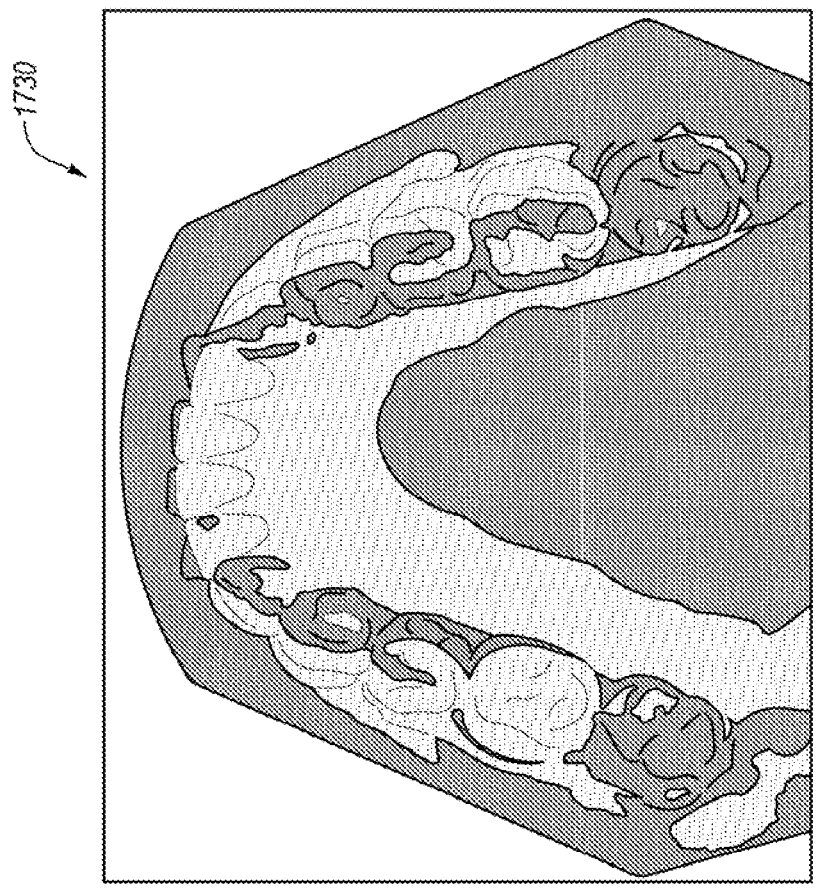
FIG. 17B illustrates a view of an example augmented reality display showing actual teeth movement vs. target teeth movement for a treatment plan, in accordance with an embodiment.
Figure 17B:
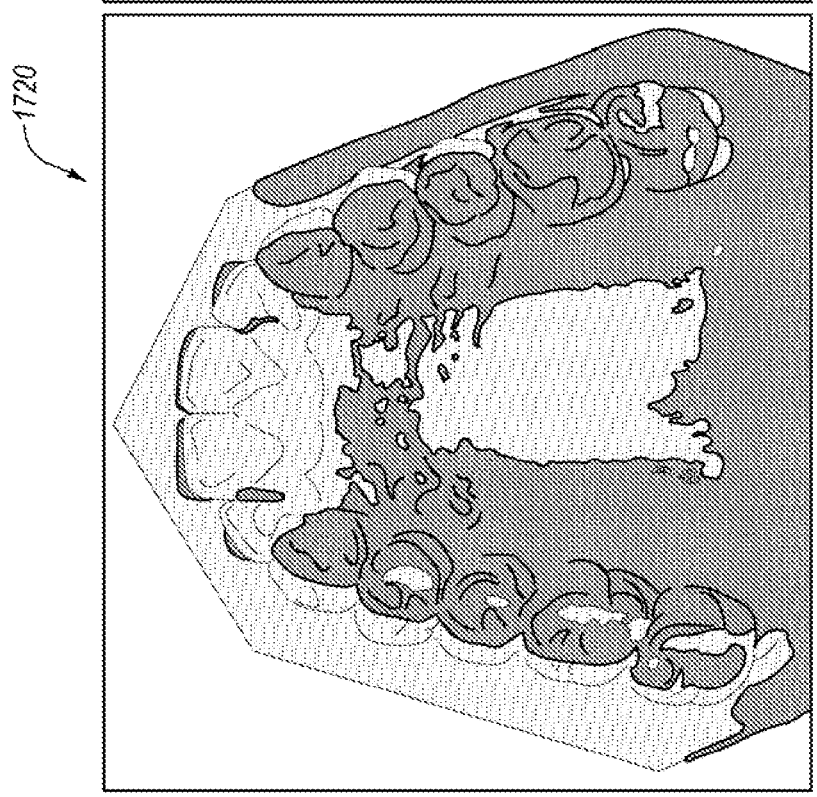

FIG. 17B illustrates a patient's upper dental arch 1730 and lower dental arch 1720 from current image data with a visual overlay showing actual tooth movement compared to target tooth movement from a treatment plan. Teeth that have moved according to the treatment plan may be shown in the visual overlay with a first color, line type or fill type and teeth that have not moved according to the treatment plan may be shown with a second color, line type or fill type. Alternatively, portions of the teeth that are outside of a target region may be shown with the first color, while portions of the teeth that are within a target region may be shown with a second color.

Figure 18:
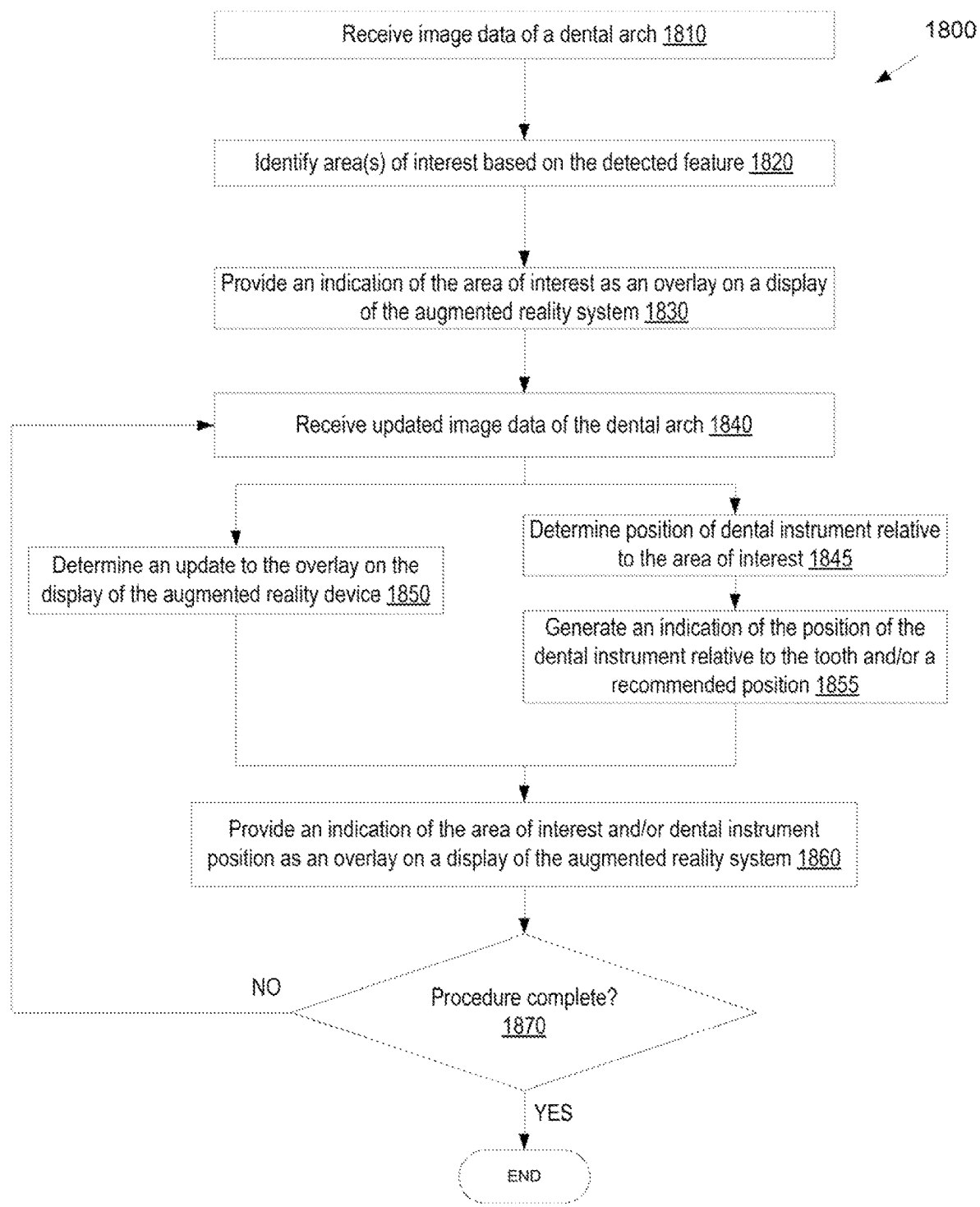
FIG. 18 illustrates a flow diagram for a method of determining areas of interest by an augmented reality device, in accordance with an embodiment.

FIG. 18 illustrates a flow diagram for a method 1800 of determining areas of interest by an augmented reality device, in accordance with an embodiment. Method 1800 is a process for generating overlay information for display on an AR display during a treatment or procedure performed by a dental practitioner using a dental instrument. The procedure or treatment performed by a dental practitioner may be prosthodontic (restorative) or orthodontic procedures. Procedures may also be performing a scan of a patients jaw, taking x-rays of a patient's jaw, taking other imaging data, cleaning a patient's teeth, placing an implant, grinding a patient's tooth, or the like. While particular treatments and procedures are described herein, these are given as examples and the disclosure contemplates similar methods and processes for any dental treatments or procedures.

Beginning in block 1810 an AR system receives image data of a dental arch. For example, the AR system may receive the image data from an image capture device.

In block 1820, the AR system identifies one or more areas of interest based on a detected feature. For example, the AR system may identify areas of interest according to methods as described above with reference to FIGS. 2-11. In some embodiments, areas of interest may be identified using other methods or processes. The AR system may store the areas of interest with an indicator of a type of area of interest and position of the area of interest. For instance, coordinates in a three dimensional model may be used to store a position of the area of interest.

In block 1830, the AR system overlays an indication of the AOI on an AR display. The indication overlay may be positioned on the AR display so as to appear in the position of the AOI on the dental arch as viewed by a dental practitioner wearing the AR display. The indication may mark the AOI with a color or other indicator to highlight the AOI for the dental practitioner. The indicator may also show the type of AOI, or other information about the AOI. In some embodiments the AOI may be an area where a treatment or procedure is to be performed. The indicator presented on the AR display may indicate the next step on the treatment or procedure, a location or target of a treatment or procedure, or an indication of progress of a treatment or procedure.

In block 1840, the AR system receives updated image data of the dental arch. The image data may be received in the same format as the image data received in block 1810. For example, if stereoscopic images were received from image capture devices in block 1810, the same image capture device may provide the same image data format in block 1810. In some embodiments, different formats of image data may be received. For example, if the dental practitioner is partially or fully obscuring a portion of the view of the dental arch, the AR system may receive image data from a subset of image capture devices or from secondary image devices that were not previously used. Furthermore, in some embodiments, the update image data may include CT scan, x-ray image data, or other image data than was received in block 1810.

The AR system may then determine an update based on the updated image data and determine a position of a dental instrument used during the procedure or treatment. In the first aspect, in block 1850, The AR system determines an update to the overlay on the display of the AR system. For example, the AR system may compare the updated image data to previously received image data. Based on the comparison, the AR system may identify an update to an AOI. The AR system may then determine an update to the indicator of the AOI and provide that update to the AR display so that the dental practitioner is presented with the updated overlay.

The AR system may also continue in block 1845 to determine a position of a dental instrument relative to the AOI. The AR system may determine the position of the dental instrument based on a sensor in the dental instrument and/or based on a position of the dental instrument in the updated image data received by the AR system. The position of the dental instrument may be detected with six degrees of freedom to indicate a position and rotation within three dimensional space. In some embodiments, the AR system may also correlate the position of the dental instrument to a planned position for treatment or procedures performed by the dental practitioner.

The AR system may then continue in block 1855 to generate an indication of the position of the dental instrument relative to the tooth position and/or a recommended or planned position of the dental instrument. For example, in some embodiments, the AR system may generate an indication of a preferred position of a drill during an implant operation. The indication may provide an indication to the dental practitioner whether the instrument is in a proper position.

In block 1860, the AR system may provide an indication of a change to the area of interest and/or the position of the dental instrument on an AR display. The indication overlay may be positioned on the AR display so as to appear in the position of the AOI on the dental arch. For example, the AR system may project an indication of the change to the AOI or to the position of the dental instrument onto each lens in the frame of a set of AR glasses. The indication may mark the AOI with a color or other indicator to highlight the AOI for the dental practitioner. The indicator may also show the type of AOI, or other information about the AOI.

The AR system may continue in block 1870 to determine whether the treatment or procedure is complete. The AR system may determine the procedure is complete based on a detected change to the image data, based on feedback from the dental practitioner, based on a time change, or based on other criteria or indication. If the procedure or treatment is not complete, the AR system may continue to receive updated image data and to provide updated overlay indicators based on the changes. If the procedure or treatment is determined to be complete, the AR system may end the method 1800. To end the method, the AR system may indicate that the procedure or treatment is complete, remove indicators regarding the AOI, move on to a next procedure or treatment, stop updating the overlay, or perform other tasks.

The method 1800 described with reference to FIG. 18 may be used to implement a variety of dental procedures and treatments. As a non-limiting set of examples, the treatment or procedures discussed with reference to FIG. 18 may include placing attachments, interproximal reduction, CT or x-ray scanning, intraoral scanning, cavity mapping, placement of a hole for implant, drilling, grinding, or any other dental treatment of procedure.

In one example implementation, the AR system may perform operations as described with reference to FIG. 18 to provide control or provide feedback to operations of a dental drill during a treatment or procedure performed by a dental practitioner. In some embodiments, the drill used by a dental practitioner may include a sensor to determine the position and orientation of the dental drill in relation to the AR system. In some embodiments, the drill may include a visual marker to indicate the orientation of the dental instrument. For example, a QR code, a barcode, or another visual indicator may be indicated by a visual marker on the dental drill.

The AR system may then use the orientation and position of a dental drill in relation to an identified AOI to determine whether the drill is in a position relative to the AOI to perform the appropriate treatment or procedure. If the dental drill is not in the correct position or orientation, the AR system may display on an AR display that the position is not in the correct position. In some embodiments, the AR system may issue instructions to the dental drill to stop the dental drill from operating until the dental drill is in the correct position and orientation.

In some embodiments, the AR system may also mark adjacent undercuts or implant sites for particular procedures. Furthermore, the AR system may also indicate particular areas that may have cavities, tooth wear, or other issues that are being addressed by the current procedure or treatment. Moreover, if the dental drill has reached a particular depth as calculated by the AR system, the AR system may cause the drill to stop operating or to stop operating until an override instruction is issued by a dental practitioner.

Figure 19:
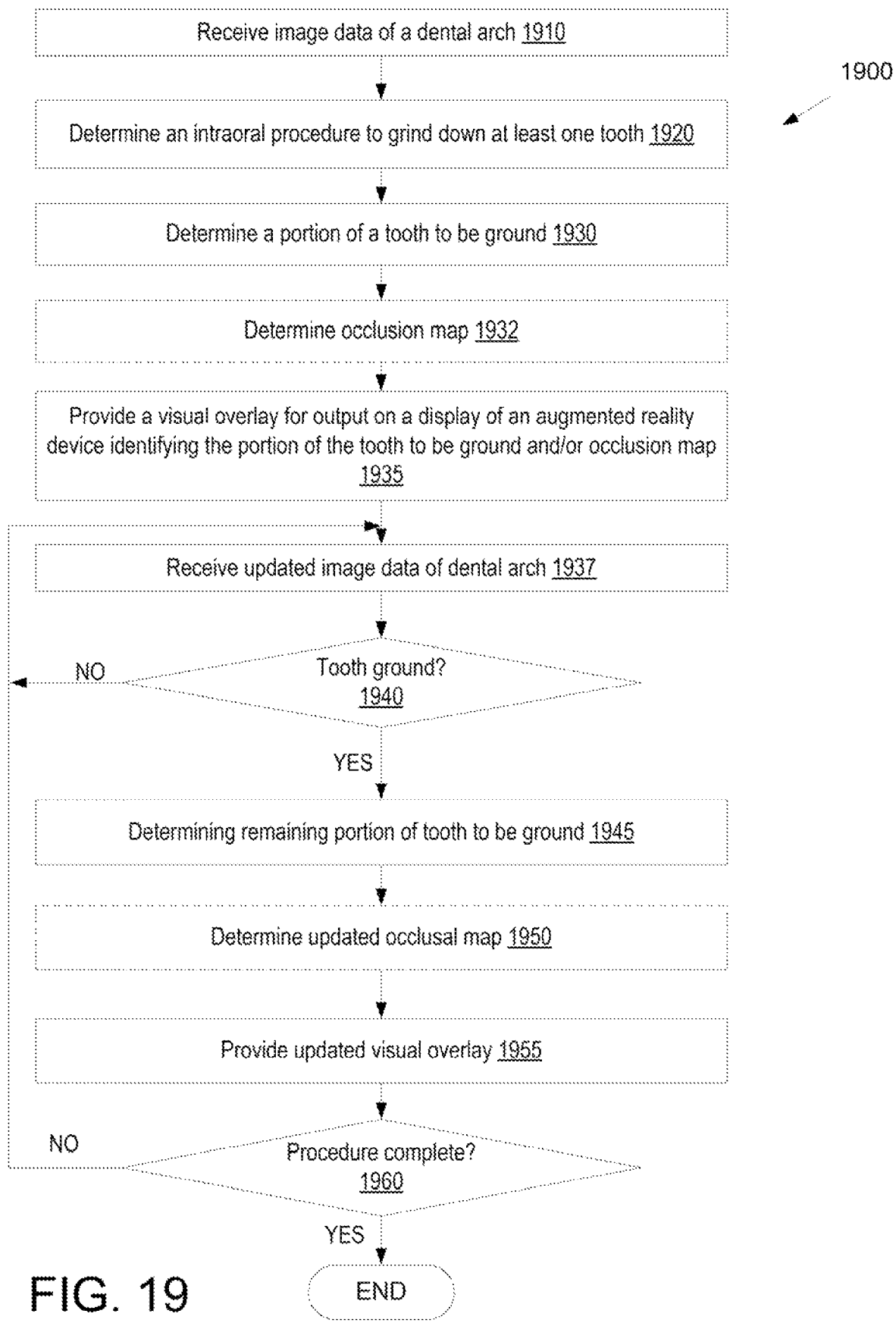
FIG. 19 illustrates a flow diagram for a method of providing a visual overlay in an image on an augmented reality device that provides information about a procedure to grind a tooth, in accordance with an embodiment.

FIG. 19 illustrates a flow diagram for a method 1900 of providing a visual overlay in a view on an augmented reality display that provides information about a procedure to grind a tooth, in accordance with an embodiment. At block 1910 of method 1900, processing logic receives image data of a dental arch from an image capture device of an augmented reality device. At block 1920, processing logic determines an intraoral procedure to grind down at least one tooth to correct a malocclusion or for another purpose. At block 1930, processing logic determines a portion of a tooth to be ground. At block 1932, processing logic may determine an occlusion map. At block 1935, processing logic provides a visual overlay for output on the display of the augmented reality device. The visual overlay identifies the portion of the tooth to be ground and/or may identify the occlusion map.

At block 1937, processing logic receives updated image data of the dental arch. At block 1940, processing logic determines whether any portion of the tooth has been ground based on processing the updated image data. If no portion of the tooth has been ground, then the operation of block 1940 is repeated. If the tooth has been ground, then the method proceeds to block 1945. At block 1945, processing logic determines the remaining portion of the tooth to be ground. At block 1950, processing logic may determine an updated occlusion map based on the portion of the tooth that has been ground. The updated occlusion map may be determined by adjusting a three-dimensional model that includes an upper arch, a lower arch, and the contact points of teeth between the upper arch and lower arch. At block 1955, processing logic provides an updated visual overlay.

At block 1960, processing logic determines whether the dental procedure has been completed. The processing logic may determine the procedure is complete based on a detected change to the image data, based on feedback from the dental practitioner, based on a time change, or based on other criteria or indication. If the procedure or treatment is not complete, the processing logic may return to block 1937 and continue to receive updated image data and to provide updated overlay indicators based on the changes. If the procedure or treatment is determined to be complete, the AR system may end the method 1900. To end the method, the processing logic may indicate that the procedure or treatment is complete, remove indicators regarding the AOI, move on to a next procedure or treatment, stop updating the overlay, or perform other tasks.

Figure 20:
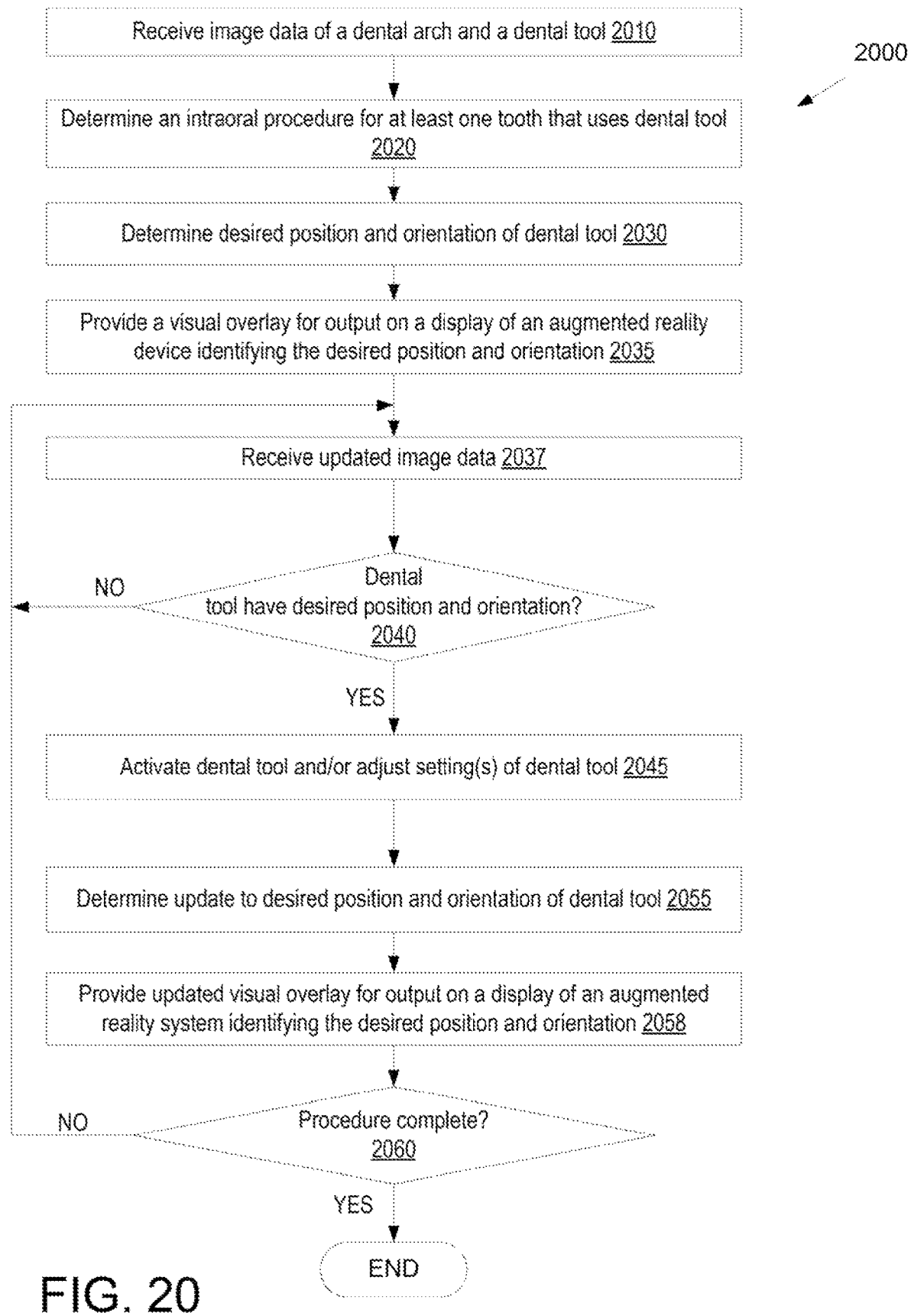
FIG. 20 illustrates a flow diagram for a method of providing a visual overlay with information that augments use of a dental tool, in accordance with an embodiment.

FIG. 20 illustrates a flow diagram for a method 2000 of providing a visual overlay in an image on an augmented reality display that provides information that augments use of a dental tool (also referred to herein as a dental instrument), in accordance with an embodiment. At block 2010 of method 2000, processing logic receives image data of a dental arch from an image capture device of an augmented reality device. The received image data includes an image of a dental tool being used by a dental practitioner to perform an intraoral procedure. At block 2020, processing logic determines an intraoral procedure for at least one tooth, where the intraoral procedure uses the dental tool.

At block 2030, processing logic determines a desired position and orientation of the dental tool. At block 2035, processing logic provides a visual overlay for output on the display of an augmented reality device identifying the desired position and orientation. At block 2037, processing logic receives updated image data, where the updated image data includes a current position and orientation of the dental tool.

At block 2040, processing logic determines based on the updated image data whether the dental tool has the desired position and orientation. If the dental tool does not have the desired position and orientation, then the method returns to block 2040. If the dental tool does have the desired position and orientation, then the method proceeds to block 2045.

At block 2045, processing logic may activate the dental tool and/or adjust one or more settings of the dental tool. Additionally, processing logic may output a command to a haptic device such as haptic gloves or a haptic module of the dental tool to cause the haptic device to provide a haptic feedback to the dental practitioner to indicate that the dental tool has reached the desired position and orientation.

At block 2055, processing logic determines an update to the desired position and orientation of the dental tool. At block 2058, processing logic provides an updated visual overlay for output on the display of the augmented reality device identifying the desired position and orientation. At block 2060, processing logic determines whether the dental procedure has been completed. If the procedure or treatment is not complete, the processing logic may return to block 2037 and continue to receive updated image data and to provide updated overlay indicators based on the changes. If the procedure or treatment is determined to be complete, the method may end.

Figure 21:
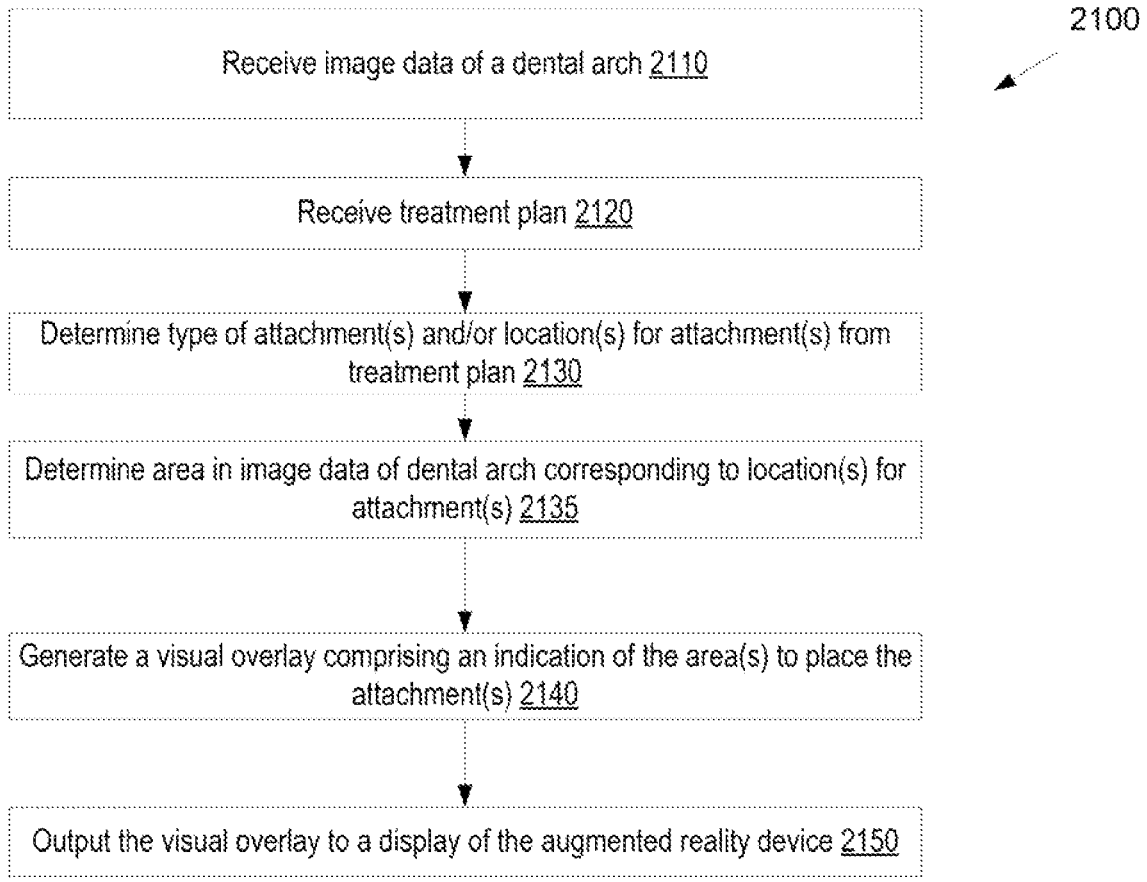
FIG. 21 illustrates a flow diagram for a method of facilitating placement of attachments on a patient's teeth using an augmented reality device, in accordance with an embodiment.

FIG. 21 illustrates a flow diagram for a method 2100 of facilitating placement of attachments on a patient's teeth using an augmented reality device, in accordance with an embodiment. At block 2110 of method 2100, processing logic receives image data of a dental arch from an augmented reality devices' image capture device. At block 2120, processing logic receives a treatment plan. The treatment plan may be, for example, an orthodontic treatment plan that indicates forces to be applied to teeth at various stages of treatment. Some types of forces may be improved by adding attachments to teeth. For example, attachments may improve some rotational forces on teeth.

At block 2130, processing logic determines a type of attachment and/or location for the attachment from the treatment plan. At block 2135, processing logic determines an area in the image data of the dental arch corresponding to locations for the attachments. At block 2140, processing logic generates a visual overlay comprising an indication of the areas to place the dental attachments. At block 2150, processing logic outputs the visual overlay to a display of the augmented reality device. The visual overlay may be superimposed over a view of the dental arch as viewed by the dental practitioner on the display at the position of the area of interest. Accordingly, the dental practitioner may see in an augmented reality display an indication of where to place an attachment.

Figure 22:
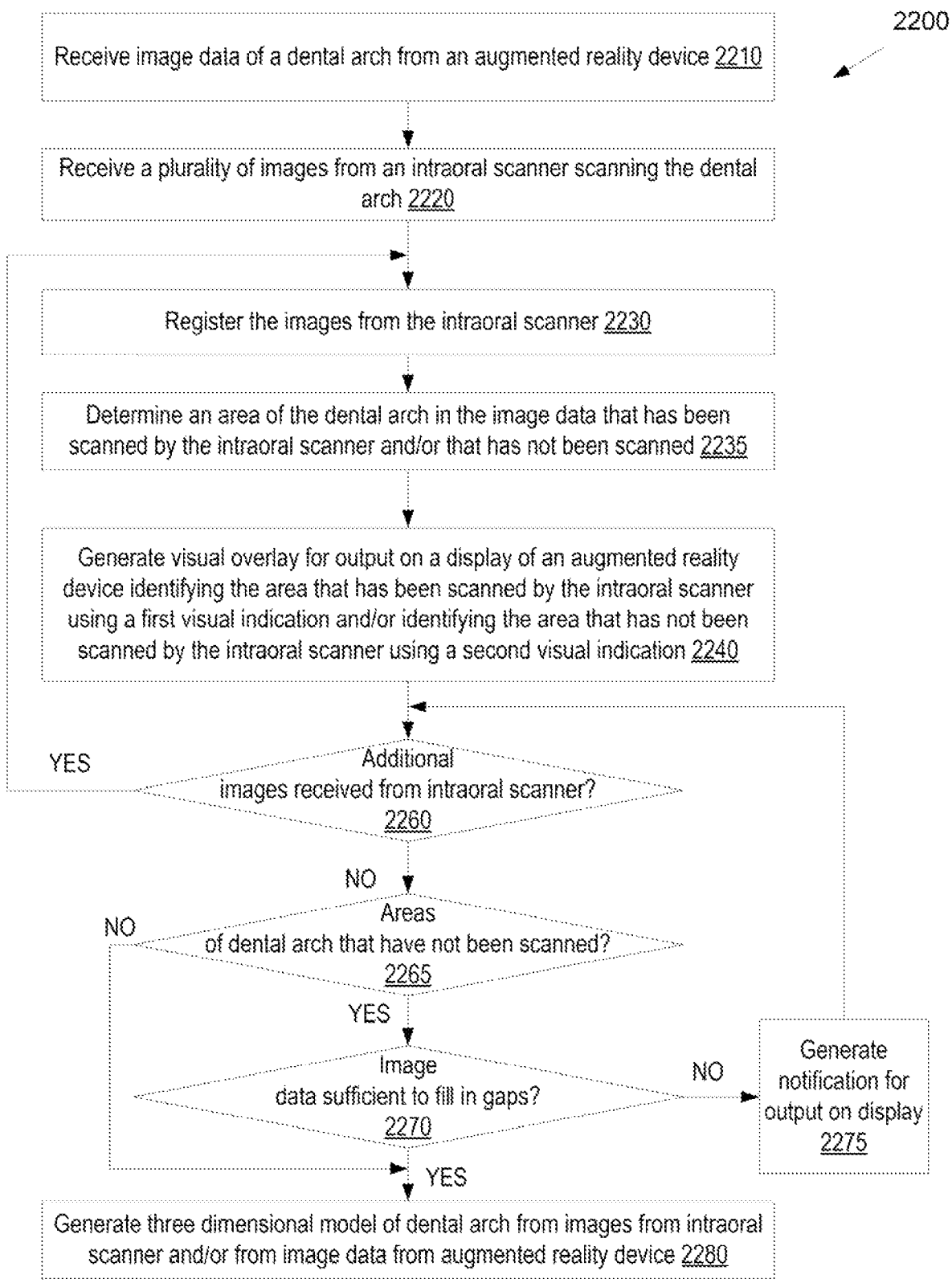
FIG. 22 illustrates a flow diagram for a method of facilitating an intraoral scan session using an augmented reality device, in accordance with an embodiment.

FIG. 22 illustrates a flow diagram for a method 2200 of facilitating an intraoral scan session using an augmented reality device, in accordance with an embodiment. At block 2210 of method 2200, processing logic receives image data of a dental arch from an image capture device of an augmented reality device. At block 2220, processing logic receives a plurality of images from an intraoral scanner scanning the dental arch. At block 2230, processing logic registers the image from the intraoral scanner. This may include stitching images from the intraoral scanner together to build a model of the dental arch.

At block 2235, processing logic determines an area of the dental arch in the image data that has been scanned by the intraoral scanner and/or that has not been scanned. At block 2240, processing logic generates a visual overlay for output on the display of an augmented reality display identifying an area that has been scanned by the intraoral scanner using a first visual indication (e.g., a first color) and/or identifying an area that has not been scanned by the intraoral scanner using a second visual indication (e.g., a second color). Processing logic may additionally or alternatively perform an analysis of the scanned regions from the intraoral scan data to identify any dental conditions. AOIs identifying these dental conditions may then be determined and shown in the visual overlay. This enables a dental practitioner to immediately see any possible dental conditions during an intraoral scan session.

At block 2260, processing logic determines whether additional images have been received from the intraoral scanner. If additional images have been received from the intraoral scanner, the method returns to block 2230, and those additional images are registered to the previous intraoral images generated by the intraoral scanner. If no additional images are received, then the method continues to block 2265.

At block 2265, processing logic determines whether there are any areas of the dental arch that have not been scanned. For example, a dental practitioner may inadvertently skip over certain portions or regions of the dental arch during a scanning session. Such areas may be highlighted in the visual overlay. Accordingly, processing logic is capable of quickly identifying any holes in the image data (and thus the virtual 3-D model) of the dental arch. If there are no un-scanned areas of the dental arch, then the method proceeds to block 2280. If there are un-scanned areas of the dental arch, then the method continues to block 2270.

At block 2270, processing logic determines whether the image data from the augmented reality device's image capture device is sufficient to fill in gaps associated with un-scanned areas. For example, image data for an un-scanned area that is small and that is bordered by scanned areas on both sides may be provided based on image data from the augmented reality device's image capture device. However, if the view represented in the received image data is low quality or blocked by lips or other obstructions, or the un-scanned area is larger than a threshold size, then the received image data may be insufficient to fill in the gaps. If the received image data can be used to fill in the gaps, then the method continues to block 2280. If the image data cannot be used to fill the gaps, the method continues to block 2275.

At block 2275, processing logic generates a notification for output on the augmented reality display. The notification may indicate an area of interest that shows the un-scanned area. At block 2280, processing logic generates a three-dimensional model of the dental arch using the images from the intraoral scanner. Additionally, processing logic may use the received image data in addition to the data from the intraoral scanner to generate the three-dimensional model of the dental arch if there were small un-scanned areas that could be filled in using the image data.

Figure 23:
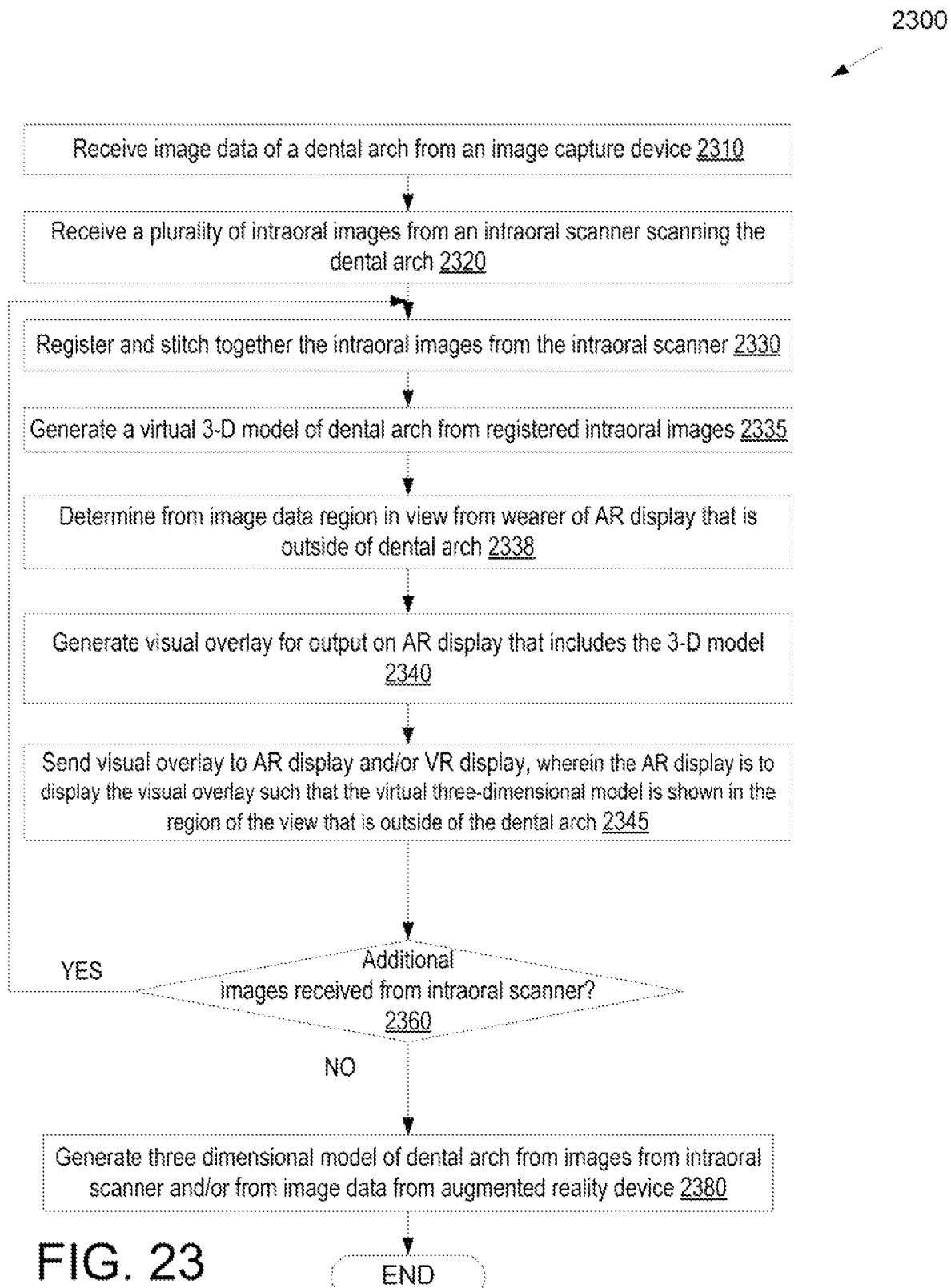
FIG. 23 illustrates a flow diagram for a method of using an augmented reality display for an intraoral scanner, in accordance with an embodiment.

FIG. 23 illustrates a flow diagram for a method 2300 of using an augmented reality display for an intraoral scanner, in accordance with an embodiment. At block 2310 of method 2300, processing logic receives image data of a dental arch from an image capture device of an augmented reality display. At block 2320, processing logic receives a plurality of intraoral images from an intraoral scanner scanning the dental arch.

At block 2330, processing logic registers the intraoral images together and stitches the intraoral images together based on the registration. In one embodiment, processing logic performs image registration for each pair of adjacent or overlapping intraoral images (e.g., each successive frame of an intraoral video). Image registration algorithms are carried out to register two adjacent intraoral images, which essentially involves determination of the transformations which align one image with the other. Image registration may involve identifying multiple points in each image (e.g., point clouds) of an image pair, surface fitting to the points of each image, and using local searches around points to match points of the two adjacent images. For example, processing logic may match points of one image with the closest points interpolated on the surface of the other image, and iteratively minimize the distance between matched points. Processing logic may also find the best match of curvature features at points of one image with curvature features at points interpolated on the surface of the other image, without iteration. Processing logic may also find the best match of spin-image point features at points of one image with spin-image point features at points interpolated on the surface of the other image, without iteration, Other techniques that may be used for image registration include those based on determining point-to-point correspondences using other features and minimization of point-to-surface distances, for example. Other image registration techniques may also be used.

Many image registration algorithms perform the fitting of a surface to the points in adjacent images, which can be done in numerous ways. Parametric surfaces such as Bezier and B-Spline surfaces are most common, although others may be used. A single surface patch may be fit to all points of an image, or alternatively, separate surface patches may be fit to any number of a subset of points of the image. Separate surface patches may be fit to have common boundaries or they may be fit to overlap, Surfaces or surface patches may be fit to interpolate multiple points by using a control-point net having the same number of points as a grid of points being fit, or the surface may approximate the points by using a control-point net which has fewer number of control points than the grid of points being fit. Various matching techniques may also be employed by the image registration algorithms.

In one embodiment, processing logic may determine a point match between images, which may take the form of a two dimensional (2D) curvature array. A local search for a matching point feature in a corresponding surface patch of an adjacent image is carried out by computing features at points sampled in a region surrounding the parametrically similar point. Once corresponding point sets are determined between surface patches of the two images, determination of the transformation between the two sets of corresponding points in two coordinate frames can be solved. Essentially, an image registration algorithm may compute a transformation between two adjacent images that will minimize the distances between points on one surface, and the closest points to them found in the interpolated region on the other image surface used as a reference.

Processing logic may repeat image registration for all adjacent image pairs of a sequence of intraoral images to obtain a transformation between each pair of images, to register each image with the previous one. At block 2335, processing logic then integrates all images into a single virtual 3D model of the dental arch being scanned by applying the appropriate determined transformations to each of the images. Each transformation may include rotations about one to three axes and translations within one to three planes.

At block 2338, processing logic determines from the image data a region in a view from a wearer of the AR display that is outside of the dental arch (and outside of an oral cavity that includes the dental arch). For example, if the dental practitioner is looking at a patient while he or she is performing an intraoral scan procedure, his field of view might also include the chair on which the patient is sitting, a portion of a room, and so on. At block 2340, processing logic generates a visual overlay for output on the AR display that includes the virtual 3-D model generated based on the received intraoral images. The virtual 3-D model may be a partial model of the patient's dental arch based on intraoral images so far received.

At block 2345, processing logic sends the visual overlay to the AR display worn by the dental practitioner. Additionally, processing logic may send the visual overlay to a VR display worn by the patient. The AR display displays the visual overlay such that the virtual 3-D model of the dental arch is shown in the region of the view for the dental practitioner that is outside of the dental arch (and oral cavity). That way the virtual 3-D model does not obstruct a view of the patient's oral cavity. The dental practitioner may interact with the virtual 3-D model using controls on the intraoral scanner (e.g., a touch interface on the intraoral scanner) or other input mechanisms such as motion controls. For example, the dental practitioner may wear haptic gloves, use a haptic wand, or use another haptic device. The user may "touch" the virtual 3-D model with the haptic device, which may cause a force feedback when the user "touches" the 3-D model. The user may interact with the virtual 3-D model to rotate the virtual 3-D model, zoom in or out on the virtual 3-D model, reposition the virtual 3-D model in the dental practitioner's field of view, and so forth. Based on the user input, processing logic may generate a new virtual overlay showing the virtual 3-D model with the new orientation, new zoom setting, new position in the dental practitioner's field of view, and so on.

At block 2360, processing logic determines whether any additional intraoral images have been received from the intraoral scanner. If new intraoral images are received, the method returns to block 2330, and the new intraoral images are registered and stitched together with the previous intraoral images. The virtual 3-D model is then updated to incorporate the new image data. Accordingly, the virtual 3-D model may grow and become more complete as the patient's dental arch is scanned. At any time the dental practitioner may refer to the virtual 3-D model in his field of view to determine whether there are any issues that need to be addressed, whether there are any regions that should be rescanned or that have not been scanned, and so on.

If at block 2360 no additional intraoral images are received, and the dental practitioner indicates that the scan is complete, the method proceeds to block 2380. At block 2380, processing logic generates a virtual 3-D model of the dental arch from the intraoral images. This virtual 3-D model may be a more accurate and detailed virtual 3-D model than the one generated at block 2335. Similar algorithms may be used to generate both virtual 3-D models, but more iterations may be performed to refine the virtual 3-D model at block 2380, more processor resources may be used, and more time may be used to generate the final virtual 3-D model. The operations of blocks 2320-2360 may be performed during a scan mode of an intraoral scan application.

The operations of block 2380 may be performed during a processing mode of the intraoral scan application.

Figure 24A:
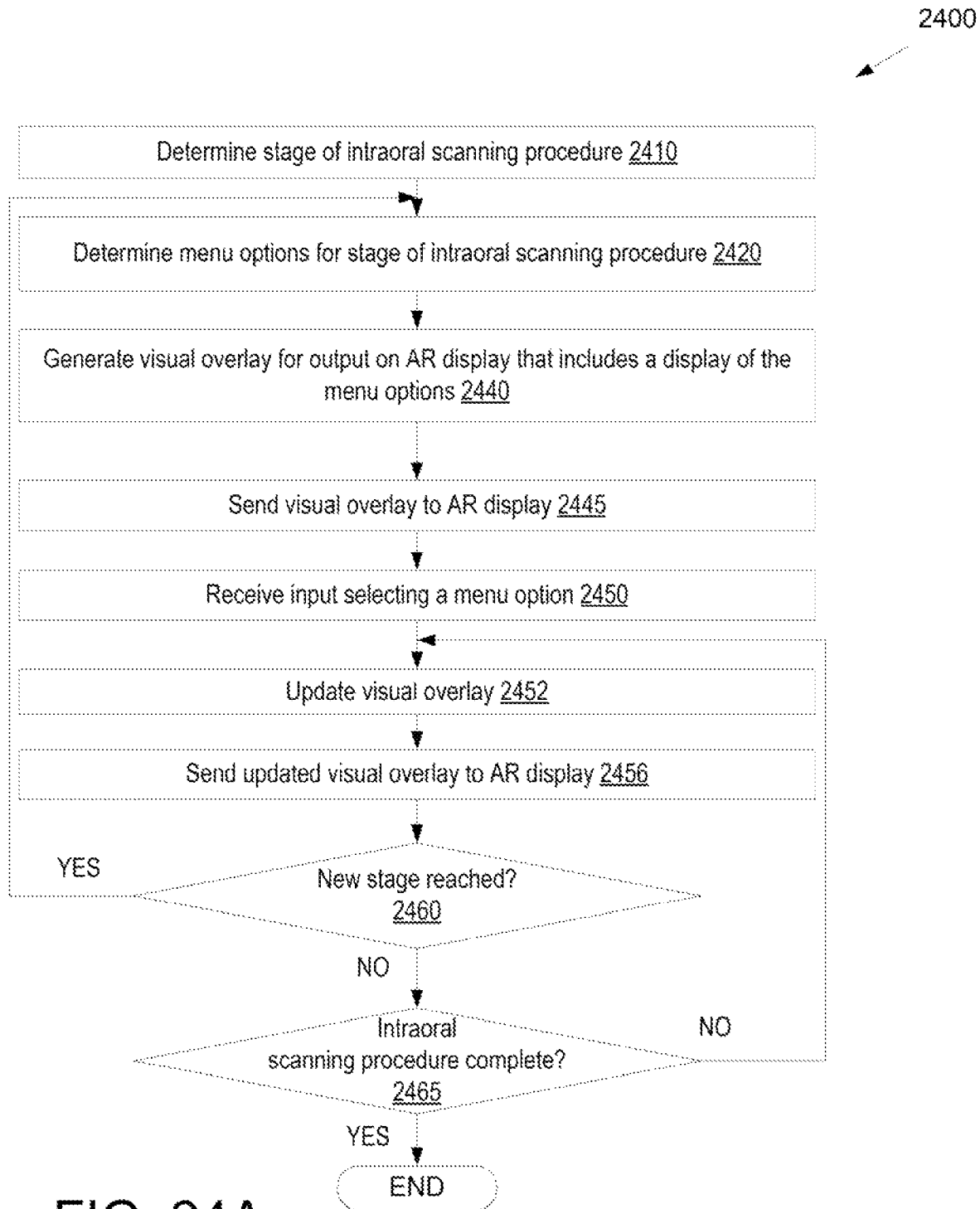
FIG. 24A illustrates a flow diagram for another method of using an augmented reality display for an intraoral scanner, in accordance with an embodiment.

FIG. 24A illustrates a flow diagram for another method 2400 of using an augmented reality display for an intraoral scanner, in accordance with an embodiment. At block 2410 of method 2400, processing logic determines a current stage or mode of an intraoral scanning procedure. At block 2420, processing logic determines menu options for the current stage or mode of the intraoral scan procedure. At block 2440, processing logic generates a visual overlay for output on an AR display, where the visual overlay includes a display of the menu options. The display of the menu options may be a 2-D display, a 3-D display, or a combination of 2-D display elements and 3-D display elements. The menu options may include, for example, a menu bar with different drop down menus, icons, and/or other graphical representations. Processing logic may place the menu of options in a fixed position on the virtual overlay, so that the menu is presented on an AR display worn by the dental practitioner at the same location in the dental practitioner's field of view regardless of what the menu might occlude from the dental practitioner's field of view. Alternatively, processing logic may receive image data from an image capture device of the AR display worn by the dental practitioner, and may determine whether the menu would obstruct the view of a patient. The position of the menu may then be adjusted so that it does not obstruct the view of the patient. For example, the menu may be repositioned from a top of the AR display to a side of the AR display.

At block 2445, processing logic sends the visual overlay to the AR display. At block 2450, processing logic receives an input selecting a menu option from the menu. The dental practitioner may use buttons, a touch input, or other input mechanism (e.g., a gyroscope and/or accelerometer that act as a motion input) from an intraoral scanner to select a menu option. The dental practitioner may also provide voice input to select the menu option.

At block 2452, processing logic updates the visual overlay based on the selected menu option. For example, the selected menu option may cause an intraoral scan application to change modes or stages (e.g., between a planning mode, a scan mode, a processing mode, and a transmission mode). The selected menu option may also cause additional menu options to be displayed (e.g., by expanding a drop down menu). The updated data is reflected in the update to the visual overlay. At block 2456, processing logic sends the visual overlay update to the AR display.

At block 2460, processing logic determines whether a new stage or mode of the intraoral scan procedure has been reached. If a new stage has been reached (e.g., based on user input selecting a next intraoral scan mode), the method returns to block 2420 and new menu options associated with the new stage or mode are determined. Otherwise the method proceeds to block 2465.

At block 2465, processing logic determines whether the intraoral scan procedure is complete. If the intraoral scan procedure is not complete, the method returns to block 2452. If the intraoral scan procedure is complete, the method ends.

Methods 2300 and 2400 may be used together to provide a virtual display for an intraoral scan application that is used in conjunction with an intraoral scanner to scan a patient's dental arches. The virtual display that is projected onto an AR display (e.g., an AR headset or AR goggles) has numerous advantages over a standard display shown on a computer screen. For example, the virtual display may appear much larger than a standard display. Additionally, the dental practitioner can view and interact with the virtual display without looking away from the patient. The virtual display can also be positioned anywhere in the field of view of the dental practitioner, such as over the patient's head, to the side of the patient's head, or wherever is convenient for the dental practitioner.

Figure 24B:
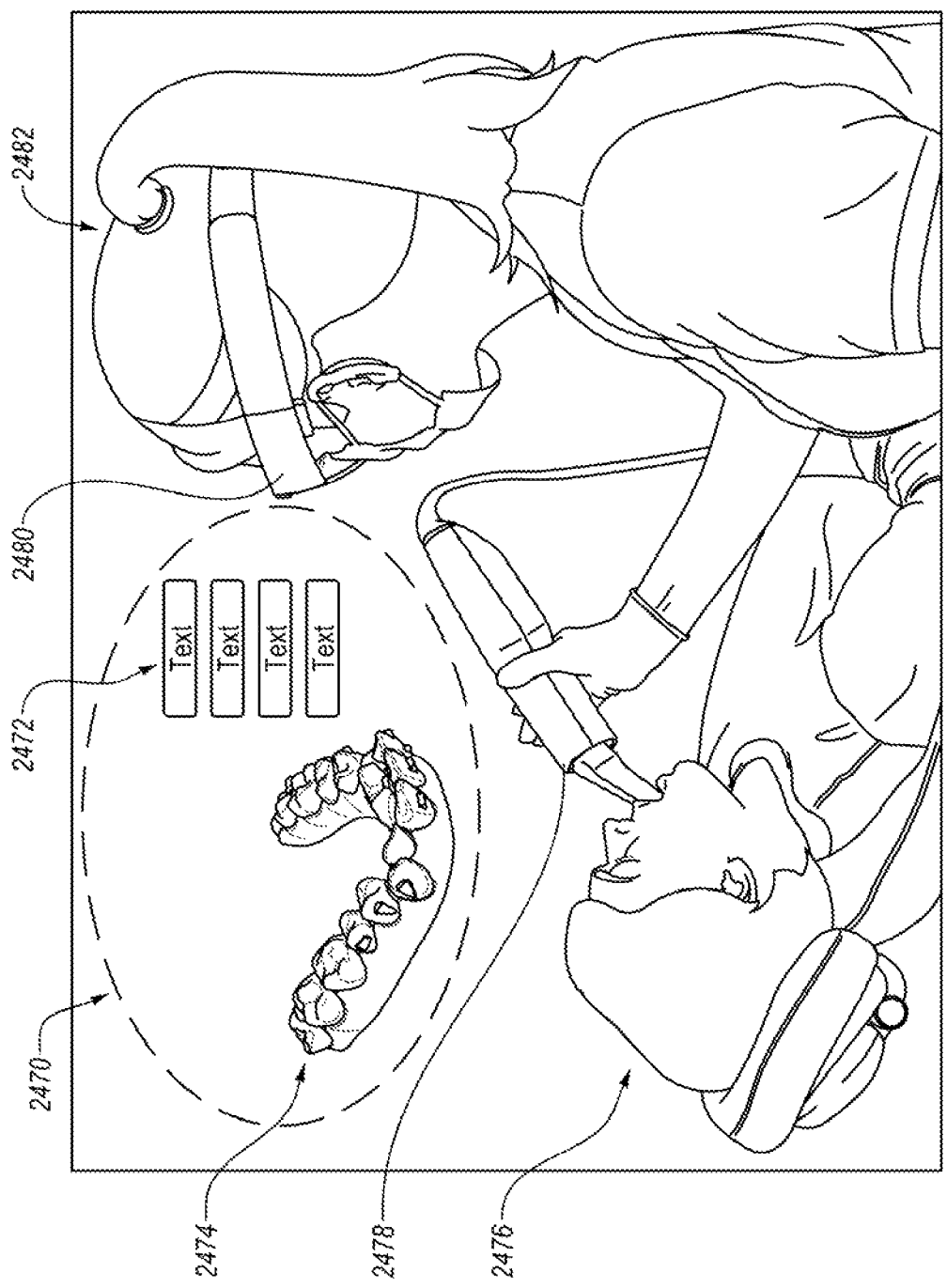
FIG. 24B illustrates a virtual display for an intraoral scan application that is displayed on an AR display, in accordance with an embodiment.

FIG. 24B illustrates a virtual display 2470 for an intraoral scan application that is displayed on an AR display, in accordance with an embodiment. As shown, a dental practitioner 2482 is wearing an AR display 2480 while using an intraoral scanner 2478 to scan an oral cavity of a patient 2476. The AR display 2482 displays the virtual display 2470 so that it appears to float over a head of the patient 2476. The virtual display 2470 for the intraoral scan application includes a menu 2472 that includes multiple menu options (e.g., as discussed with reference to method 2400) as well as a virtual 3-D model generated based on the intraoral scan (e.g., as discussed with reference to method 2300).

Figure 25A:
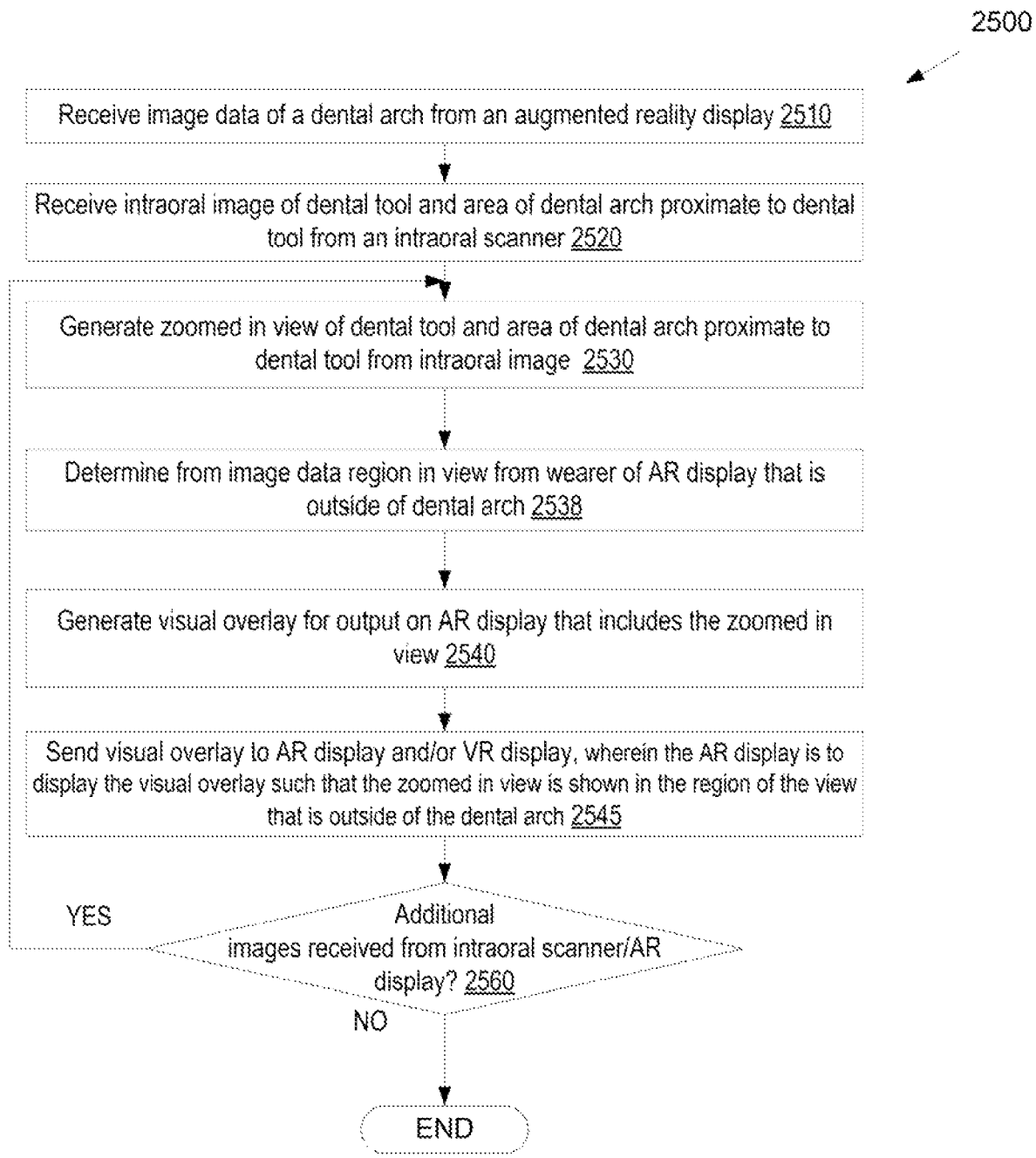
FIG. 25A illustrates a flow diagram for a method of using an augmented reality display and an intraoral scanner to provide a zoomed in view of a dental procedure, in accordance with an embodiment.

FIG. 25A illustrates a flow diagram for a method 2500 of using an augmented reality display and an intraoral scanner to provide a zoomed in view of a dental procedure, in accordance with an embodiment. At block 2510 of method 2500, processing logic receives image data of a dental arch from an image capture device of an AR display. At block 2520, processing logic receives an intraoral image of a dental tool and an area of the dental arch proximate to the dental tool. In one embodiment, the dental arch of the patient and the dental tool are first scanned using the intraoral scanner to generate virtual 3-D models of the dental arch and the dental tool. This may facilitate identifying regions of the dental arch and portions of the dental tool in later received images.

At block 2530, processing logic generates a zoomed in view of the dental tool and area of the dental arch proximate to the dental tool from the intraoral image. In one embodiment, processing logic determines an AOI from the intraoral image, and generates the zoomed in view (also referred to as an enlarged image or magnified image) of just the AOI. The AOI may include, for example, a region of the dental arch being operated on and a dental tool that is operating on the region of the dental arch. If 3-D models of the dental tool and the dental arch have previously been generated, this may enable processing logic to more quickly and easily determine a position and orientation of the dental tool relative to a particular tooth being operated on. Tracking accuracy can be on the order of 20-50 microns in embodiments.

At block 2538, processing logic determines from the image data received from the image capture device of the AR display a region in a view of a wearer of the AR display that is outside of the dental arch (and outside of an oral cavity). At block 2540, processing logic generates a visual overlay for output on the AR display that includes the zoomed in view. At block 2545, processing logic sends the visual overlay to the AR display. The AR display displays the visual overlay such that the zoomed in view is shown in the region of the wearer's field of view that is outside of the dental arch (and oral cavity). Thus, the zoomed in view of the dental procedure does not occlude a dental practitioner's actual real-world view of the dental procedure. In an example, a dental practitioner wearing the AR display may see both his patient and an enlarged image of the region in the patient's oral cavity where the dental practitioner is currently operating floating in the air above the patient. The enlarged image may include one or several teeth and a dental tool (e.g., a drill) being used. Processing logic may also send the visual overlay to a VR display worn by a patient. This enables the patient to also view the dental procedure as it is performed.

At block 2560, processing logic determines whether additional images have been received from the intraoral scanner and/or the AR display. In one embodiment, the intraoral scanner and the AR display each generate a stream of image data (e.g., a live video feed). Accordingly, additional images may be received from both the intraoral scanner and the AR display throughout the dental procedure. This enables the zoomed in view (enlarged image) of the teeth being operated on and the dental tool being used to be updated in real time so that it is in sync with the movements of the dental tool and progress of the dental procedure. The dental practitioner may determine how to manipulate the dental tool either by looking directly in the mouth of the patient (e.g., as the dental practitioner could do without wearing an AR display) or by looking at the enlarged image or zoomed in view displayed in the AR display. The large unobscured image (zoomed in view) of the area being operated on may make tooth manipulation and operation on the tooth significantly easier. For example, even slight motions of the dental tool can be identified in the magnified (enlarged) image. This enables slight modifications to be easily identified. Errors may be automatically detected and signaled as well. For example, undercuts or excessively large preparations that do not leave enough space for a new crown or bridge may be identified during the intraoral procedure. If no additional image data is received, and the dental procedure is completed, then the method ends.

In some embodiments, the image capture device of the AR display may capture images using different wavelengths. For example, the image capture device may generate infrared images, which may show data about the inside of a tooth being operated on (since teeth are transparent to light at the near-infrared spectrum).

In some embodiments, the images from the image capture device of the AR display and/or the images from the intraoral scanner generated during the intraoral procedure are recorded. These recorded images may act as a "black box recorder" that documents the actions of the dental practitioner so that someone can later learn from the dental procedure or identify what went wrong during the dental procedure.

Figure 25B:
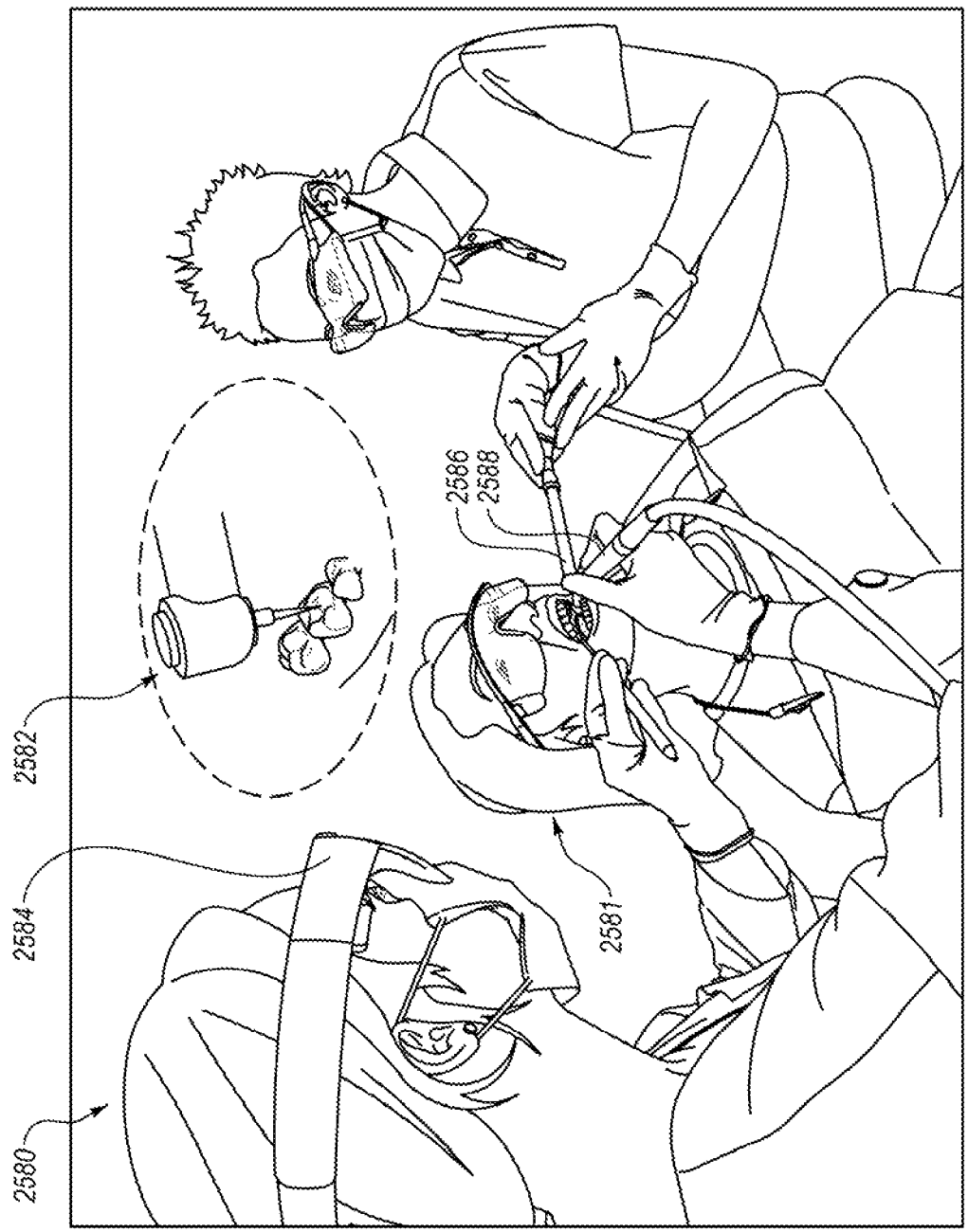
FIG. 25B illustrates a dental practitioner operating on a patient, in accordance with an embodiment.

FIG. 25B illustrates a dental practitioner 2580 operating on a patient 2581, in accordance with an embodiment. As shown, the dental practitioner 2580 is wearing an AR display 2584. The dental practitioner 2580 is using a dental tool 2588 to operate on a tooth of the patient 2581. An assistant is holding an intraoral scanner 2586 that is directed so as to image the dental procedure. Based on the images from the intraoral scanner, an enlarged image 2582 of the tooth being operated on and the dental tool 2588 performing the operation is generated and sent to the AR display 2584. The AR display 2584 displays the enlarged image 2582 so that it appears to be floating over a head of the patient 2581.

Figure 26:
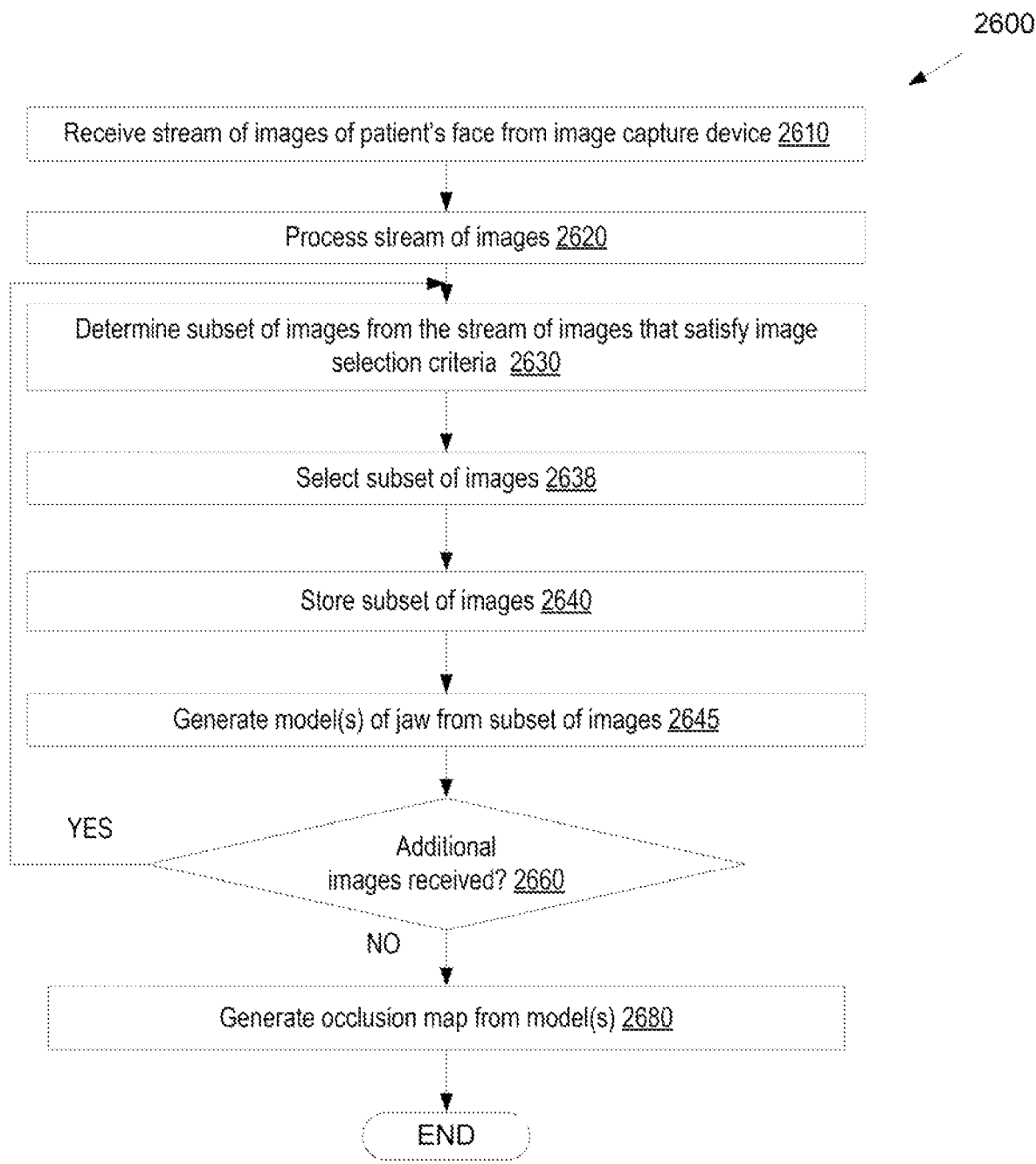
FIG. 26 illustrates a flow diagram for a method of generating a model for a dental arch from images captured by an image capture device associated with an augmented reality display, in accordance with an embodiment.

FIG. 26 illustrates a flow diagram for a method 2600 of generating a model for a dental arch from images captured by an image capture device associated with an augmented reality display, in accordance with an embodiment. At block 2610 of method 2600, processing logic receives a stream of images of a patient's face from an image capture device. The image capture device may be an image capture device of an AR display worn by a dental practitioner.

At block 2620, processing logic processes the stream of images. Processing the stream of images may include processing the stream of images using one or more machine learning profiles that have been trained to identify particular types of images. For example, a first machine learning profile may be trained to identify images that represent a left and/or right profile view of a patient's face. A second machine learning profile may be trained to identify images that represent a front view of a patient's face. An additional machine learning profile may be trained to identify images that represent a mouth that is maximally open, and so on. The machine learning profiles may be generated using the machine learning profile generation techniques described herein above. Alternatively, image analysis profiles or models may be generated manually (without using machine learning) that analyze images to determine specific properties of the images. For example, an image analysis profile may be generated that searches for a nose tip and a nose base, that computes a vector between the nose tip and nose base, and that computes a horizontal component of the vector. In one embodiment, an image analysis profile may be generated that identifies most prominent facial features in the images (e.g., protruding nose, lips, chin, etc.). Those images that include the most prominent facial features may be selected using such an image analysis profile.

At block 2630, processing logic may determine a subset of images from the stream of images that satisfy image selection criteria. At block 2638, processing logic selects the determined subset. The image analysis profiles or models may be used to process each incoming image, and then from the images received so far select an image that is a best match for a particular type of image. For example, image analysis profiles or models may select a best left and right profile view from the image received so far. Then if a better left or right profile view is later received, that previously selected left or right profile view image may be discarded and replaced by the new left or right profile view. The process may continue until no new images are received.

Examples of images that may be selected for the determined subset may include an image representing a left profile of the face in which a mouth of the patient is closed, an image representing a right profile of the face in which the mouth of the patient is closed, an image representing the left profile of the face in which the mouth of the patient is open, an image representing the right profile of the face in which the mouth of the patient is open, an image representing a front view of the face in which the mouth of the patient is closed, and an image representing the front view of the face in which the mouth of the patient is open. Other examples of images that may be selected for the determined subset may include an image in which a lower jaw of the patient has been moved left relative to an upper jaw of the patient, an image in which the lower jaw of the patient has been moved right relative to the upper jaw of the patient, and an image in which the mouth is maximally open.

In one embodiment, an image analysis profile for identifying best profile images is used to analyze images. For each image, processing logic may perform image recognition on the image to identify a tip of a nose and a base of the nose. Alternatively, the processing logic may identify a tip of the nose and one or more other facial features. Processing logic may then compute a vector between the tip of the nose and the base of the nose (or between the tip of the nose and the one or more other facial features). Processing logic may then determine a direction and magnitude of a horizontal component of the vector. A vector having a first direction may be identified as a left profile image and a vector having a second direction may be identified as a right profile image. Processing logic may compare, between each of the plurality of images, the direction and the magnitude for the horizontal component of the vector. Processing logic may then select the image having the maximum magnitude and a first direction for the horizontal portion of the vector as the left profile image and may select the image having the maximum magnitude and a second direction for the horizontal portion of the vector as the right profile image.

In one embodiment, an image analysis profile for identifying best jaw articulation extreme images is used to analyze images. For each image, processing logic may perform image recognition on the image to identify an upper jaw of a patient and to identify a lower jaw of the patient. Processing logic may additional determine a midline of the upper jaw by finding a midline between the patient's ears, between the patient's eyes, between equal left and right halves of teeth on the upper jaw, or by another technique. An average of midlines computed from the eyes, nose, ears, teeth, cheek bones, and/or other facial features may also be determined. The midline is a vertical line that is at the middle of the patient's face (e.g., that acts as an axis of symmetry between the left and right side of the patient's face). The upper jaw midline is the midline for the upper dental arch and the lower jaw midline is for the lower dental arch.

Processing logic may additionally determine a midline of the lower jaw of the patient. The lower jaw midline may be determined by determining an axis of symmetry for the lower lip of the patient, for the lower exposed teeth of the patient, for the lower jaw profile of the patient, or from other facial features of the lower jaw. Midlines of multiple different facial features of the lower jaw may additionally be averaged. Processing logic may then determine a horizontal distance between the upper jaw midline and the lower jaw midline.

Processing logic may compare, between each of the plurality of images, the horizontal distance between the first midline and the second midline. Processing logic may then select an image having a maximum horizontal distance and a lower jaw that is to the right of the upper jaw. Processing logic may additionally select an image having a maximum horizontal distance and a lower jaw that is to the left of the upper jaw.

At block 2640, processing logic stores the selected subset of images. At block 2645, processing logic generates one or more models of the patient's jaw from the selected subset of images. The jaw model may be, for example, an articulation model of the patient's jaw. For example, processing logic may use multiple images of the patient's jaw that are taken in multiple arch positions (e.g., max to the right, max to the left, max protruding, and so on) to calculate intermediate jaw positions. The calculated positions may then be used to generate an articulation model of the patient's jaw in different positions. Alternatively, or additionally, the selected images may be used to determine left-right symmetry for a patient, to determine a smile line for the patient, to determine facial proportions for the patient, to gather a record of post treatment results, to gather a record of pre-treatment conditions, to record progress of an orthodontic treatment, and so on.

At block 2660, processing logic determines whether additional images have been received. If additional images have been received, the method returns to block 2630 and the additional images are processed and then compared to the previously selected subset of images. The new images may then either be discarded or used to replace one or more of the previously selected images. For example, if a previous left profile image was of a patient turning their head partway to the left and a new image is of the patient turning their head all the way to the left, then the new image may replace the previously selected left profile image. The previously generated jaw models may then be updated based on the newly selected image or images.

If no additional images are received at block 2660, then the method may continue to block 2680. At block 2680, processing logic generates an occlusion map for the patient based on the one or more jaw models and/or based on a virtual 3-D model of an upper and lower arch of the patient generated from an intraoral scan of the upper and lower arches.

The occlusion plane is defined as the horizontal plane through the tips of the buccal cusps of the premolars or the tips of the mesiobuccal cusps of the first molars and first premolars. In some embodiments, the occlusion plane is used as a reference plane for defining an X-Y-Z grid system used to generate the occlusion map. Cross-sections that are normal to the occlusion plane and that go through a point on an upper tooth and a point on an opposite lower tooth may be used to determine distances between surfaces of the upper and lower teeth at various areas. Alternatively, or additionally, some cross-sections may be taken at a cross-sectional plane passing through the Z-axis and making an arbitrary angle with the Y axis.

Since the coordinates of all points comprising the virtual 3-D model of an upper and lower arch are known, the distances between opposite points on the grid line can easily be determined. Let the distance between point I' on the surface of upper tooth and its "facing partner" point I" on the surface of lower tooth, be denoted by d(I',I"), then $$d(I',I'')=|Z(I')-Z(I'')|,$$

where Z(I'), Z(I") are the Z coordinates of the points I', I", respectively. The absolute value of the difference between the coordinates has been taken since only the magnitude of the difference is of interest.

In this manner the distances between the pairs of points may be found. Different distance values may be represented in the occlusion map using different colors. For example, distances of 0 (which denote contact), may be shown as red, small distances may be shown as orange, medium distances may be shown as yellow, and larger distances may be shown as blue. The above distances may then be represented by a map of colored dots, or pixels, according to a particular color scheme (e.g., such as provided in the above example). In other words, the values of the distances between opposite pairs of points on opposite upper and lower teeth are mapped onto colored pixels on a straight line with the distance between adjacent pixels equal to the distance between adjacent grid lines on which the adjacent pairs of opposite points corresponding to the adjacent pixels are situated.

The map of distances between pairs of opposite points on opposite teeth is referred to as an "occlusion map" for the opposite pair of teeth. It is often convenient to superimpose an occlusion map on the upper dental arch and/or lower dental arch. The occlusion map could be superimposed on the outline of a view of the teeth of both the upper and lower arches (e.g., as viewed by a dental practitioner through and AR display). This affords easy monitoring of dental procedures by allowing a dental practitioner to see the relationship between the surfaces of opposite teeth (i.e. the distances between opposite pairs of points on opposite teeth) with the jaws closed, by studying the dental occlusion map with respect to both the upper and lower teeth. A tooth (or teeth) can be fitted with a crown (or a bridge), or a tooth can be ground, and the influence of the change made on the relationship between opposite teeth on the upper and lower jaws can be seen by noting color changes in the dental occlusion map overlaid on the view of the dental arches as seen by the dental practitioner through the AR display.

Changes can continue to be made until a desired spatial relationship between opposite teeth is achieved.

The jaw articulation model can be applied to the virtual 3-D model of the upper and lower arches to determine or refine occlusion maps for different relative jaw positions between the upper and lower dental arches. An average of the occlusion maps for the different relative positions of the upper and lower dental arches may optionally be computed to determine a final occlusion map. The average of the occlusion maps may be a weighted average, where more likely upper jaw to lower jaw relative positions (e.g., less extreme positions) are weighted more heavily than less likely upper to lower jaw relative positions. The jaw articulation model may additionally improve the identification of functioning contacts (contacts between upper and lower teeth that are on the inner region of the teeth) and interfering contacts (contacts between upper and lower teeth that are in the outer region of the teeth). The articulation model can show, for example, how contact between the upper and lower teeth has changed from tooth grinding.

Figure 27:
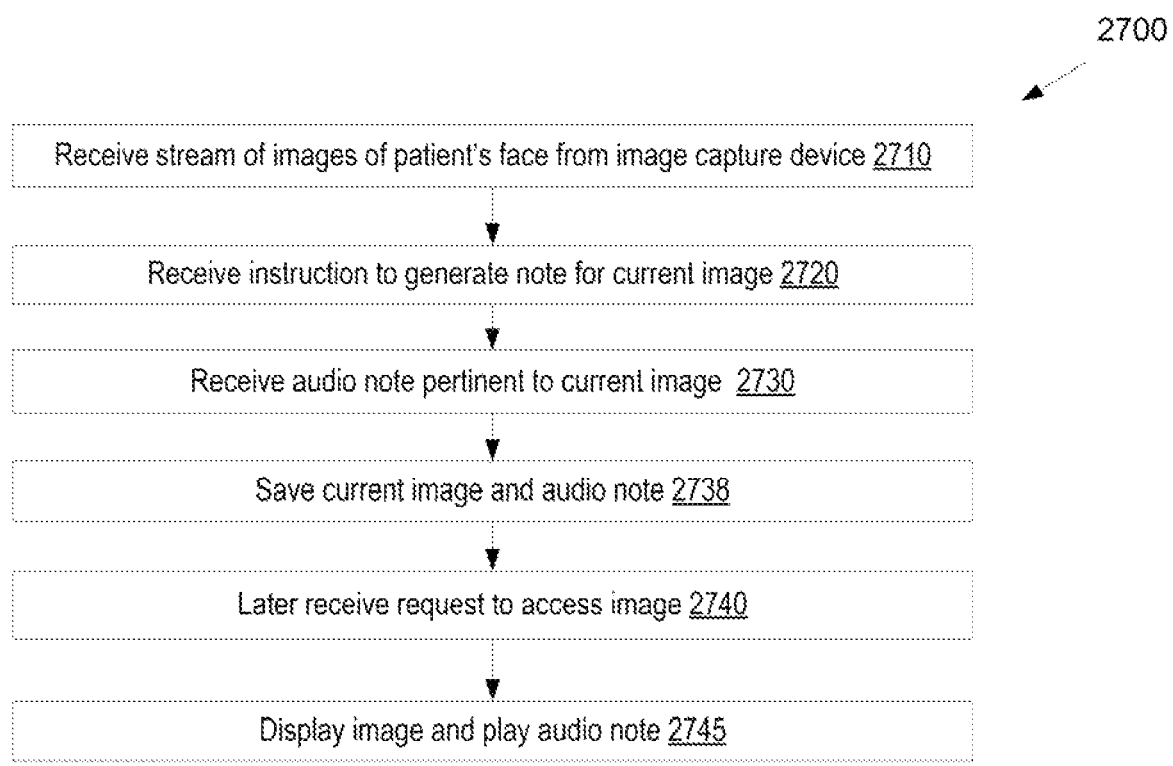
FIG. 27 illustrates a flow diagram for a method of attaching audio notes to image data from an image capture device associated with an augmented reality display, in accordance with an embodiment.

FIG. 27 illustrates a flow diagram for a method 2700 of attaching audio notes (also referred to as voice notes) to image data from an image capture device associated with an augmented reality display, in accordance with an embodiment. At block 2710 of method 2700, processing logic receives a stream of images of a patient's face from an image capture device associated with an AR display. The AR display may be worn by a dental practitioner viewing a patient's face. At block 2720, processing logic receives an instruction to generate a note for a current image. The current image may be an image that represents a view of the patient's face that the dental practitioner currently sees when he issues the command to generate the note. The command to generate the note may be issued via a voice command, a gesture command, or a press of a button on an input device.

At block 2730, processing logic receives an audio note pertinent to the current image. For example, the audio note may be a diagnosis of a dental condition visible in the current image, a reminder to examine or check up on a dental condition, and so on. At block 2738, processing logic saves the current image and the audio note. The audio note may be saved as an audio file such as a way file, an mp3 file, an aac file, for or other audio file type. The current image may be saved as a jpg file, a bmp file, a png file, or other image file type. The image file and the audio file may be linked (e.g., by storing them as being related in a relational database). Accordingly, when processing logic later receives a request to access the image at block 2740, processing logic may retrieve both the image and the associated audio note. Processing logic may then display the image and in parallel play the audio note at block 2745.

Method 2700 provides the advantage that a dental practitioner's hands may remain free while taking the audio notes. The dental practitioner can initiate the note taking process, generate the voice note, generate the image to associate with the voice note, and store the image and voice note while the dental practitioner is working on a patient's oral cavity all without taking his hands away from the patient's oral cavity. Thus, notes can be generated without any burden to the dental practitioner and without taking additional time for the dental practitioner.

Figure 28:
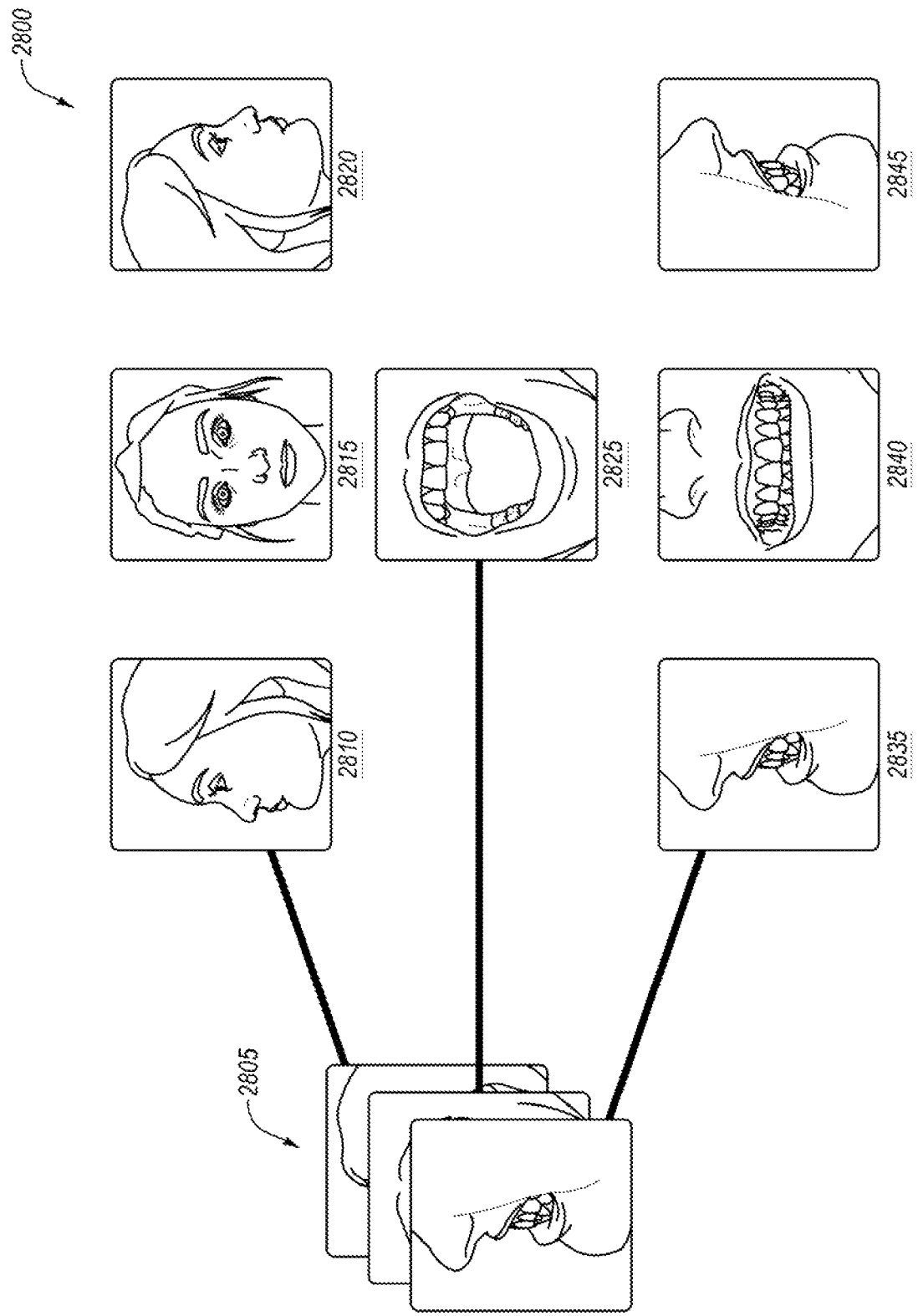
FIG. 28 illustrates selected images from a set of images generated by an image capture device associated with an augmented reality display, in accordance with an embodiment.

FIG. 28 illustrates selected images 2800 from a set of images generated by an image capture device associated with an augmented reality display, in accordance with an embodiment. As shown, a plurality of images 2805 are received. From the plurality of images 2805, a left profile image with mouth closed 2810, front view image with mouth closed 2815, right profile image with mouth closed 28220, image with mouth maximally open 2825, left profile image with mouth open (smiling and showing teeth) 2835, front view image with mouth open (smiling and showing teeth) 2840 and right profile image with mouth open (smiling and showing teeth) 2845 are selected. The remainder of the images 2805 may be discarded. These selected images may be used to generate a jaw model.

Figure 29:
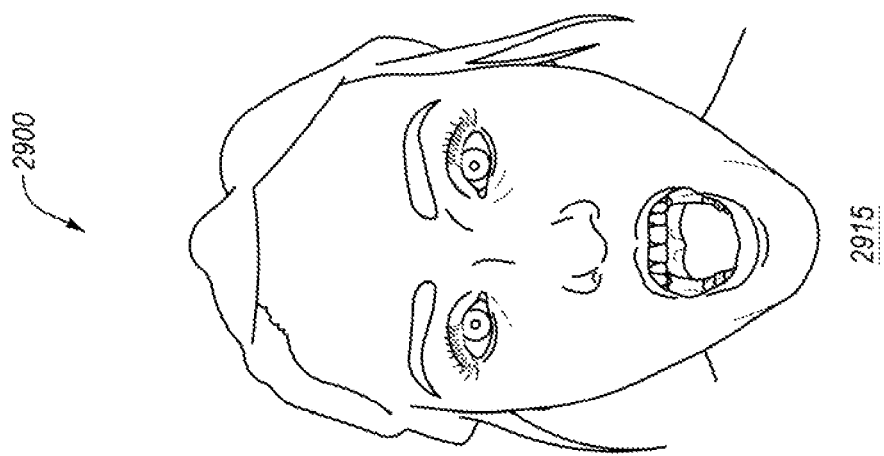
FIG. 29 illustrates additional selected images from a set of images generated by an image capture device associated with an augmented reality display, in accordance with an embodiment.
Figure 29:
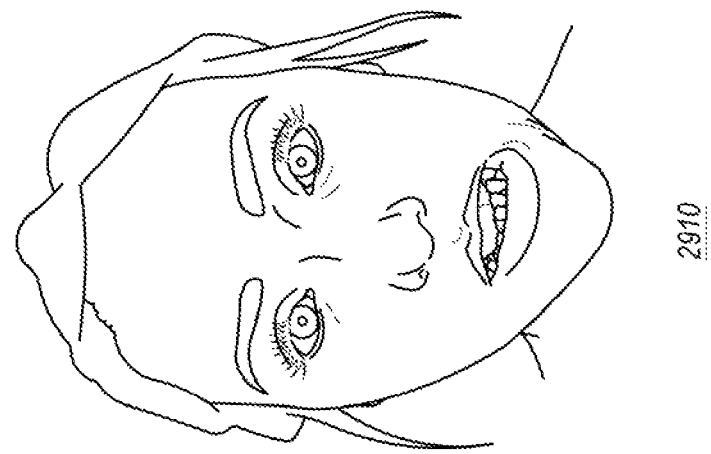
Figure 29:
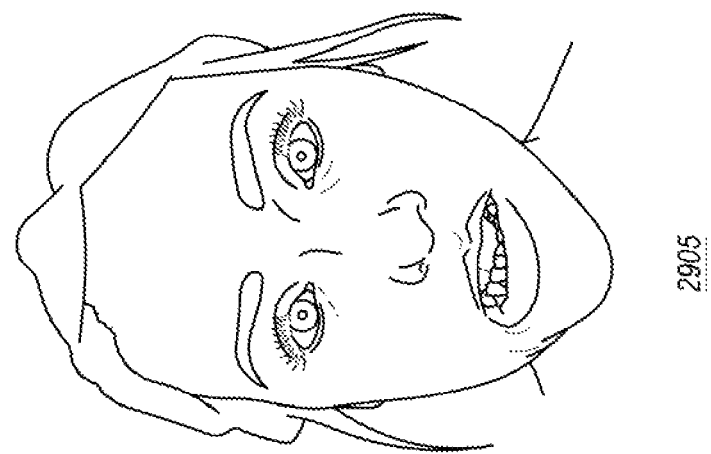

FIG. 29 illustrates additional selected images 2900 from a set of images generated by an image capture device associated with an augmented reality display, in accordance with an embodiment. The selected images include a first image 2905 in which the patient is moving his lower jaw to the right as much as possible, a second image 2910 in which the patient is moving his lower jaw to the left as much as possible, and a third image 2915 in which the patient has opened his mouth as wide as possible. These selected images may be used to generate a jaw model, such as an articulation model.

Figure 30:
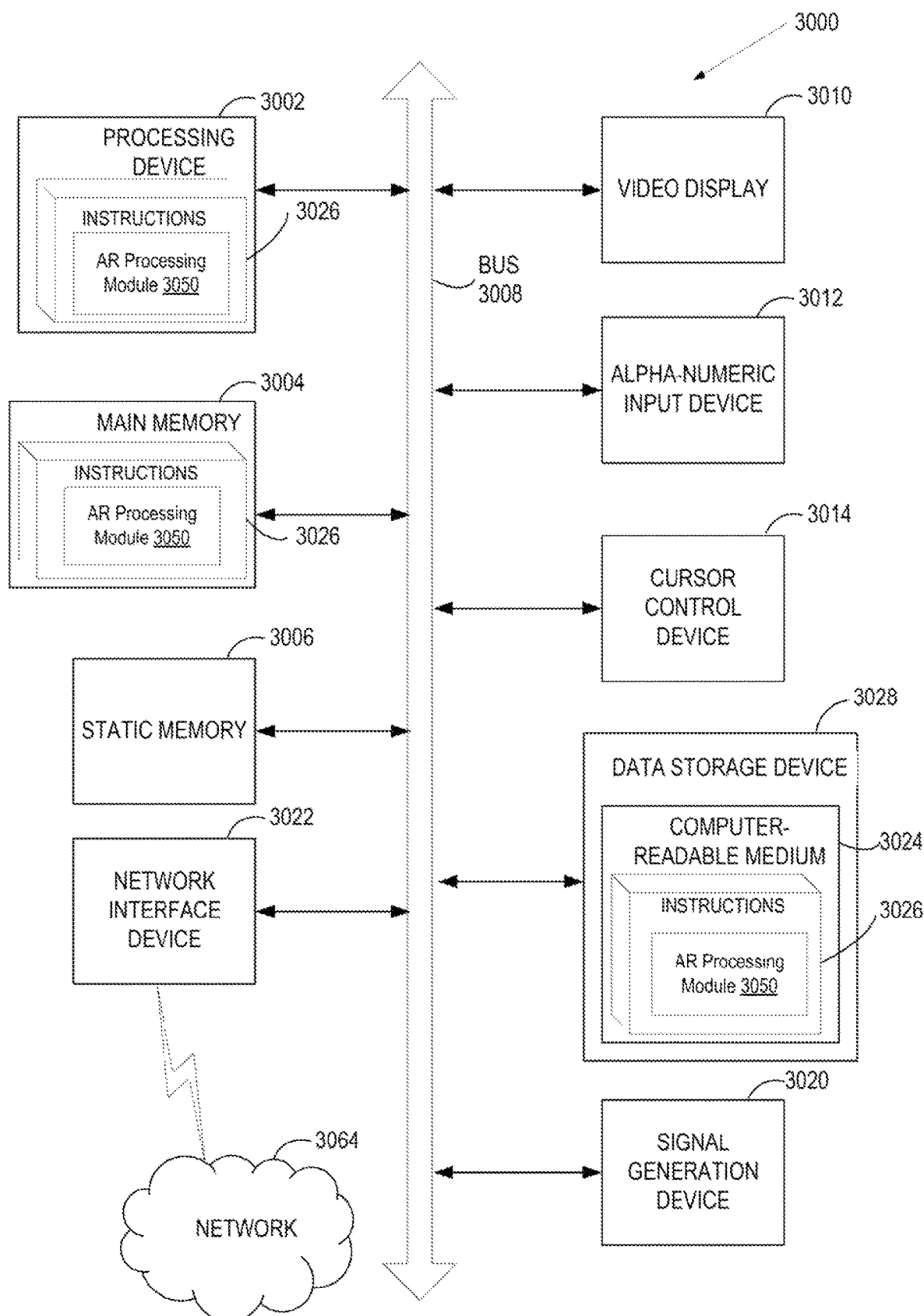
FIG. 30 illustrates a block diagram of an example computing device, in accordance with embodiments of the present invention.

FIG. 30 illustrates a diagrammatic representation of a machine in the example form of a computing device 3000 within which a set of instructions, for causing the machine to perform any one or more of the methodologies discussed herein, may be executed. In alternative embodiments, the machine may be connected (e.g., networked) to other machines in a Local Area Network (LAN), an intranet, an extranet, or the Internet. The machine may operate in the capacity of a server or a client machine in a client-server network environment, or as a peer machine in a peer-to-peer (or distributed) network environment. The machine may be a personal computer (PC), a tablet computer, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines (e.g., computers) that individually or jointly execute a set (or multiple sets) of instructions to perform any one or more of the methodologies discussed herein. In one embodiment, the computer device 3000 corresponds to computing devices 105 of FIG. 1.

The example computing device 3000 includes a processing device 3002, a main memory 3004 (e.g., read-only memory (ROM), flash memory, dynamic random access memory (DRAM) such as synchronous DRAM (SDRAM), etc.), a static memory 3006 (e.g., flash memory, static random access memory (SRAM), etc.), and a secondary memory (e.g., a data storage device 3028), which communicate with each other via a bus 3008.

Processing device 3002 represents one or more general-purpose processors such as a microprocessor, central processing unit, or the like. More particularly, the processing device 3002 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processing device 3002 may also be one or more special-purpose processing devices such as an application specific integrated circuit (ASIC), a field programmable gate array (FPGA), a digital signal processor (DSP), network processor, or the like. Processing device 3002 is configured to execute the processing logic (instructions 3026) for performing operations and steps discussed herein.

The computing device 3000 may further include a network interface device 3022 for communicating with a network 3064. The computing device 3000 also may include a video display unit 3010 (e.g., a liquid crystal display (LCD) or a cathode ray tube (CRT)), an alphanumeric input device 3012 (e.g., a keyboard), a cursor control device 3014 (e.g., a mouse), and a signal generation device 3020 (e.g., a speaker).

The data storage device 3028 may include a machine-readable storage medium (or more specifically a non-transitory computer-readable storage medium) 3024 on which is stored one or more sets of instructions 3026 embodying any one or more of the methodologies or functions described herein, such as instructions for an AR processing module 3050. A non-transitory storage medium refers to a storage medium other than a carrier wave. The instructions 3026 may also reside, completely or at least partially, within the main memory 3004 and/or within the processing device 3002 during execution thereof by the computer device 3000, the main memory 3004 and the processing device 3002 also constituting computer-readable storage media.

The computer-readable storage medium 3024 may also be used to store an AR processing module 3050, which may correspond to the similarly named component of FIGS. 1A-1B. The computer readable storage medium 3024 may also store a software library containing methods for an AR processing module 3050. While the computer-readable storage medium 3024 is shown in an example embodiment to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium other than a carrier wave that is capable of storing or encoding a set of instructions for execution by the machine and that cause the machine to perform any one or more of the methodologies of the present invention. The term "computer-readable storage medium" shall accordingly be taken to include, but not be limited to, solid-state memories, and optical and magnetic media.

It is to be understood that the above description is intended to be illustrative, and not restrictive. Many other embodiments will be apparent upon reading and understanding the above description. Although embodiments of the present invention have been described with reference to specific example embodiments, it will be recognized that the invention is not limited to the embodiments described, but can be practiced with modification and alteration within the spirit and scope of the appended claims. Accordingly, the specification and drawings are to be regarded in an illustrative sense rather than a restrictive sense. The scope of the invention should, therefore, be determined with reference to the appended claims, along with the full scope of equivalents to which such claims are entitled.

What is claimed is:

1. A method comprising:
  receiving, from an image capture device associated with an augmented reality (AR) display and by a processing device, a plurality of images of a face of a patient;
  selecting, by the processing device, a subset of the plurality of images that meet one or more image selection criteria, the selecting comprising:
    determining, from the plurality of images, a first image that represents a first position extreme for the face;
    determining, from the plurality of images, a second image that represents a second position extreme of the face;
    selecting the first image; and
    selecting the second image; and
  generating, by the processing device, a digital model of a jaw of the patient based at least in part on the subset of the plurality of images that have been selected.

2. The method of claim 1, further comprising:
  discarding a remainder of the plurality of images that have not been selected.

3. The method of claim 1, wherein the first image comprises a left profile of the face and the second image comprises a right profile of the face.

4. The method of claim 1, wherein determining that the first image represents the first position extreme of the face comprises:
  performing the following for each image of the plurality of images:
    identifying a tip of a nose in the image;
    identifying a base of the nose in the image;
    generating a vector between the base of the nose and the tip of the nose; and
    determining a direction and a magnitude for a horizontal component of the vector;
  comparing, between each of the plurality of images, the direction and the magnitude for the horizontal component of the vector; and
  determining that the first image has a first direction and a maximum magnitude for the horizontal component of the vector.

5. The method of claim 1, wherein the subset of the plurality of images comprises:
  an image representing a left profile of the face in which a mouth of the patient is closed;
  an image representing a right profile of the face in which the mouth of the patient is closed;
  an image representing the left profile of the face in which the mouth of the patient is open;
  an image representing the right profile of the face in which the mouth of the patient is open;
  an image representing a front view of the face in which the mouth of the patient is closed; and
  an image representing the front view of the face in which the mouth of the patient is open.

6. The method of claim 1, wherein:
  the first image is an image in which a lower jaw of the patient has been moved left relative to an upper jaw of the patient;
  the second image is an image in which the lower jaw of the patient has been moved right relative to the upper jaw of the patient; and
  the subset of the plurality of images further comprises a third image in which a mouth of the patient is maximally open.

7. The method of claim 6, wherein determining the first image comprises:
  performing the following for each image of the plurality of images:
    identifying a first midline of the upper jaw;
    identifying a second midline of the lower jaw; and
    determining a horizontal distance between the first midline and the second midline;
  comparing, between each of the plurality of images, the horizontal distance between the first midline and the second midline; and determining that the first image has a maximum horizontal distance.

8. The method of claim 6, wherein the digital model of the jaw comprises an articulation model of the jaw that defines motion vectors for the jaw.

9. The method of claim 8, further comprising:
computing an occlusion map for the jaw based on the articulation model and a three-dimensional model of the jaw.

10. The method of claim 1, wherein the plurality of images are received in an image stream, the method further comprising:
receiving an instruction to generate a note for a current image;
receiving an audio note pertinent to the current image;
saving the current image and the audio note, wherein the current image and audio not are linked such that the audio note plays when the current image is displayed.

11. A system comprising:
a memory device; and
a processing device operatively coupled to the memory device, the processing device to:
receive, from an image capture device associated with an augmented reality (AR) display, a plurality of images of a face of a patient;
select a subset of the plurality of images that meet one or more image selection criteria, wherein selecting the subset comprises:
determining, from the plurality of images, a first image that represents a first position extreme for the face;
determining, from the plurality of images, a second image that represents a second position extreme of the face;
selecting the first image; and
selecting the second image; and
generate a model of a jaw of the patient based at least in part on the subset of the plurality of images that have been selected.

12. The system of claim 11, wherein the processing device is further to:
discard a remainder of the plurality of images that have not been selected.

13. The system of claim 11, wherein the first image comprises a left profile of the face and the second image comprises a right profile of the face.

14. The system of claim 11, wherein determining that the first image represents the first position extreme of the face comprises:
performing the following for each image of the plurality of images:
identifying a tip of a nose in the image;
identifying a base of the nose in the image;
generating a vector between the base of the nose and the tip of the nose; and
determining a direction and a magnitude for a horizontal component of the vector;
comparing, between each of the plurality of images, the direction and the magnitude for the horizontal component of the vector; and
determining that the first image has a first direction and a maximum magnitude for the horizontal component of the vector.

15. The system of claim 11, wherein the subset of the plurality of images comprises:
an image representing a left profile of the face in which a mouth of the patient is closed;
an image representing a right profile of the face in which the mouth of the patient is closed;
an image representing the left profile of the face in which the mouth of the patient is open;
an image representing the right profile of the face in which the mouth of the patient is open;
an image representing a front view of the face in which the mouth of the patient is closed; and
an image representing the front view of the face in which the mouth of the patient is open.

16. The system of claim 11, wherein:
the first image is an image in which a lower jaw of the patient has been moved left relative to an upper jaw of the patient;
the second image is an image in which the lower jaw of the patient has been moved right relative to the upper jaw of the patient; and
the subset of the plurality of images further comprises a third image in which a mouth of the patient is maximally open.

17. The system of claim 16, wherein determining the first image comprises:
performing the following for each image of the plurality of images:
identifying a first midline of the upper jaw;
identifying a second midline of the lower jaw; and
determining a horizontal distance between the first midline and the second midline;
comparing, between each of the plurality of images, the horizontal distance between the first midline and the second midline; and
determining that the first image has a maximum horizontal distance.

18. The system of claim 11, wherein the model of the jaw comprises an articulation model of the jaw that defines motion vectors for the jaw.

19. The system of claim 18, wherein the processing device is further to:
compute an occlusion map for the jaw based on the articulation model and a three-dimensional model of the jaw.

20. The system of claim 11, wherein the plurality of images are received in an image stream, and wherein the processing device is further to:
receive an instruction to generate a note for a current image;
receive an audio note pertinent to the current image;
save the current image and the audio note, wherein the current image and audio not are linked such that the audio note plays when the current image is displayed.

21. A non-transitory computer readable storage medium comprising instructions that, when executed by a processing device, cause the processing device to perform operations comprising:
receiving, from an image capture device associated with an augmented reality (AR) display, a plurality of images of a face of a patient;
selecting a subset of the plurality of images that meet one or more image selection criteria, the selecting comprising:
determining, from the plurality of images, a first image that represents a first position extreme for the face;
determining, from the plurality of images, a second image that represents a second position extreme of the face;
selecting the first image; and
selecting the second image; and generating a model of a jaw of the patient based at least in part on the subset of the plurality of images that have been selected.

22. The non-transitory computer readable storage medium of claim 21, the operations further comprising:
discarding a remainder of the plurality of images that have not been selected.

23. The non-transitory computer readable storage medium of claim 21, wherein the first image comprises a left profile of the face and the second image comprises a right profile of the face.

24. The non-transitory computer readable storage medium of claim 21, wherein determining that the first image represents the first position extreme of the face comprises:
performing the following for each image of the plurality of images:
identifying a tip of a nose in the image;
identifying a base of the nose in the image;
generating a vector between the base of the nose and the tip of the nose; and
determining a direction and a magnitude for a horizontal component of the vector;
comparing, between each of the plurality of images, the direction and the magnitude for the horizontal component of the vector; and
determining that the first image has a first direction and a maximum magnitude for the horizontal component of the vector.

25. The non-transitory computer readable storage medium of claim 21, wherein:
the first image is an image in which a lower jaw of the patient has been moved left relative to an upper jaw of the patient;
the second image is an image in which the lower jaw of the patient has been moved right relative to the upper jaw of the patient; and
the subset of the plurality of images further comprises a third image in which a mouth of the patient is maximally open.

26. The non-transitory computer readable storage medium of claim 25, wherein determining the first image comprises:
performing the following for each image of the plurality of images:
identifying a first midline of the upper jaw;
identifying a second midline of the lower jaw; and
determining a horizontal distance between the first midline and the second midline ;
comparing, between each of the plurality of images, the horizontal distance between the first midline and the second midline; and
determining that the first image has a maximum horizontal distance.

27. The non-transitory computer readable storage medium of claim 26, wherein the model of the jaw comprises an articulation model of the jaw that defines motion vectors for the jaw, the operations further comprising:
computing an occlusion map for the jaw based on the articulation model and a three-dimensional model of the jaw.

28. The non-transitory computer readable storage medium of claim 21, wherein the plurality of images are received in an image stream, the operations further comprising:
receiving an instruction to generate a note for a current image;
receiving an audio note pertinent to the current image;
saving the current image and the audio note, wherein the current image and audio not are linked such that the audio note plays when the current image is displayed.

* * * * *